US005843709A

United States Patent [19]

Entian et al.

[11] Patent Number: 5,843,709

[45] Date of Patent: Dec. 1, 1998

[54] BIOSYNTHETIC PROCESS FOR THE PREPARATION OF CHEMICAL COMPOUNDS

[75] Inventors: Karl-Dieter Entian, Oberursel/Ts.; Friedrich Götz, Tübingen, both of Germany; Norbert Schnell, Pasadena, Calif.; Johannes Augustin, Tübingen, Germany; Germar Engelke, Frankfurt am Main, Germany; Ralf Rosenstein, Reutlingen, Germany; Cortina Kaletta, München, Germany; Cora Klein, Offenbach, Germany; Bernd Wieland, Rottenburg, Germany; Thomas Kupke, Tübingen, Germany; Günther Jung, Tübingen, Germany; Roland Kellner, Heppenheim, Germany

[73] Assignee: Dr. Karl Thomae GmbH, Germany

[21] Appl. No.: 466,961

[22] Filed: Jun. 6, 1995

Related U.S. Application Data

[62] Division of Ser. No. 392,625, Feb. 22, 1995, which is a continuation of Ser. No. 876,791, Apr. 30, 1992, abandoned, which is a continuation of Ser. No. 784,234, Oct. 31, 1991, abandoned, which is a continuation-in-part of Ser. No. 353,590, May 18, 1989, abandoned.

[30] Foreign Application Priority Data

May 18, 1988 [GB] United Kingdom .................. 8811761

[51] Int. Cl.[6] ............................ C12P 21/06; C12N 9/00; C12N 1/00; A61K 38/00

[52] U.S. Cl. ........................ 435/69.1; 435/183; 435/69.7; 435/252.3; 435/252.33; 435/252.5; 435/253.4; 435/253.5; 435/320.1; 435/882; 530/326; 530/825; 536/23.2; 536/23.4; 536/23.7

[58] Field of Search .................................. 435/69.7, 183, 435/252.3, 252.33, 320.1, 69.1, 252.5, 253.4, 253.5; 530/300, 350, 326, 825; 536/23.2, 23.4, 23.7

[56] References Cited

U.S. PATENT DOCUMENTS 4,716,115 12/1987 Gonzalez et al. .................... 435/172.3
5,231,013 7/1993 Jung et al. ............................ 435/71.3

FOREIGN PATENT DOCUMENTS 0 342 658 11/1989 European Pat. Off. .

OTHER PUBLICATIONS

Allgaier et al., "Epidermin: Sequencing of a Heterodetic Tetracyclic 21–Peptide Amide Antibiotic", *Eur. J. Biochem. 160(1)*:9–22 (1986).

Augustin et al., "Genetic Analysis of Epidermin Biosynthetic Genes and Epidermin–Negative Mutants of *Staphylococcus epidermidis", Eur. J. Biochem. 204*(3):1149–1154 (Mar., 1992).

Augustin et al., "Identification of Epidermin Biosynthetic Genes by Complementation Studies and Heterologous Expression", in: *Proceedings of the 1st International Workshop on Lantibiotics. Nisin Novel Lantibiotics 1991*, pp. 277–286 (1991).

Banerjee et al., "Structure and Expression of a gene Encoding the Precursor of Subtilin, a Small Protein Antibiotic", *J. Biol. Chem. 263(19)*:9508–9514 (Jul. 5, 1988).

Buchman et al., "Structure, Expression, and Evolution of a Gene Encoding the Precursor of Nisin, a Small Protein Antibiotic", *J. Biol. Chem. 263(31)*:16260–16266 (Nov. 5, 1988).

Entian et al., "Structure and dNA–Sequence Analysis of the Staphylococcal Lantibiotics Epidermin and Gallidermin", *Abstr. of the Annual Meeting of Am. Soc. for Microbiol. 89(0)*:182, Abstr. No. H–78 (May, 1989).

Fiedler et al., "Purification of the Hydrophilic Antibiotics Epidermin, Gallidermin, and Nikkomycin Z by Preparative Reversed–Phase HPLC", *Chem. Abstr. 110*:583, Abstr. No. 210845v (Jan. 2, 1989).

Fiedler et al., "Purification of the Hydrophilic Antibiotics Epidermin, Gallidermin, and Nikkomycin Z by Preparative Reversed–Phase HPLC", *Chromatographia 26*:215–220 (Dec., 1988).

Gennaro et al., "A Site–Specific Recombination Function in *Staphylococcus aureus* Plasmids", *J. Bacteriol. 169(6)*:2601–2610 (Jun., 1987).

Horinouchi et al., "Nucleotide sequence and Functional Map of pC194, a Plasmid that Specifies Inducible Chloramphenicol Resistance", *J. Bacteriol. 150(2)*:815–825 (1982).

Jung, G., "Lantibiotics — Ribosomally Synthesized Biologically Active Polypeptides Containing Sulfide Bridges and α,β–Didehydroamino Acids", *Angew. Chem. Int. Ed. Engl. 30 (9)*1051–1068 (Sep., 1991).

Kaletta et al., "Pep5, a New Lantibiotic: Structural Gene Isolation and Prepeptide Sequence", *Arch. Microbiol. 152(1)*:16–19 (Jun., 1989)

(List continued on next page.)

*Primary Examiner*—Robert A. Wax
*Assistant Examiner*—Elizabeth Slobodyansky
*Attorney, Agent, or Firm*—Sterne, Kessler, Goldstein & Fox P.L.L.C.

[57] ABSTRACT

A bacterial host is described which is transformed by a plasmid coding for a polypeptide precursor wherein the host comprises a multi-enzyme complex capable of reacting with the expressed polypeptide precursor to produce a polypeptide comprising at least one dehydroamino acid and/or at least one lanthione bridge. A process for producing a polypeptide comprising at least one dehydroamino acid and/or at least one lanthione bridge, such as gallidermin, is also described. A plasmid capable of transforming a bacterial host is additionally described.

Also disclosed are recombinant DNA molecules which specify Epi B, Epi C, Epi D, Epi P and Epi Q, enzymes which are involved in the biosynthesis of lantibiotic epidermin.

21 Claims, 43 Drawing Sheets

OTHER PUBLICATIONS

Kaletta, C. and Entian, K.–D., "Nisin, a Peptide Antibiotic: Cloning and Sequencing of the nisA Gene and Posttranslational Processing of its Peptide Product", *J. Bacteriol. 171(3)*:1597–1601 (Mar., 1989).

Kaletta, C. et al., "Cloning of Genes Coding for Polypeptide Antibiotics (Lantibiotics) and Posttranslational Processing of Their Peptide Products", *DECHEMA Biotechnology Conf. 3, Part A*:33–35 (May, 1989).

Kellner et al., "Gallidermin: A New Lanthionine–Containing Polypeptide Antibiotic", *Eur. J. Biochem. 177(1)*:53–59 (Feb. 1988).

Kellner et al., "Gallidermin: A New Lanthionine–Containing Polypeptide Antibiotic", *Chem. Abstr. 110*:395, Abstract No. 4243u (Jan. 2, 1989).

Khan et al., "Complete Nucleotide Sequence of pT181, a Tetracycline–Resistance Plasmid from *Staphylococcus aureus", Plasmid 10*:251–259 (1983).

Klein et al., "Analysis of Genes Involved in Biosynthesis of the Lantibiotic Subtilin", *Appl. Env. Microbiol. 58(1)*:132–142 (1992).

Koide et al., "Cloning and Sequencing of the Major Intracellular Serine Protease Gene of *Bacillus subtilis", J. Bacteriol. 167(1)*:110–116 (1986).

Kupke, T. et al., "Purification and Characterization of EpiD, a Flavoprotein Involved in the Biosynthesis of the Lantibiotic Epidermin", *J. Bacteriol. 174(16)*:5354–5361 (Aug., 1992).

Schnell et al., "Prepeptide Sequence of Epidermin, A Ribosomally Synthesized Antibiotic with Four Sulfide–Rings", *Chem. Abstr. 109*:288, Abstract No. 144800c (Oct. 24, 1988).

Schnell et al., "Structural Gene Isolation and Prepeptide Sequence of Gallidermin, a New Lanthionine Containing antibiotic", *FEMS Microbiol. Lett. 58(2/3)*:263–268 (Apr., 1989).

Schnell et al., "Prepeptide Sequence of Epidermin, a Ribosomally Synthesized Antibiotic with Four Sulphide–Rings", *Nature 333*:276–278 (May 19, 1988).

Schnell et al., "The Operon–Like Organisation of Lantibiotic Epidermin Biosynthesis Genes", in: *Proceedings of the 1st International Workshop on Lantibiotics. Nisin Novel Lantibiotics 1991*, pp. 269–276 (1991).

Schnell et al., "Analysis of Genes Involved in the Biosynthesis of the Lantibiotic Epidermin", *Eur. J. Biochem. 204*:57–68 (1992).

Shiba et al., "Lanthionine Peptide", *Chem. Abstr. 104*:206, Abstract No. 2246z (1986).

Shiba et al., "Lanthionine Peptide" (with English translation), *Kagaku 40*416–417 (1985).

Vieira et al., "The pUC Plasmids, an M13mp7–Derived System for Insertion Mutagenesis and Sequencing with Synthetic Universal Primers", *Gene 19*:259–268 (1982).

Yanisch–Perron et al., "Improved M13 Phage Cloning Vectors and Host Strains: Nucleotide Sequences of the M13mp18 and pUC19 Vectors", *Gene 33*:103–119 (1985).

European Search Report for European Patent Application No. EP 89 108907, corresponding to U.S. Application Serial No. 07/353,590, filed May 18, 1989, which is the great-great–grandparent of this application.

Shiba et al. (1986) Biopolymers 25, S11–S19.

Fiedler et al. (1988) Chromatographia 26, 215–220.

FIG. 1A

```
1
TTTAAACTTTATATCATTAATATAATGTTTAGGAAAAGTAGAAGAAAATTACACTTTTGTAATTTTCTGAATATACATA
                                                                              am

              100
GTATTTATTTTGGGGGAGTACTAAAATAATAATTGAAAAGGGTTTTATAATCCTTTTTAATAAATTTTTAGGAGTGTTT

                                                         200
AAA ATG GAA GCA GTA AAA GAA AAA AAT GAT CTT TTT AAT CTT GAT GTT AAA GTT AAT GCA
     M   E   A   V   K   E   K   N   D   L   F   N   L   D   V   K   V   N   A
   -30                                     -20
```

*FIG.1B*

```
AAA GAA TCT AAC GAT TCA GGA GCT GAA CCA AGA ATT GCT AGT AAA TTT ATA TGT ACT CCT
 K   E   S   N   D   S   G   A   E   P   R ▲ I   A   S   K   F   I   C   T   P
     |                                   |   |
    -10                                 -1  +1

                           300
                            |
GGA TGT GCA AAA ACA GGT AGT TTT AAC AGT TAT TGT TGT TAATTCAGAAGAATTAGATTGGCAGGG
 G   C   A   K   T   G   S   F   N   S   Y   C   C  oc
 |                                       |
+10                                     +20

                                                        400
                                                         |
CTTCAATAGAGGCTCTGTCTTAATTTTGAGGTGAAATAGAATTGGATAATATATTTGTTCCATCGAATATATATATATGGT
     am                                  am
```

meso-Lanthionine threo-Methyllanthionine

FIG.5A
Unusual amino acids found in lanthionine peptide antibiotics ("lantibiotics") derived from protein proantibiotics
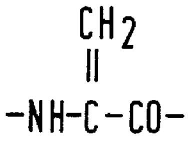
dehydroalanine, Dha
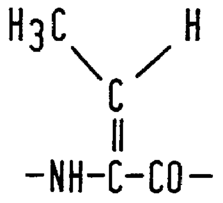
2,3-dehydro-2-aminobutyricacid, Dhb
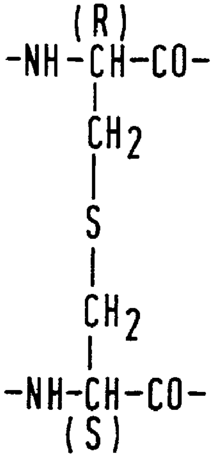
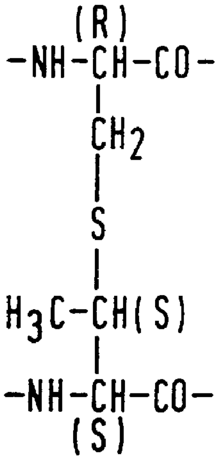
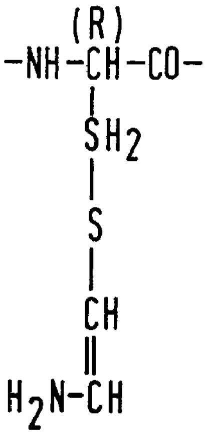

| | | |
|---|---|---|
| meso-lanthionine, meso-Lan, D-Ala-S-Ala | (2S,3S,6R)-3-methyl-lanthionine, 3-MeLan, D-Abu-S-Ala | S-(2-(7)-aminovinyl)-D-cysteine, D-Cys(Avi) |
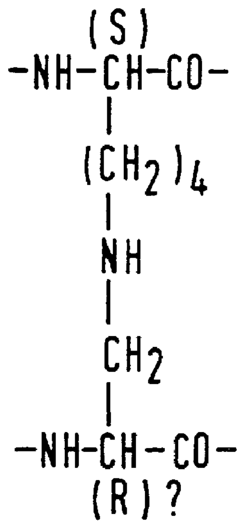
lysinoalanine
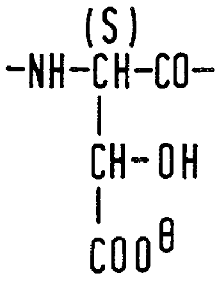
β-hydroxyaspartic acid, Asp(β-OH)
FIG.5B EMS 5 plus pCuGal (Gallidermin)

ESTD

| RT | AREA | TYPE | CAL # | AMOUNT |
|---|---|---|---|---|
| 0.73 | 8.4107E+07 | 1SBH | | 0.000 |
| 0.88 | 434710 | DTBB | | 0.000 |
| 1.01 | 3.7223E+07 | SHH | | 0.000 |
| 1.29 | 4978700 | SHH | | 0.000 |
| 1.38 | 5.3775E+07 | ISHH | | 0.000 |
| 1.53 | 349830 | TBB | | 0.000 |
| 2.78 | 343360 | TPB | | 0.000 |
| 3.78 | 444590 | TBY | | 0.000 |
| 4.03 | 218110 | TYY | | 0.000 |
| 7.54 | 408470 | TYB | 1 | 11.519 |
| 9.63 | 132570 | TBP | | 0.000 |

TOTAL AREA = 1.8242E+08
MIN FACTOR = 1.0000E+00

Gallidermin- Standard

ESTD

| RT | AREA | TYPE | CAL # | AMOUNT |
|---|---|---|---|---|
| 0.80 | 111200 | YH | | 0.000 |
| 0.87 | 1.0928E+07 | SHB | | 0.000 |
| 0.99 | 153190 | DTBB | | 0.000 |
| 5.92 | 156570 | PY | | 0.000 |
| 6.36 | 967060 | YY | | 0.000 |
| 7.15 | 580800 | PY | | 0.000 |
| 7.54 | 7492100 | YB | 1 | 211.280 |
| 8.65 | 212540 | BB | | 0.000 |
| 9.61 | 413430 | PY | | 0.000 |
| 9.68 | 256920 | D YY | | 0.000 |
| 9.94 | 255140 | I YH | | 0.000 |

TOTAL AREA = 2.1527E+07
MIN FACTOR = 1.0000E+00

FIG. 9A

```
Bg1II         20                                 40
AGATCTTGTGTTATATAACTAAACAAATTTCTCCATTCGTATTTAGAAAATTGACT
  D  Q  T  I  Y  S  F  L  N  R  W  E  Y  K  S  F  Q  S

60                80                  100              120
TTTATCAAGTTTATCCAAATATATATTTCCAGTATATTCTGTATTTAACCCAGCTAATATATTT
D  L  K  K  D  L  Y  I  N  G  T  Y  E  T  N  L  G  A  L  I  N

                140               160              180
AATAATGTACTTTTTCCACACCCACTTTCACCTATAATATTGTAGATATAACCTTTATGAAGAT
L  L  T  S  K  G  C  G  S  E  G  I  I  N  Y  I  Y  G  K  H  L  D

            200               220               240
CCAAACTTATAGAATTTATTATTTGTTTATTGTCTTTTGTGAAGTTCAAATCATTTATTTCCAT
  L  S  I  S  N  I  I  Q  K  N  D  K  T  F  N  L  D  N  I  E  M

        260               280               300
TTTTTGAACAAAGTTATTGTAAGTTGTTTTAATAGTTAATACCTCTTCTGGTTCTTTATTTATT
K  Q  V  F  N  N  Y  T  T  K  I  T  L  V  E  E  P  E  K  N  I

     320               340               360
TTTAAAATTCTATCTGAAGATCCAATTGCTCGTTGTACTTCCGTCCAATAAGATGTAATAGATA
K  L  I  R  D  S  S  G  I  A  R  Q  V  E  T  W  Y  S  T  I  S  V
```

FIG. 9B

```
380                 400                 420                 440
CTATTGGATTAATAATTTGAAATAAATATAAAACATAAGCAAACATATCTCCGCTTTTCATCAT
  I  P  N  I  I  Q  E  L  Y  L  V  Y  A  F  M  D  G  S  K  M  M

            460                 480                 500
ATTATTTTCCATTAAGTAATAACCCAAAAATAAAATACCAAAAATGTTAATAAATAGAATTAAG
 N  N  E  H  L  Y  Y  G  L  F  L  I  G  F  I  N  I  F  L  I  L

        520                 540                 560
TTCATAATTGGTTCGAAAAAAGATAATACTTTGATCTTATGTAACTCTATATCGAATATATTTT
N  M  I  P  E  F  F  S  L  V  K  I  K  H  L  E  I  D  F  I  N  K

    580                 600                 620
TTAATAGGGTATAGTTTTTTATTTTTTCGATATTATATGTACTTAAAGTTTTTATTAATTTTAT
  L  L  T  Y  N  K  I  K  E  I  N  Y  T  S  L  T  K  I  L  K  I

640                 660                 680
TGTAGATAATCTATTACTATAATAAGAAGATAATTTAGCAGTAGCTTCTTGAGATTTACTTGAT
 T  S  L  R  N  S  Y  Y  S  S  L  K  A  T  A  E  Q  S  K  S  S

700                 720                 740                 760
ACTCTTTTCATTATATTTCCTATAGGTAGTATTACAATTATCAATATAGGTAATGTACACACTA
V  R  K  M  I  N  G  I  P  L  I  V  I  I  L  I  P  L  T  C  V  L
```

FIG.9C

```
                780                           800                          820
AATATAATGTCAAGGTTTTGTTAATTATATATAAAAATATTAGTGATACTATAACTGAAAATAA
 Y  L  T  L  T  K  N  I  I  Y  L  F  I  L  S  V  I  V  S  F  L
                   oc  N  Y  I  F  I  N  T  I  S  Y  S  F  I  F

           840                          860                          880
ATTCTACAGAAAAAACTCTAGTTATGTTCATAGTATCGTTTACTAACCTACTAGTTAAGTTACT
 N  am
 E  V  S  F  V  R  T  I  N  M  T  D  N  V  L  R  S  T  L  N  S

       900                          920                          940
TGCTGAGTTTTTTAAGTGAAAACTATAAGGTAACTTTATCACTTTATTCCATGTAACACTTCTA
 A  S  N  K  L  H  F  S  Y  P  L  K  I  V  K  N  W  T  V  S  R

   960                          980                          1000
ATGTTTTGTATTATTTTTTGACCTATATATCCAAGAATATAAGTAGAAACACCAGAAAATATTA
I  N  Q  I  I  K  Q  G  I  Y  G  L  I  Y  T  S  V  G  S  F  I  L

1020                         1040                         1060                         1080
AAGTCAGACCAAAACATATAATAATGATTACAATTTTATCTGTTGATAAGCTAGATTTGTTTAA
 T  L  G  F  C  I  I  I  I  V  I  K  D  T  S  L  S  S  K  N  L

              1100                         1120                         1140
GGCATTTCTAATTATTAAAGGAATGTATAATGAAAAACTAGTTCCAATCAAACTAAATATTAGT
 A  N  R  I  I  L  P  I  Y  L  S  F  S  T  G  I  L  S  F  I  L

          1160                         1180                         1200
CCAATACTTAAAAGTAGAGTGTTAGGTTTGGTTATTTTCCATAAATCATATAGACCTTTGATAA
G  I  S  L  L  L  T  N  P  K  T  I  K  W  L  D  Y  L  G  K  I  I
```

FIG. 9D

```
   S/D                      1240                          1260
TATCATCACCTTTTAAACTTTATATCATTAATATAATGTTTAGGAAAAGTAGAAGAAAATTACA
  D  D  G  K  L  S < epiY

 IR 1280                    1300                          1320
CTTTTGTAATTTTCTGAATATACATAGTATTTATTTTGGGGAGTACTAAAATAATAATTGAAA

1340    IR            1360            S/D      1380epiA >           1400
AGGGTTTTATAATCCTTTTTAATAAATTTTTAGGAGTGTTTAAAATGGAAGCAGTAAAAGAAAA
                                                     M  E  A  V  K  E  K

               1420                    1440                    1460
AAATGATCTTTTTAATCTTGATGTTAAAGTTAATGCAAAAGAATCTAACGATTCAGGAGCTGAA
  N  D  L  F  N  L  D  V  K  V  N  A  K  E  S  N  D  S  G  A  E

            1480                    1500                    1520
CCAAGAATTGCTAGTAAATTTATATGTACTCCTGGATGTGCAAAAACAGGTAGTTTTAACAGTT
 P  R  I  A  S  K  F  I  C  T  P  G  C  A  K  T  G  S  F  N  S

        1540                    1560                    1580
ATTGTTGTTAATTCAGAAGAATTAGATTGGCAGGGCTTCAATAGAGGCTCTGTCTTAATTTTGA
Y  C  C oc                                                 epiB >
```

FIG. 9E

```
S/D1600                        1620                           1640
GGTGAAATAGAATTGGATAATATATTTGTTCCATCGAATATATATATGGTAAGAACTCCTATAT
 G   E   I   E   L   D   N   I   F   V   P   S   N   I   Y   M   V   R   T   P   I

1660                      1680                       1700                       1720
TTTCAATTGAATTATATAATCAATTCTTAAAATCTGACAATATAGATTATGACTTAATTTTACA
F   S   I   E   L   Y   N   Q   F   L   K   S   D   N   I   D   Y   D   L   I   L   Q

                    1740                         1760                        1780
AAACGATATTTTTAAAGAATCTATAATGACAACGACATATAATCTTTATCAAAGTATTGGCAAA
  N   D   I   F   K   E   S   I   M   T   T   T   Y   N   L   Y   Q   S   I   G   K

              1800                         1820                        1840
ATAGACTGGGAAAAGGATAATAAAAAAACCAGAAATGTAAAAGAAAGTTTATTAAAATATCTCA
 I   D   W   E   K   D   N   K   K   T   R   N   V   K   E   S   L   L   K   Y   L

        1860                         1880                        1900
TAAGAATGAGTACTAGAAGTACACCATATGGAATGCTAAGCGGTGTAGCTTTAGGGGAATTTAG
I   R   M   S   T   R   S   T   P   Y   G   M   L   S   G   V   A   L   G   E   F   S

     1920                         1940                        1960
TGAAAATAATAATATTAAAATTAAGGACTCTTCGTTTCATAAAAAAGATGTAAAAATAGATGGG
  E   N   N   N   I   K   I   K   D   S   S   F   H   K   K   D   V   K   I   D   G

1980                        2000                        2020                        2040
CAATGGTTATATAAATTAGTCCATTATTTAGAAAGCGATTACACATATTATAAAGACAGTTTTG
 Q   W   L   Y   K   L   V   H   Y   L   E   S   D   Y   T   Y   Y   K   D   S   F
```

FIG.9F

```
                2060                          2080                          2100
TCATATGGAATCAACAAAATTATATTTATAACAATCGTTTATATTTAGATAATAATTCATCAAT
V   I   W   N   Q   Q   N   Y   I   Y   N   N   R   L   Y   L   D   N   N   S   S   I

          2120                          2140                          2160
CACTGAAAATAAAAGAAATGATGTATTATCTGTCAAATACAATTCTATATTAGTGTTTATACAT
  T   E   N   K   R   N   D   V   L   S   V   K   Y   N   S   I   L   V   F   I   H

  EcoRI 2180                          2200                          2220
GAGAATTCTAAAAAAAATATTACTTATGAAGAACTTGTACAATTGATATCTAGTAAGTACAGTA
 E   N   S   K   K   N   I   T   Y   E   E   L   V   Q   L   I   S   S   K   Y   S

     2240                          2260                          2280
TAGAAAATAAAGAAGAAGTAAAAGTATTTGTTCAAGAACTCATAAATAAAGAAATTATATTTTC
I   E   N   K   E   E   V   K   V   F   V   Q   E   L   I   N   K   E   I   I   F   S

2300                          2320                          2340                          2360
TGATTTGAGACCTACATTAGAGAATAAAAATCCTTTAGATTACATTATTAATAGTTTAAATCCA
  D   L   R   P   T   L   E   N   K   N   P   L   D   Y   I   I   N   S   L   N   P

                2380                          2400                          2420
AAAAATAGTTTAGTTGGAACACTTATTAATATTTCTAATGAAATTACAAAATATTCTAAAATGC
 K   N   S   L   V   G   T   L   I   N   I   S   N   E   I   T   K   Y   S   K   M
```

FIG. 9G

```
                2440                      2460                      2480
CTTTAGGAAAAGGAGAATATAAATATTTAGATATTGTTAATTTAATGTCACAATTATTTGTTTC
P  L  G  K  G  E  Y  K  Y  L  D  I  V  N  L  M  S  Q  L  F  V  S

          2500                      2520                      2540
TAAAAACTATTTGCAAATAGATACCTATATAGATTATTCAAGAAATGAATTAAAACAAAGTTTA
  K  N  Y  L  Q  I  D  T  Y  I  D  Y  S  R  N  E  L  K  Q  S  L

    2560                      2580                      2600
GCTGATAATATTAGTGAAGCAGCATATATTCTCTGGTTATTATCTCCTAATCATTTTGGTACAA
 A  D  N  I  S  E  A  A  Y  I  L  W  L  L  S  P  N  H  F  G  T

2620                      2640                      2660                      2680
AAACTATTAGGAATTATCACGAATTTTTTATGGATAAATATGGATTTGAACAACTAGTAAATTT
K  T  I  R  N  Y  H  E  F  F  M  D  K  Y  G  F  E  Q  L  V  N  L

                  2700                      2720                      2740
AAAGCAATTGCTCTCAGATATAAATGGATTTGGCTATCCCAAAAAAGACAGTTATAGTTTTTCT
  K  Q  L  L  S  D  I  N  G  F  G  Y  P  K  K  D  S  Y  S  F  S

            2760                      2780                      2800
AATAACATTGCATTTTTAAAAGAAAAGTATTTGCTTGCAATTCAAAATAACAGCCATATTGAAA
 N  N  I  A  F  L  K  E  K  Y  L  L  A  I  Q  N  N  S  H  I  E

          2820                      2840                      2860
TAACAGAAAACGACGTTAAAAATTTAGAAAAGAATAATACAGTTTCTAAAATCAATGCGCCTGT
I  T  E  N  D  V  K  N  L  E  K  N  N  T  V  S  K  I  N  A  P  V
```

FIG.9H

```
    2880                     2900                     2920
TTCAACTGAAATATATAGTGAGATATATTTTGGAAATTCAATAAAAGGTTATGAGGATTTTGCC
  S  T  E  I  Y  S  E  I  Y  F  G  N  S  I  K  G  Y  E  D  F  A

2940                     2960                     2980                  3000
GTGATAAGTCCAATATTAGGATCTTTTAATGCCGGTGCAACTTTTGGAAGGTTTACGGGAAATT
 V  I  S  P  I  L  G  S  F  N  A  G  A  T  F  G  R  F  T  G  N

                 3020                     3040                     3060
TCAATATAAAGAAAAAAAATCAATTACAAAAAGAAATAGTGCATCATTACAATAATTACATGAA
F  N  I  K  K  K  N  Q  L  Q  K  E  I  V  H  H  Y  N  N  Y  M  N

             3080                     3100                     3120
TGAAAATGGTTTAGAAATAAGCCAATTAAATGAAGGTCCTCTTAACTCAAGAAATGTAAATATT
  E  N  D  L  E  I  S  Q  L  N  E  A  P  L  N  S  R  N  V  N  I

         3140                     3160                     3180
TTGAATAATAATAGAATATATAATACTTGTTTAAATTTAAATTTACCTAAAAGTGATATAGATA
 L  N  N  N  R  I  Y  N  T  C  L  N  L  N  L  P  K  S  D  I  D

    3200                     3220                     3240
TAAATGACATATTTATTGGAGCTACATTTAACAAACTTTATCTATATTCTGAAAAACATGATTC
I  N  D  I  F  I  G  A  T  F  N  K  L  Y  L  Y  S  E  K  H  D  S
```

FIG. 9I

```
3260                          3280                          3300                          3320
AAGAATTGTATTCGTATCTAATTCAATGTTTAATTATGAGTTTGGATCTGAATTATACAAATTT
  R   I   V   F   V   S   N   S   M   F   N   Y   E   F   G   S   E   L   Y   K   F

                        3340                          3360                          3380
TTAAGAGAAATTTCATTTGAAAAAACAAAATTTATACAACCTATAACTGAAGAAGGCATTGACT
 L   R   E   I   S   F   E   K   T   K   F   I   Q   P   I   T   E   E   G   I   D

                  3400                          3420                          3440
CATTACCTTTTTGTCCAAGAATTATTTATAAAAATATTATTTTAAAACCAGCTACTTGGAAAAT
S   L   P   F   C   P   R   I   I   Y   K   N   I   I   L   K   P   A   T   W   K   I

            3460                          3480                          3500
AAATTCAGAAATGTTTTCTGAAACTGAAAATTGGTTAAATAGGTTCGCAACTATTAGAGAAAAA
  N   S   E   M   F   S   E   T   E   N   W   L   N   R   F   A   T   I   R   E   K

      3520                          3540                          3560
TGGCATATTCCAAAAGATGTAATTATTGCTTTTGGAGATAATCGATTGCTATTAAATTTATTAA
 W   H   I   P   K   D   V   I   I   A   F   G   D   N   R   L   L   L   N   L   L

3580                          3600                          3620                          3640
ATGACAAGCATCTCATTATACTAAAAAAAGAACTAAAAAAACATGGTAGGATTCGAATATTAGA
N   D   K   H   L   I   I   L   K   K   E   L   K   K   H   G   R   I   R   I   L   E

HindIII                 3660                          3680                          3700
AAGCTTTATCAATGAATCTAATAATGAGAGAATGTTAGAAATTGTTACGCCATTATATAAAAAA
  S   F   I   N   E   S   N   N   E   R   M   L   E   I   V   T   P   L   Y   K   K
```

FIG.9J

```
                3720                                    3740                                    3760
ACTAGTTTAAAAGAACAATCTTTCATTATACCTAAAAATAGAAATAAGCACTTCAATAATCTTA
 T  S  L  K  E  Q  S  F  I  I  P  K  N  R  N  K  H  F  N  N  L

        3780                                    3800                                    3820
AAGATTGGTTTTCAATTCATTTAAGTATTCCTAAAACATACCAAGATAATTTTATTCAAGATTA
K  D  W  F  S  I  H  L  S  I  P  K  T  Y  Q  D  N  F  I  Q  D  Y

    3840                                    3860                                    3880
TCTATTACCATTTATAACGGAATTAAAAGTTAATAATTTTATTAATAAATTTTTTACATAAAA
  L  L  P  F  I  T  E  L  K  V  N  N  F  I  N  K  F  F  Y  I  K

3900                                    3920                                    3940                                    3960
TTTAAAGAAGATGAAGATTTTATAAAATTAAGATTATTAAGAGAAGATGAAGATTATTCTCAAA
 F  K  E  D  E  D  F  I  K  L  R  L  L  R  E  D  E  D  Y  S  Q

                3980                                    4000                                    4020
TTTATTCTTTCATAAAAAATTGGAAAGATTATTGCTTATTAAATAGTGAATTATATGACTATTC
I  Y  S  F  I  K  N  W  K  D  Y  C  L  L  N  S  E  L  Y  D  Y  S

            4040                                    4060                                    4080
TATAGTTGATTATGTTCCTGAAGTATATAGATATGGTGGTCCACACGTAATTGAAGATATTGAG
  I  V  D  Y  V  P  E  V  Y  R  Y  G  G  P  H  V  I  E  D  I  E
```

FIG. 9K

```
       4100                   4120                    4140
AATTTTTTTATGTATGATAGTCTATTATCAATAAATATAATACAATCAGAGTTCAAAATTCCAA
 N  F  F  M  Y  D  S  L  L  S  I  N  I  I  Q  S  E  F  K  I  P

   4160                   4180                    4200
AAGAATTTATCGTTGCTATATCAATAGATTTTTATTAGATTATTTAGAAATTAATAAAAGTGA
K  E  F  I  V  A  I  S  I  D  F  L  L  D  Y  L  E  I  N  K  S  E

4220                 4240                    4260                4280
GAAAGAAGAAATTTTAATTAATAATGCGGAAGATTTATATCGTAGTAATGACATAAGAGAATAT
  K  E  E  I  L  I  N  N  A  E  D  L  Y  R  S  N  D  I  R  E  Y

                 4300                    4320                 4340
AAAAATTTATTAGCTAAACTTACCAATCCTAAAAATGACTATGAAATTTTAAAAAAAGAATTTC
 K  N  L  L  A  K  L  T  N  P  K  N  D  Y  E  I  L  K  K  E  F

             4360                    4380                 4400
CGAATCTTCATGAATTTCTATTTAATAAAATTAGTATTTTAGAAAATCTTAAAAAGACACTACA
P  N  L  H  E  F  L  F  N  K  I  S  I  L  E  N  L  K  K  T  L  Q

  HindIII                    S/D_ epiC >             4460
AAAAAGCTTATATACTTCACGTTCTAGGATAATTGGCAGTTTTATACACATGCGTTGTAATAGA
  K  S  L  Y  T  S  R  S  R  I  I  G  S  F  I  H  M  R  C  N  R
                                [L] A  V  L  Y  T  C  V  V  I  E
```

FIG. 9L

```
    4480                  4500                  4520
ATATTCGGTATTAATCCTGAAAAAGAAAAATTTGTTTTATCTATTTTTAATGAAATTACAAAAA
 I  F  G  I  N  P  E  K  E  K  F  V  L  S  I  F  N  E  I  T  K
  Y  S  V  L  I  L  K  K  K  N  L  F  Y  L  F  L  M  K  L  Q  K

4540                  4560                  4580                  4600
CTAAAAAATATTGGGATGGTTGTGATTAATATTAATAACATTAAAAAAATTTTAGAAAATAAAA
T  K  K  Y  W  D  G  C  D oc       oc oc
 L  K  N  I  G  M  V  V  I  N  I  N  N  I  K  K  I  L  E  N  K

             4620                  4640                  4660
TCACCTTTTTGTCTGACATTGAAAAAGCTACATATATTATAGAAAATCAAAGTGAGTATTGGGA
I  T  F  L  S  D  I  E  K  A  T  Y  I  I  E  N  Q  S  E  Y  W  D

         4680                  4700                  4720
TCCTTATACTCTATCTCATGGTTATCCAGGTATAATACTTTTTTTAAGCGCATCAGAAAAAGTA
  P  Y  T  L  S  H  G  Y  P  G  I  I  L  F  L  S  A  S  E  K  V

     4740                  4760                  4780
TTTCATAAAGATTTAGAAAAAGTAATACATCAATATATTAGAAAACTAGGCCCTTATTTAGAAA
 F  H  K  D  L  E  K  V  I  H  Q  Y  I  R  K  L  G  P  Y  L  E

    4800                  4820                  4840
GTGGTATTGATGGATTTTCACTTTTTAGTGGTCTTTCCGGAATTGGATTTGCGCTAGACATTGC
S  G  I  D  G  F  S  L  F  S  G  L  S  G  I  G  F  A  L  D  I  A
```

FIG. 9M

```
4860                4880                4900                4920
GTCTGATAAACAGTACTCTTATCAAAGTATCTTAGAACAAATTGATAATTTACTTGTTCAATAT
  S  D  K  Q  Y  S  Y  Q  S  I  L  E  Q  I  D  N  L  L  V  Q  Y

                4940                4960                4980
GTTTTTGATTTTTTAAATAACGATGCATTGGAAGTAACCCCTACTAACTATGATATAATACAAG
 V  F  D  F  L  N  N  D  A  L  E  V  T  P  T  N  Y  D  I  I  Q

            5000                5020                5040
GATTTTCTGGTATAGGAAGGTACTTGTTAAATAGAATATCGTATAATTATAATGCAAAAAAAGC
G  F  S  G  V  G  R  Y  L  L  N  R  I  S  Y  N  Y  N  A  K  K  A

         5060                5080                5100
ATTAAAGCATATACTTAATTACTTCAAAACAATTCATTACTCTAAAGACAATTGGTTAGTTTCA
  L  K  H  I  L  N  Y  F  K  T  I  H  Y  S  K  D  N  W  L  V  S

    5120                5140                5160
AATGAACATCAATTTTTAGATATAGATAAGCAAAATTTTCCGTCAGGAAATATAAATTTAGGAT
 N  E  H  Q  F  L  D  I  D  K  Q  N  F  P  S  G  N  I  N  L  G

5180                5200                5220                5240
TAGCGCATGGTATTTTAGGTCCTCTATCATTAACAGCTTTGAGTAAAATGAATGGGATTGAAAT
L  A  H  G  I  L  G  P  L  S  L  T  A  L  S  K  M  N  G  I  E  I

                5260                5280          EcoRI
CGAAGGCCATGAAGAGTTTTTACAAGACTTCACTTCATTTTTGCTCAAACCTGAATTCAAAAAT
  E  G  H  E  E  F  L  Q  D  F  T  S  F  L  L  K  P  E  F  K  N
```

FIG. 9N

```
          5320                          5340                          5360
AATAATGAATGGTTCGATCGCTATGATATATTAGAAAATTATATACCTAATTATTCCGTCAGAA
 N  N  E  W  F  D  R  Y  D  I  L  E  N  Y  I  P  N  Y  S  V  R

      5380                          5400                          5420
ACGGTTGGTGTTACGGTGATACAGGGATTATGAATACATTACTTTTGTCTGGTAAAGCCTTAAA
N  G  W  C  Y  G  D  T  G  I  M  N  T  L  L  L  S  G  K  A  L  N

  5440                          5460                          5480
TAATGAAGGCTTAATTAAAATGTCTAAAAATATTTTAATTAACATAATAGATAAGAATAATGAT
  N  E  G  L  I  K  M  S  K  N  I  L  I  N  I  I  D  K  N  N  D

5500                          5520                          5540                    5560
GATTTAATCAGTCCAACCTTCTGTCACGGACTAGCATCGCACTTAACCATTATTCATCAAGCGA
 D  L  I  S  P  T  F  C  H  G  L  A  S  H  L  T  I  I  H  Q  A

                5580                          5600                          5620
ATAAATTCTTTAATCTATCTCAAGTAAGCACATATATCGATACCATTGTCAGAAAAATTATTAG
N  K  F  F  N  L  S  Q  V  S  T  Y  I  D  T  I  V  R  K  I  I  S

          5640                          5660                          5680
TCATTATTCTGAAGAAAGTAGTTTTATGTTCCAAGACATAGAGTACTCATACGGACAAAAAATT
  H  Y  S  E  E  S  S  F  M  F  Q  D  I  E  Y  S  Y  G  Q  K  I
```

FIG. 90

```
        5700   EcoRI        5720                 5740
TATAAAAACAAAGTGGAATTCTAGAGGGTGAATTAGGTGTTCTTTTAGCTTTACTAGATTATA
 Y  K  N  K  V  G  I  L  E  G  E  L  G  V  L  L  A  L  L  D  Y

    5760                 5780                 5800          S/D
TTGATACACAAAACCAATCAAGGAAAAATTGGAAAAATATGTTTTTAATAACATAATAGGAGGA
I  D  T  Q  N  Q  S  R  K  N  W  K  N  M  F  L  I  T oc

5820    epiD >     5840                 5860                 5880
ATAAGATATGTATGGAAAATTATTGATATGCGCTACAGCATCGATAAATGTAATTAATATTAAT
        M  Y  G  K  K  L  L  C  A  T  A  S  I  N  V  I  N  I  N

              5900                 5920                 5940
CACTACATAGTTGAGTTAAAGCAACATTTTGATGAAGTTAATATATTATTTAGTCCTAGTAGTA
 H  Y  I  V  E  L  K  Q  H  F  D  E  V  N  I  L  F  S  P  S  S

          5960                 5980                 6000
AAAATTTTATAAATACTGATGTTCTCAAGTTATTTTGTGATAACTTGTACGATGAAATTAAAGA
K  N  F  I  N  T  D  V  L  K  L  F  C  D  N  L  Y  D  E  I  K  D

      6020                 6040                 6060
TCCTCTTTTAAATCATATCAATATTGTAGAAAATCATGAATATATTTTAGTATTACCTGCATCA
  P  L  L  N  H  I  N  I  V  E  N  H  E  Y  I  L  V  L  P  A  S

    6080                 6100                 6120
GCAAATACTATTAATAAAATAGCTAATGGTATATGTGATAATCTTTTAACTACTGTATGTTTAA
 A  N  T  I  N  K  I  A  N  G  I  C  D  N  L  L  T  T  V  C  L
```

FIG. 9P

```
  EcoRV          6160                6180                6200
CCGGATATCAAAAATTATTTATATTTCCAAATATGAACATAAGAATGTGGGGAAATCCATTTTT
T  G  Y  Q  K  L  F  I  F  P  N  M  N  I  R  M  W  G  N  P  F  L

                6220                6240                6260
ACAAAAAAATATTGATTTACTTAAAAATAATGATGTGAAAGTGTATTCCCCTGATATGAATAAA
 Q  K  N  I  D  L  L  K  N  N  D  V  K  V  Y  S  P  D  M  N  K

            6280                6300                6320
TCATTCGAAATATCTAGTGGCCGTTACAAAAACAATATCACAATGCCTAATATTGAAAATGTAC
 S  F  E  I  S  S  G  R  Y  K  N  N  I  T  M  P  N  I  E  N  V

        6340                6360  Terminator   6380
TAAATTTTGTATTAAATAACGAAAAAAGACCTTTGGATTAACAAAGGTCTTTTCTAATTAAAAT
L  N  F  V  L  N  N  E  K  R  P  L  D oc
                                      oc C  L  D  K  R  I  L  I

    6400                6400                6440
TTTATATCCGAGTTTACGTTCATTAATAATTTCTATCTCTTTACAATTTTTTAAACTATCCCTT
 K  Y  G  L  K  R  E  N  I  I  E  I  E  K  C  N  K  L  S  D  R

6460             6480                6500                6520
AATCGATGGATATATACATTTATTGTATTAGAATCAACAAAGTCTTCTGTATCCCACACTCCCT
L  R  H  I  Y  V  N  I  T  N  S  D  V  F  D  E  T  D  W  V  G  K
```

FIG. 9Q

```
                  6540                     6560                    6580
TTTTTAATTCCTCTTTTGATACATATCTTCCAAGATTAATATATAAGCACCGTAGAATTTTTAA
  K  L  E  E  K  S  V  Y  R  G  L  N  I  Y  L  C  R  L  I  K  L

              6600                     6620                    6640
TTCTATATTAGAAAGATTAACTAAGTAATTATTAAACACAAATTGATGGTTTTCAAAGTCTATA
 E  I  N  S  L  N  V  L  Y  N  N  F  V  F  Q  H  N  E  F  D  I

    6660                     6680                    6700
AAATCATCATTAACATATTTAATATACTTTTTTATTTCATTTAAAATTCTACATAATATTAAAC
F  D  D  N  V  Y  K  I  Y  K  K  I  E  N  L  I  R  C  L  I  L  S

    6720                  6740                    6760
TTTTGCTTTCATTATTTTTATAATATATAAATCTATGCCTAAACTATAAAAATAACACTTCCT
  K  S  E  N  N  K  I  I  Y  L  D  I  G  L  S  Y  F  Y  C  K  R

6780                  6800                     6820                     6840
ACTATAGCTAGTATTACCTGTTATTATAACTATTGGAATTTTTCCTATAAATTCTTTTAAAAAC
 S  Y  S  T  N  G  T  I  I  V  I  P  I  K  G  I  F  E  K  L  F

                  6860                     6880                    6900
GTATAATACTCATCAAACTTTTCATACACAATTATAAAATTTGGGTCTATATTTGAAGAATTAA
T  Y  Y  E  D  F  K  E  Y  V  I  I  F  N  P  D  I  N  S  S  N  I

              6920                     6940                    6960
TTGTAATTCTTCTATCTAATTCTAAAATACTTTCAATAAGAATAGAATCTACCTCACCGACAAT
  T  I  R  R  D  L  E  L  I  S  E  I  L  I  S  D  V  E  G  V  I
```

FIG. 9R

6980 S/D 7000 7020
ATTAATAGAAATCATTTTATTCCCTTCATTCTTTAAGTAATTTGTATACGTCTAGTTTTCCATT
N I S I M < epiQ op E K L L K Y V D L K G N 7040 7060 7080
ACCATAATGTTTTTTATCCATATATTTTTCTTTTTCTATCCCTTTTTTCTTAAATAACTCTATA
G Y H K K D M Y K E K E I G K K K F L E I 7100 7120 7140 7160
GCTGTTTCGGGTTGGTCTTTTAATTGATACTTATCAATTTCTAGTGCTAAAGCTCCAGAAACCT
A T E P Q D K L Q Y K D I E L A L A G S V K 7180 7200 7220
TGGGTGCAGCAAGTGATGTCCCTGATTGATATATGTATCTTCCATTAGAAGAAGTACTTAAAAC
P A A L S T G S Q Y I Y R G N S S T S L V 7240 7260 7280
ACTTTGTTTTTGCATATATCCTTTTTCTAACCAAGCATCTTTTCCATACTTATCTAAAAGTTTA
S Q K Q M Y G K E L W A D K G Y K D L L K 7300 7320 7340
TAAGAACCTCCTATCGTCATTAAATCTATAAAATTATTTCCATAATTAGAAAACTCAGAAATAT
Y S G G I T M L D I F N N G Y N S F E S I Y

FIG. 9S

```
    7360        BamHI_  7380                    7400
AATCATTATCATCGATGGATCCTACAGTCATAACATTATTTAGATTTGCTGGCTATCATATAC
 D  N  D  D  I  S  G  V  T  M  V  N  N  L  N  A  P  S  D  Y  V

7420                7440                7460                7480
CTTTTTTGATGTTTTAGAATTTAGATTTCTTTTTTTATTTATTTCTTTTACTTTTTTTACATTG
 K  K  S  T  K  S  N  L  N  R  K  K  N  I  E  K-V  K  K  V  N

                    7500                7520                7540
ATACCGTCATTACCCACAGCTGCAACAACAATACTACCTTTTTTTTGAGCATAGTTTATAGCTT
I  G  D  N  G  V  A  A  V  V  I  S  G  K  K  Q  A  Y  N  I  A  K

                7560                7580                7600
TCTGTAGTGCATCGTAATCAACTTTTTCATCATCTCTTAATTTTTTTTTATTTTGATTATCTTT
 Q  L  A  D  Y  D  V  K  E  D  D  R  L  K  K  K  N  Q  N  D  K

            7620                7640                7660
AATTAAATAATTTCCTAAACTAACGTTGATTACATCATTGTCATCATTTGCTGCATCAATAATT
 I  L  Y  N  G  L  S  V  N  I  V  D  N  D  D  N  A  A  D  I  I

    7680                7700                7720
CCTTTAGATACCCAAAGCATTTCACTTTTCTTTGAGCCAAATACTCGGTATACATTCATCTCTA
G  K  S  V  W  L  M  E  S  K  K  S  G  F  V  R  Y  V  N  M  E  V

7740                7760                7780                7800
CTCCAGGGTTTACACCTTTTAAATTACCGTTTGCTCCTATTTGTCCTGCTACTAATGTACCATG
 G  P  N  V  G  K  L  N  G  N  A  G  I  Q  G  A  V  L  T  G  H
```

FIG. 9T

```
                    7820                    7840                    7860
ATTCAATTTATCTTCTTCAAAATTTTTATTTCCTGATTCATCGTTTTCGCTACCTCTAAAACCA
 N  L  K  D  E  E  F  N  K  N  G  S  E  D  N  E  S  G  R  F  G

                 7880                    7900                    7920
TTTTTAGGCACTTCATTAACTATCTTATTTATACTCTTTAAATCTGTATGACTACTATTCACAC
N  K  P  V  E  N  V  I  K  N  I  S  K  L  D  T  H  S  S  N  V  G

              7940                    7960                    7980
CAGAATCTACTAAAGCAACTTTTGCTTTTTTTCTATCTGGACTTAGCTTATAACTTTTACCTTC
  S  D  V  L  A  V  K  A  K  K  R  D  P  S  L  K  Y  S  K  G  E

    8000                    8020                    8040
ATTTGTTATTTTTCGCATATCCCATTGTCTGTCAAATAAATCATGGCTGCCATTTTTTTTATTA
 N  T  I  K  R  M  D  W  Q  R  D  F  L  D  H  S  G  N  K  K  N

8060                    8080                    8100                    8120
TTTAAATTTTTTCCTGTCTTTACAGATTTTTCAACTACACAAGTGGAACAGGTAGGATTTACAA
N  L  N  K  G  T  K  V  S  K  E  V  V  C  T  S  C  T  P  N  V  F

                    8140                    8160                    8180
ACTTGACGTTTTTATTACTCTTTATTAGTGAATTTAATTTTGATTTGCTAGTTTTAATTTGTGC
  K  V  N  K  N  S  K  I  L  S  N  L  K  S  K  S  T  K  I  Q  A
```

FIG. 9U

```
            8200          HindII 8220                    8240
TGTATGTAGTTCAGGAATTTTATAAGTTAACTCGATATTTTTTGTTTAATGGATTCTTTAAAA
 T  H  L  E  P  I  K  Y  T  L  E  I  N  K  Q  K  I  S  E  K  F

       8260                 8280                 8300
GTTTTTGCATTATCATATTCAACACTATAATAACTTAATTCTTCATTTAGTGAACTTCCAAAAG
T  K  A  N  D  Y  E  V  S  Y  Y  S  L  E  E  N  L  S  S  G  F  A

   8320                 8340                 8360
CATACTCATTTTGCAAAAAAACTAATGACAATATTAAAAAAACAATGAAAAATTTAAATTTGTT
  Y  E  N  Q  L  F  V  L  S  L  I  L  F  V  I  F  F  K  F  K  N

8380     S/D       8400                 8420                 8440
CATATAGCACCTCTAACATATTATTTATATTAAACATTAATTTAACACTTATGTTTTTACTTTT
 M < epiP

                 8460                 8480                 8500
TTATTTATATTATCTTTAATAATGTTCTGTTGCAAGATGAAAAATACGAGGTATCAAAGTACCG

             8520                 8540                 8560
ATACAGCGAGTATTACACTCAATTAATTAAAAATAAAATATGTTGTGATTAAAATTTATTTTAT

         8580                 8600            KpaII
AAAAGTATGGGCAATTTATTATTATTCAAGTTAAAACAAAGAGTCCGGGACATAAAGTTTCAGC

     8640                 8660                 8680
CTCTTCGTCCTAATTACCAAAAAACTTACTCCAAAATCCTTTTTTAGATTGGTTTTTTCTAATT

8700
TTTT
```

FIG. 11A

```
Active site I:
                                           *
EPIP      130 EGKSYKLSPDRKKAKVALVDSGVNSSHTDLKSINKIVNEVP 170
                             ..::::.::::..::::.::.
SUBSI     119 APALHSQGYTGSNVKVAVIDSGIDSSHPDLNVRGGASFVPS 159
                            :. :::..:.:  ..::.:::.
ISPI       31 APEMWAKGVKGKNIKVAVLDTGCDTSHPDLKNQIIGGKNFS  71
                              ::.:.::.::.:.:.::
SUMYTV     19 QAPQAWDIAEGSGAKIAIVDTGVQSNHPDLAGKVVGGWDFV  59
                                           *
```

FIG. 11B

```
Active site II:
                                            *
EPIP   170 PKNGFRGSENDESGNKNFEEDKLNHGTLVAGQIGANGNLKGVNPGVEMNVY 220
           :. . ::...  ....:  .:  .::: ::: :.: .:  ::
SUBSI  146 PDLNVRGGASFVPSETNPYQDGSSHGTHVAGTIAALNNSIGVLGVSPSASL 196
                   .:..:...  .:  .::: ::: :.::..  :.
ISPI   163 QIIGGKNFSDDDGGKEDAISDYNGHGTHVAGTIAANDSNGGIAGVAPEASL 113
                                 :::  ::
SUMYTV 67                  NGNGHGTHCAGIAAAVTNNST                 87
                                *
Active site III:
                                *
EPIP       380 YMQKQSVLSTSSNGRYIYQSGTSLAAPKVSGALALEIDKYQ 420
                   :. :: ..: :   .:::.:.:.:.:: :: ..:
SUBSI      305 MAPGVSIQSTLPGGTYGAYNGTSMATPHVAGAAALILSKHP 345
                   ...::: .: .:   .::::::.:::::::: :..:.
ISPI       224 VAPGENILSTLPNKKYGKLTGTSMAAPHVSGALAL-IKSYE 263
                    . :: ... :    ::::.:.:.:.:. .:
SUMYTV     203 AAPGSWIYSTYPTSTYASLSGTSMATPHVAGVAGLLASQGR 243
                                *
```

FIG. 12

```
                10        20        30        40        50        60
EPIQ   MISINIVGEVDSILIESILELDRRITINSSNIDPNFIIVYEKFDEYYTFLKEFIGKIPIV
                                                                ::.:
PHOB   VLEQNGFQPVEAEDYDSAVNQLNEPWPDLILLDWMLPGGSGIQFIKHLKRESMTRDIPVV
                30        40        50        60        70        80
                70        80        90       100       110
EPIQ   IITGNTSYSRKCYFYSLGIDLYIIKNNESKSLILCRILNEIKKYIKYVNDDFID-----F
       ..:.... . .    . : : ::.:  ..:.:.  :: . ...    . .. :.     .
PHOB   MLTARGEEEDRVRGLETGADDYITKPFSPKELV-ARIKAVMRRISPMAVEEVIEMQGLSL
                90       100       110       120       130
            120       130       140       150       160       170
EPIQ   E--NHQFVFNNYLVNLSNIELKILRCLYINLGRYVSKEELKKGVWDTEDFVDSNTINVYI
       .  .:. . ..   .... .:.:.:. . .. .:  :.:.: . ::.:. .:...:..:.:
PHOB   DPTSHRVMAGEEPLEMGPTEFKLLHFFMTHPERVYSREQLLNHVWGTNVYVEDRTVDVHI
                150       160       170       180       190
            180       190       200
EPIQ   HRLRDSLKNCKEIEIINE-RKLGYKILIRKDLC
       .::::..:..   .   .... :  ::.. .:
PHOB   RRLRKALEPGGHDRMVQTVRGTGYRFSTRF
     200       210       220
```

BIOSYNTHETIC PROCESS FOR THE PREPARATION OF CHEMICAL COMPOUNDS

CROSS-REFERENCE TO RELATED APPLICATIONS

The present application is a divisional of application Ser. No. 08/392,625, filed Feb. 22, 1995, pending, which is a continuation of application Ser. No. 07/876,791, filed Apr. 30, 1992, abandoned, which is a continuation of application Ser. No. 07/784,234, filed Oct. 31, 1991, abandoned, which is a continuation-in-part of application Ser. No. 07/353,590, filed May 18, 1989, abandoned.

FIELD OF THE INVENTION

This invention relates to the biosynthesis of chemical compounds, and in particular to the biosynthesis of chemical compounds containing dehydroamino acid residues and/or thioether bridges. The invention also relates to the use of recombinant genetics to prepare enzymes involved in the biosynthesis of such chemical compounds.

BACKGROUND OF THE INVENTION

Some polypeptide antibiotics such as nisin, subtilin, duramycin, cinnamycin, ancovenin, Ro 09-0198 and epidermin contain dehydroamino acids and lanthionine bridges. These polypeptides are produced by various respective strains of microorganism. Nisin for example can be produced by cultivating strains of *Streptococcus lactin*, and subtilin by cultivation of *Bacillus subtilis.*

The genetic basis for the biosynthesis of these antibiotics has not, hitherto, been elucidated. Thus, it has not been known, for example, whether biosynthesis of such antibiotics and, in particular, the formation of the unusual amino acids found therein occurs via ribosomal synthesis or via multi-enzyme complexes.

It addition it was not know whether the precursor proteins of such antibiotics were coded by distinct structural genes or were the degradation products of larger proteins.

In the course of work carried out to establish the structural gene of epiderm, we have been able to establish that surprisingly the above mentioned antibiotics, in particular epidermin, are each coded by a distinct structural gene, and that processing of a presequence polypeptide is carried out by an enzymatic complex which effects formation of dehydroamino residues and/or thioether bridges.

Furthermore, the multi-enzyme complex may be involved in the secretion of the protein through the cell membrane into the culture supernatant, as well as processing a prepolypeptide. In this connection, such activity may be associated with a pre-sequence possessed by the prepolypeptide, e.g., as in the case of the −30 to −1 sequence of pre-epidermin as described below.

DESCRIPTION OF THE DRAWINGS

FIGS. 1A and 1B depict the nucleotide sequence of the epidermin structural gene (epi A) and the deduced amino acid sequence of pre-epidermin. A Shine-Dalgarno sequence is boxed and the proteolytic cleavage site at which the propeptide is processed is indicated by an arrow. Inverted repeats are underlined and potential stop codons are noted as am (amber) and oc (ochre).

FIGS. 5A and 5B depict examples of unusual amino acids which are found in lanthione antibiotics and which can be formed in peptide products using the method of this invention.

FIG. 7B depicts the elution pattern of a standard containing gallidermin. Gallidermin is eluted at 7.54 minutes.

8A: a restriction map of episome pTü32, and

8B: a restriction map of the 13.5 kb BglII fragment of pT ü32. The filled arrow corresponds to the epiA structural gene. Open arrows represent reading frames epiB, C, D, P and Q.

8C: Southern hybridization of pTü32 digested with different restriction enzymes (EcoRI, EcoRV, BglII, SphI) using a 15-mer oligonucleotide (5'CACATCCAGGAGTAC-3') specific of epiA.

FIGS. 9A–9U are corresponds to the nucleotide sequence of SEQ ID NO:16 as an 8700 nucleotide sequence of the BglII/HpaII fragment of pTü32 containing reading frames epiA (nucleotides 1381–1536 of SEQ ID NO:16), epiB (nucleotides 1593–4662 of SEQ ID NO:16), epiC (nucleotides 4441–5805 of SEQ ID NO:16), epiD (nucleotides 5824–6366 of SEQ ID NO:16), epiP (nucleotides complementary to the DNA sequence 8379–6996 of SEQ ID NO:16), epiQ (nucleotides complementary to the DNA sequence 6983–6369 of SEQ ID NO:16); epiY (nucleotides complementary to the DNA sequence 1227–784 of SEQ ID NO:16); epiY' (nucleotides complementary to the DNA sequence 1226–831 of SEQ ID NO:16); and epiY" (nucleotides complementary to the DNA sequence 827–3 of SEQ ID NO:16) and the deduced amino acid sequences: EpiY" as amino acids 275–1 (SEQ ID NO:17) of FIG. 9), encoded by nucleotides complementary to nucleotides 827–3 of FIG. 9 (SEQ ID NO:16); EpiY as 148 amino acids (SEQ ID NO:18) encoded by 444 nucleotides complementary to 1227–784 of FIG. 9 (SEQ ID NO:16); EpiA as 52 amino acids (SEQ ID NO:19) encoded by 156 nucleotides 1381–1536 of FIG. 9 (SEQ ID NO:16); EpiB as 990 amino acids (SEQ ID NO:20) encoded by 2970 nucleotides 1593–4562 of FIG. 9 (SEQ ID NO:16); EpiC as 455 amino acids (SEQ ID NO:21) encoded by 1365 nucleotides 4441–5805 of FIG. 9 (SEQ ID NO:16); EpiD as 181 amino acids (SEQ ID NO:22) encoded by 543 nucleotides 5824–6366 of FIG. 9 (SEQ ID NO:16); EpiP as 461 amino acids (SEQ ID NO:24) encoded by 1383 nucleotides complementary to 8379–6996 of FIG. 9 (SEQ ID NO:16); and EpiQ as 205 amino acids (SEQ ID NO:23) encoded by 615 nucleotides complementary to 6983–6369 of FIG. 9 (SEQ ID NO:16) of the respective proteins. S/D sequences and termination structures are overlined. IR indicates inverted repeats. The start of the open reading frames of epiY, epiA, epiB, epiC, epiD, epiQ and epiP are indicated by bold letters. The N-terminal amino acid residues (possible translational start sites) are boxed.

Figure 10:
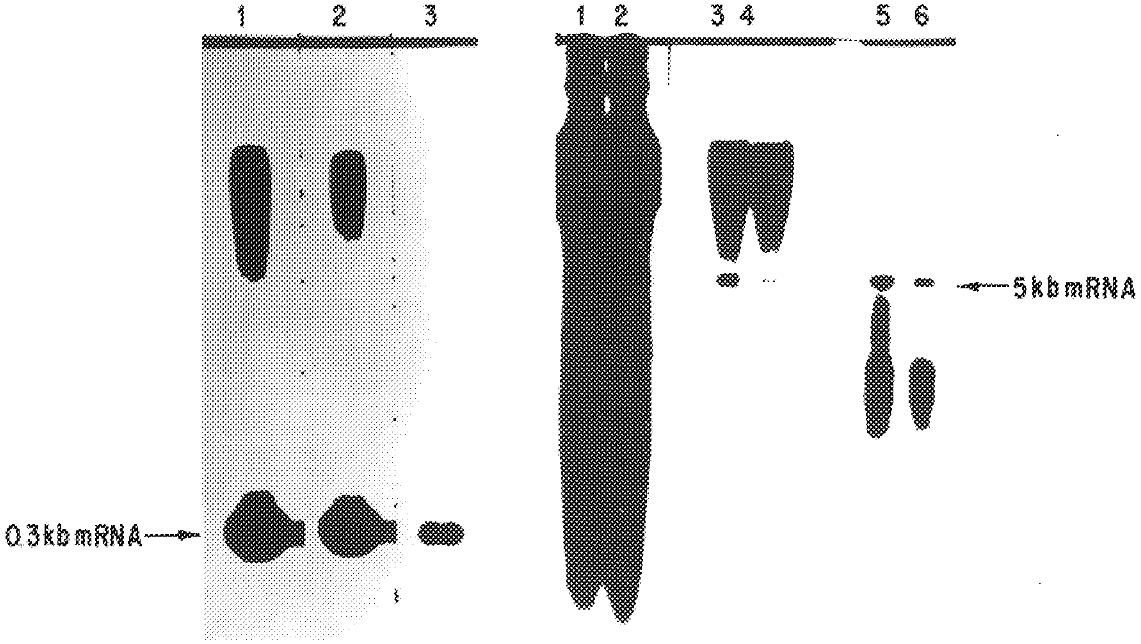

FIG. 10 shows the results of a Northern blot analysis of epiA (10A) and epiB (10B) expression in *S. epidermidis*, in which total RNA (40 $\mu$g, lanes 1, 3, and 5, or 20 $\mu$g, lanes 2, 4, and 6) were separated on 1.2% agarose gels and hybridization was performed with an antisense RNA probe (SP6 transcript. Filters were washed with increasing stringency; lanes 1, 2:1×SSC, 0.1% SDS, exposition time, 4 h, lanes 3, 4:0.5×SSC, 0.1% SDS, exposition time 16 h; lanes 5,6:0.1×SSC, 0.1% SDS, exposition time, 3 days). The positions of 235 and 165 RNAs were used as a size standards.

FIGS. 11A and 11B show sequence homologies between EpiP and different serine proteases at the active sites (SUBSI, subtilisin I168 precursor of *B. subtilis* (Terzaghi et al., *Appl. Microbiol.* 29: 807–813 (1975); ISPI major ISPI intracellular serine protease from *B. subtilis* (Maniatis et al., *Molecular Cloning. A Laboratory Manual*; 2nd ed. Cold Spring Harbour Laboratory Press (1990); SUMYTV, thermitase from *Thermoactinomyces vulgaris* (Stahl et al., *J. Bacteriol* 158: 411–418 (1984)). Three active sites are compared. In active site I, amino acids 130–170 of EPIP (SEQ ID NO:25) are compared to amino acids 119–159 of SUBSI (SEQ ID NO:26); amino acids 31–71 of ISPI (SEQ ID NO:27); and amino acids 19–59 of SUMYTV (SEQ ID NO:28). In active site II, amino acids 170–220 of EPIP (SEQ ID NO:29) are compared to amino acids 146–196 of SUBSI (SEQ ID NO:30); amino acids 163–213 of ISPI (SEQ ID NO:31); and amino acids 67–87 of SUMYTV (SEQ ID NO:32). In active site III, amino acids 380–420 of EPIP (SEQ ID NO:33) are compared to amino acids 305–345 of SUBSI (SEQ ID NO:34); amino acids 224–263 of ISPI (SEQ ID NOS:35–36); and amino acids 203–243 of SUMYTV (SEQ ID NO:37). The strongly conserved asparagine (asp), histidine (his), and serine (ser) residues are marked by asterisks. Similar amino acid residues are indicated by points and identical amino acid residues by colons.

FIG. 12 shows sequence homologies between epiQ and PhoB (Makino et al, *J. Mol. Biol.* 190:37–44 (1986)). Similar amino acid residues are indicated by points and identical amino acid residues by colons. Amino acids 1–205 (1–115 as SEQ ID NO:38 and 116–205 as SEQ ID NO:41) of EpiQ (PIQ) are compared to amino acids 21–229 (21–113 as SEQ ID NO:39 and 114–229 as SEQ ID NO:40) of PhoB.

Figure 13A:
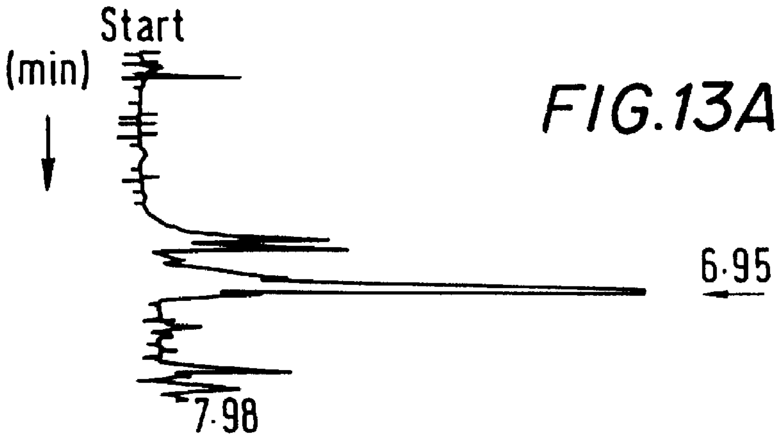
Figure 13B:
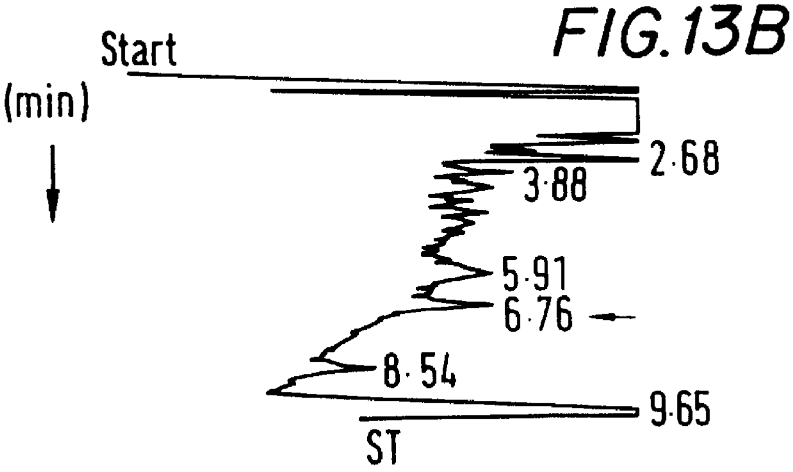
Figure 13C:
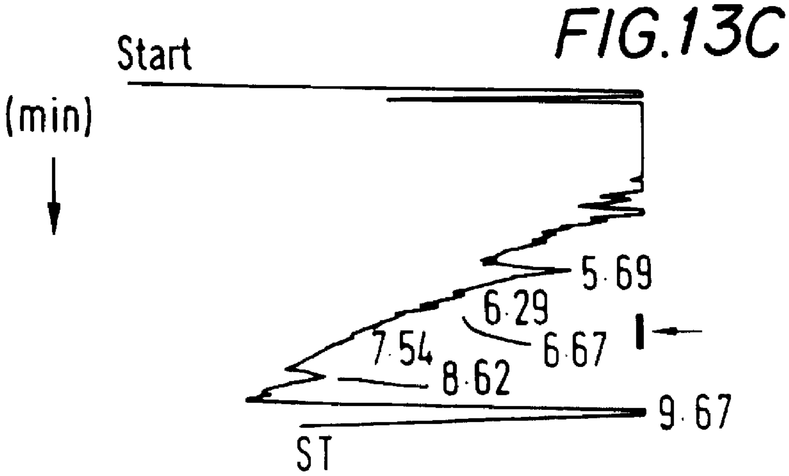

FIG. 13 is a HPLC elution profile of epidermin which was produced in *S. carnosus* TM300.

13A: Elution profile of epidermin standard substance (6.75 min, indicated by an arrow).

13B: Elution profile of epidermin standard substance (6.75 min, indicated by an arrow) isolated from culture filtrates of *S. carnosus* TM300 pTepi14. Culture filtrates were adsorbed to XAD 1180, eluted with methanol and finally concentrated by evaporation.

13C: Elution profile of untransformed *S. carnosus* TM300 culture filtrate treated as in 13B. The solid line indicates the elution region of epidermin.

Figure 14:
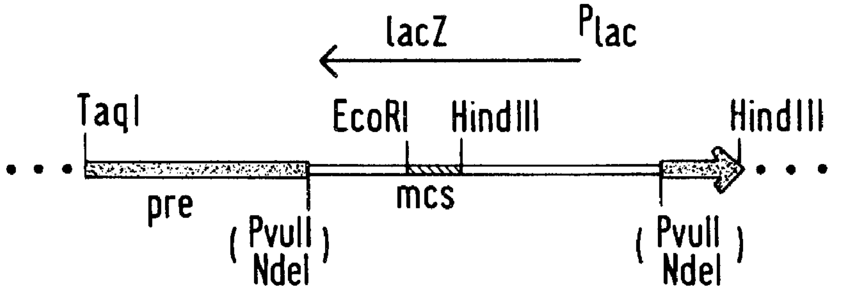

FIG. 14 shows the construction of pT181mcs. The $PvuII^{309}$–$PvuII^{631}$ fragment of pUC19, part of lacZ and the multiple cloning site (mcs), was inserted into the single NdeI site within pre of pT181 (Gennaro et al., *J. Bacteriol.* 169:2601–2610 (1987); Kahn et al, *Plasmid* 10:251–259 (1983)) by blunt-end ligation. lacZ is in the opposite orientation to a pre. Black bar, interrupted pre; open bar, inserted pUC19 fragment.

Figure 15:
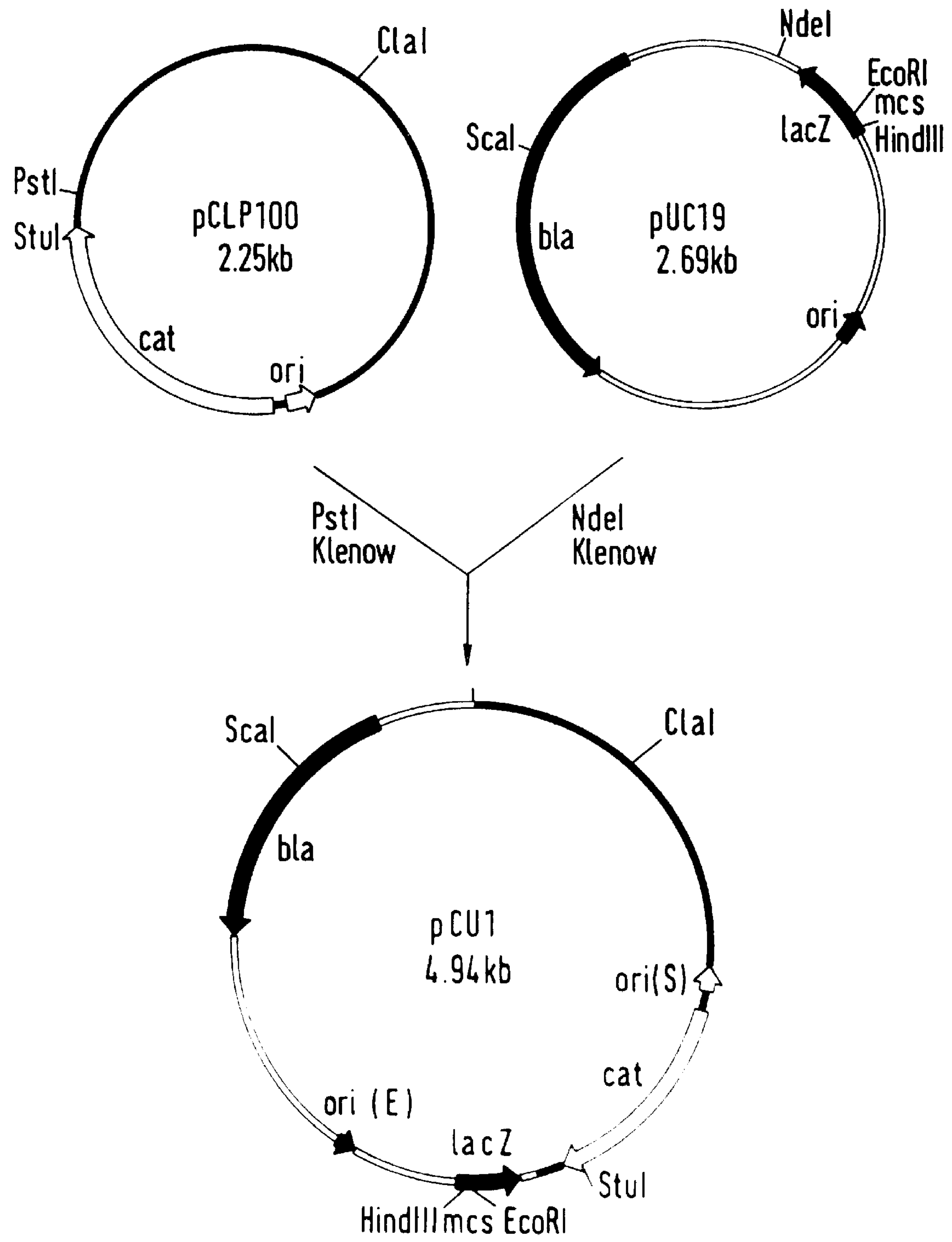

FIG. 15 shows the construction of pCU1. PCLP100 is a derivative of pC194 (Horinouchi et al., *J. Bacteriol.* 150:815–825 (1982)) containing a single Pst1 site which was generated by opening pC194 at the HindIII site, deleting the ends with Ba131 (approximately 950 bp) and inserting a PstI-linker by blunt-end ligation. pCU1 was then generated by blunt-end ligation of pCPL100 and pUC19 (Vieira et al., *Gene* 19:259–268 (1982)) via the single PstI and NdeI sites, respectively. The multiple cloning site (mcs) in front of lacZ was used for cloning various epi gene-containing fragments. This shuttle vector replicates both in staphylococci and *E. coli.*

FIG. 16 shows:

A) the generation of pTepi14 by cloning the 14 kb BglII fragment of pTü32 in pT181 mcs. This fragment containing the entire genetic information necessary for epidermin production in *S. carnosus*. The indicated ORFs and their transcriptional directions (indicated by arrows) are deduced from the DNA sequence. epiA, the structural gene, is presented by the black arrow.

B) various pTepi14 DNA fragments subcloned into pT181mcs (pT . . . ) or pCU1 (pCU . . . ). The respective plasmids were used to complement the *S. epidermidis* $Epi^-$ mutants. The complete ORFs represent in the plasmid are indicated.

Figure 17:
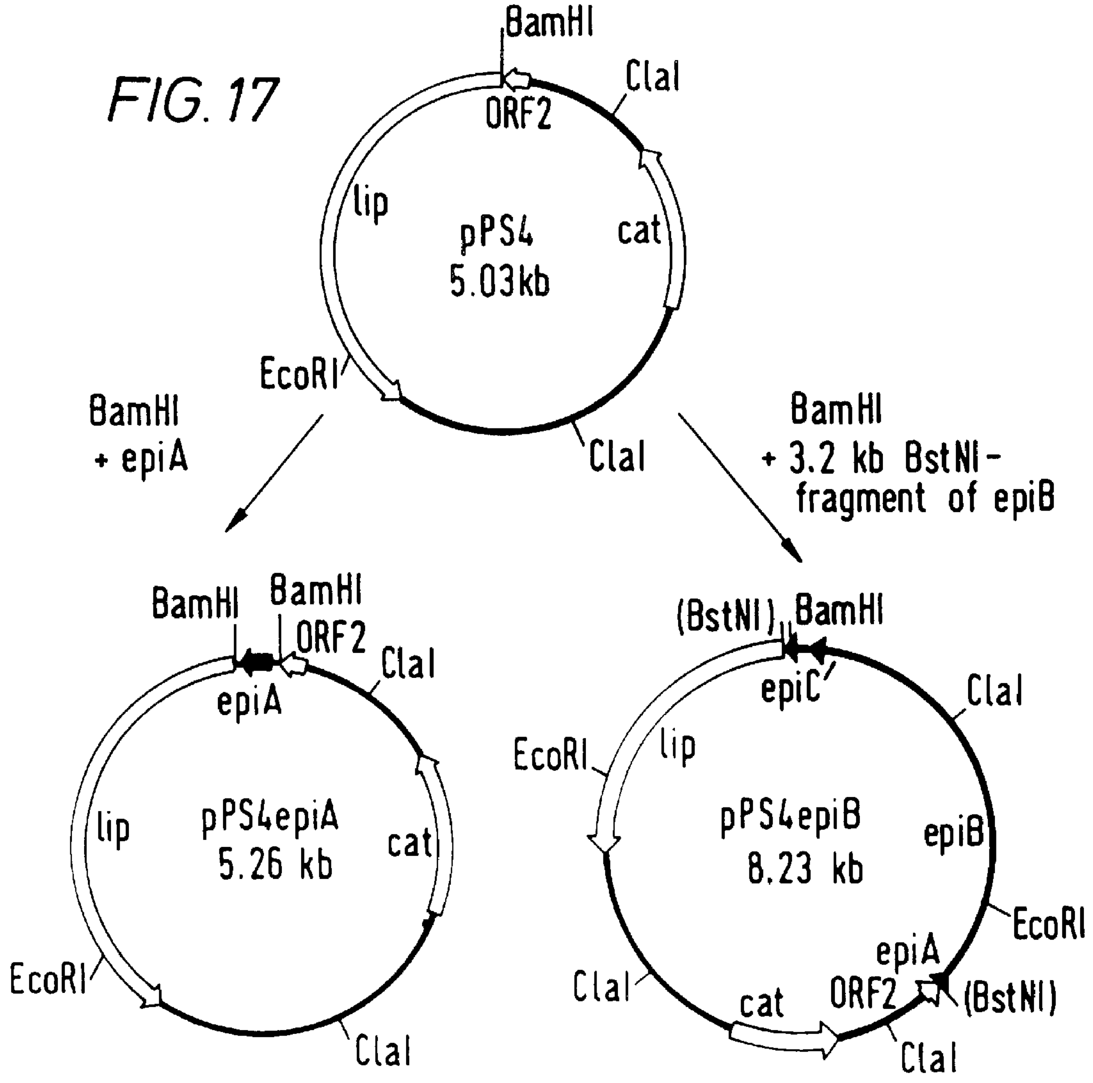

FIG. 17 shows the construction of pPS4epiA and pPS4epiB. pPS4 is a derivative of pLipPS1 (Liebl et al., *Mol. Gen. Genet.* 204:166–173 (1986)). A single BamHI site was inserted after a strong staphylococcal promoter. Cloning of genes into the BamHI site under the control of the ORF2 promoter normally leads to good expression in staphylococci. epiA was PCR-amplified and contained flanking BamHI sites. The 3.2 kb BstNI fragment containing epiB was inserted into the BamHI site by blunt-end ligation. The respective EMS-mutants were complemented only when epiA and epiB were under the control of the ORF2 promoter. lip, lipase gene; cat, chloramphenicol acetyl transferase gene; ORF2, *S. carnosus*-specific truncated ORF.

Figure 18:
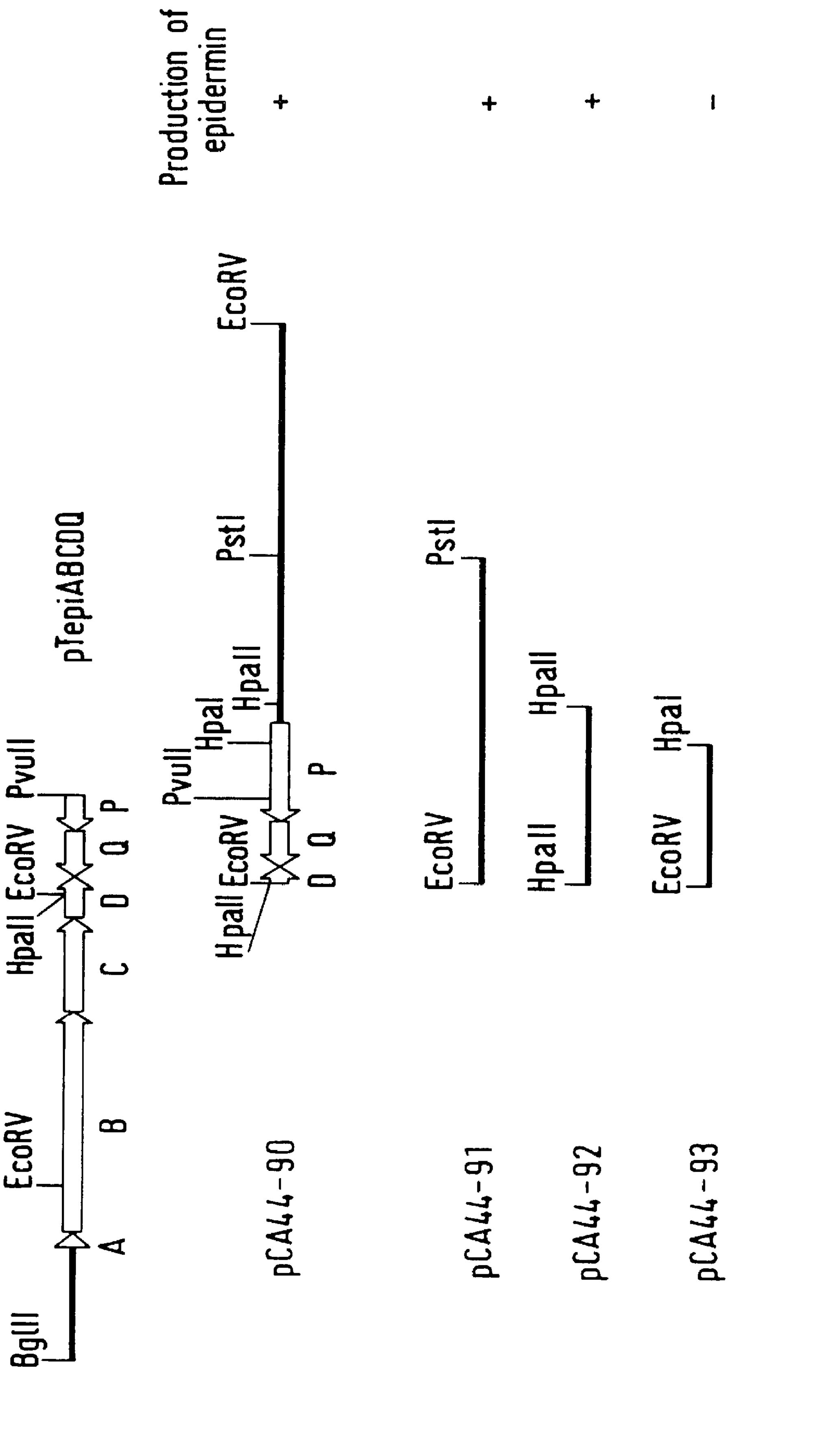

FIG. 18 shows the complementation of epidermin production in *S. carnosus* (pTepiABCDQ) by flanking DNA fragments. The fragments were subcloned into the compatible plasmid.

DESCRIPTION OF THE PREFERRED EMBODIMENTS

Broadly speaking the present invention provides in one aspect a bacterial host containing a plasmid, wherein said plasmid codes for a polypeptide which is not normally produced by said host, and wherein said host during cultivation provides a multi-enzyme complex whereby a polypeptide is produced which contains at least one dehydroamino acid and/or at least one lanthionine bridge, said produced polypeptide being foreign to said host.

A suitable multi enzyme complex is one which is capable of effecting at least one of the following operations, namely water elimination and sulphide bridge formation; the complex may also effect decarboxylation and double bond formation.

Suitable hosts for carrying out the process of the present invention are those which, without modification of their genetic material, are capable of producing polypeptides containing a dehydroamino acid residue and/or lanthionine bridge and/or a methyl lanthionine bridge. Examples of such hosts are *Streptococcus lactis, Bacillus subtilis, Streptomyces cinnamoneus,* Streptomyces sp. *Streptoverticullum griseoverticillum, Staphylococcus epidermis, Staphylococcus epidermin* strain 5, *Staphylococcus gallinarum* and mutant strains thereof, e.g., a mutant strain of *S. epidermis* DSM 3095 which is incapable of producing epidermin.

Strains which are of special interest are *Staphylococcus gallinarum* (F16/P57) Tü 3928 which has been deposited with the Deutsche Sammlung von Microorganismen under the terms of the Budapest Treaty on 18 May 1988 and has received the depository number Tü 3928 in DSM 4616 and *Staphylococcus epidermis* DSM 3095 which was deposited by the present applicants with the Deutsche Sammlung von Microorganismen Mascheroder Weg 1B, 38124 Braunschweig, Germany, under the terms of the Budapest Treaty on 26th Oct. 1984.

In order to transform a suitable host, a suitable plasmid may be modified by known genetic engineering techniques.

Desirably a plasmid from a host which produces a polypeptide containing at least one dehydroamino acid residue and/or at least one sulfide bridge is treated by modifying or replacing the gene coding for a pre-polypeptide to provide a plasmid coding for a polypeptide foreign to said host and then transforming said host with the altered plasmid.

Any of a variety of methods may be used to replace or modify a gene coding for the pre-polypeptide.

DNA coding for the pre-polypeptide sequence of the desired compound can be prepared by chemical synthesis. Suitable chemical syntheses have been disclosed in *Anal Biochem.* 121, 365 (1982). The known techniques allow the preparation of polynucleotides, e.g., of up to 60 to 100 bases to be prepared.

Suitable protected nucleotides can be linked by the phosophotriester method Agarwal et al., (Agnew, *Chem.* 84, 489 (1972)), the phosphotriester method (Reesem., *Tetrahedron* 39, 3, (1983)) or the phosphitetriester method (Letsinger et al., *J. Am. Chem. Soc.* 98, 3655 (1976)) or the phosphoramidite method. The solid phase method allows for simplification of the synthesis of the polynucleotides.

The double stranded DNA can be constructed enzymatically from chemically prepared short but overlapping segments.

For example, overlapping polynucleotide sequences from both DNA strands can be used, which are held together in the correct conformation by base pairing and are then chemically linked by the enzyme DNA ligase (Khorana et al., *J. Biol. Chem.* 251, 565 (1976)).

Another possibility comprises incubating in each case one polynucleotide sequence from the two DNA stands with a short overlapping segment in the presence of the four required deoxynucleoside triphosphates with a DNA-polymerase, for example, DNA-polymerase I, the Klenow fragment of polymerase I or T4 DNA-polymerase, or with reverse transcriptase. The two polynucleotide sequences are thereby held together in the correct arrangement by base pairing and are supplemented with the required nucleotides by the enzyme to give a complete double-strand DNA (Narany et al., *Anal. Biochem.* 121, 365 (1982)).

Another suitable method for obtaining the DNA coding for a polypeptide comprises isolating the DNA from the genomic DNA of a tissue or cell culture or microorganism, lysing the cells e.g. with SDS or proteinase K, or if desired mechanically, and deproteinising the DNA by repeated extraction with phenol.

The RNA can be preferably digested with RNase. The obtained raw DNA is partially digested with suitable restriction enzymes e.g. HaeIII and A1uI and fragments isolated and multiplied in a suitable phage or cosmid, e.g. in charon 4A or EMBL-3 phage and assayed for the desired sequences e.g. with a radioactively labelled DNA probe.

The DNA coding for a desired polypeptide can also be obtained by reverse transcription of isolated mRNA into cDNA. This may be the preferred method if the DNA structure is not known. In this method the DNA is obtained from genomic DNA in a cDNA library via the mRNA. The cDNA library comprises the genetic information which is complementary to the mRNA isolated from cells.

To obtain a cDNA library, the mRNA is isolated from cells expressing the desired basic (possibly unmodified) protein. This mRNA is converted into double stranded cDNA.

Standard methods well known in the art are applied in the preparation of mRNA. The cell membrane is broken and the cell content released from which the mRNA is isolated. The cell membrane is preferably broken by physical methods or lysis with detergents such as SDS, guanidine thiocyanate, definite salt conditions or homogenization, preferably by mixing. The mRNA is isolated by the standard methods of phenol extraction, ethanol precipitation, centrifugation and chromatography, preferably a combination of several methods. Centrifugation is preferably done over gradients, for example over a CsCl gradient. For chromatography, preferably columns are used, especially oligo-dT columns.

The total mRNA can be converted directly into Ds-cDNA following the methods of the art. Preferably the mRNA coding for a desired polypeptide is further enriched using several techniques, such as electrophoresis, chromatography and centrifugation, preferably sucrose gradient centrifugation.

Fractions containing mRNA coding for a desired polypeptide can be detected by various methods, such as in vivo or in vitro translations, followed by detection of a relevant activity or, when the nucleotide sequence is known, by hybridization with an oligonucleotide probe.

In vivo translation systems can be prokaryotic or eukaryotic systems. A preferred in vivo translation system is the *Xenopus laevis* oocyte system (see Maniatis et al., *Molecular Cloning, A Laboratory Manual,* Cold Spring Harbor Laboratory (1982)). In vitro systems are, for example, wheat germ and rabbit reticulocyte lysates, both of which are commercially available.

From any pool of mRNA derived from unfractionated or fractionated mRNA, ds-cDNA can be obtained by the well known methods of the art (preferred general methods are described in Maniatis et al. (supra), Okayam and Berg, *Molecular and Cell Biology* 2, 161–170 (1982) and Heidecker, *Nucleic Acid Research* 11, 4891–4906 (1983)). In general, the mRNA is converted first to ss-cDNA using reverse transcriptase or DNA-polymerase I (Klenow fragment). Two methods are alternatively used for priming the synthesis of the ds-cDNA. The first method was the natural loop formation of the ss-cDNA. The second method is that of tailing the ss-cDNA with a homopolymeric tail such as poly-dC or poly-DT.

The mRNA fraction of which the corresponding polypeptide shows the highest activity in the detection system is transcribed into the complementary cDNA by methods well known in the art. The mRNA and oligo-dT as a primer are mixed, dNTPs are then added as starting material and the synthesis of the cDNA-mRNA hybrid molecule is realized by the enzyme reverse transcriptase. The RNA molecules are degraded by addition of NaOH. DNA polymerase is admixed, preferably the Klenow fragment of the DNA polymerase I, and the mixture is incubated at a suitable temperature, preferably 12°–15° C. The mixture is incubated with nuclease S1 and the ds-cDNA corresponding to the mRNA coding for a desired polypeptide is obtained.

For amplification the obtained ds-cDNA can be spliced into suitable vector e.g. the plasmid pUC-KO and the obtained hybrid vector multiplied by use of a suitable host, e.g. *E. Coli* HB101. Reisolation of the hybrid vectors, and recovering the isolated cDNA therefrom allows a structure determination of the DNA coding for a desired polypeptide.

Preparation of a Hybrid Vector

A hybrid vector of the invention can be prepared by splicing a DNA coding for a polypeptide of the desired sequence into a suitable vector.

Suitable vectors are carriers for integrated passenger DNA, which can be used to transform a host microorganism.

Suitable as vectors are plasmids derived from microorganisms which in an untransformed state produce polypeptides which contain dehydroamino and/or sulfide groups. Suitable vectors carry the insert DNA at a defined position.

In general, such vectors may contain a replicon and a control sequence, i.e. a promoter, which are derived from the host cell or a species compatible with the host cell in which they are used. The vector ordinarily carriers a replicon site and may contain sequences (marker genes) which are capable of providing phenotype selection in transformed cells. Suitable marker genes may provide antibiotic resistance or resistance to heavy metals or they may complement a genetic defect of the host. Further useful sequences in such vectors are enhancer and activator sequences.

One suitable starting vector is a 54 Kbp plasmid pEpi32 from the strain *Staphylococcus epidermis* DSM 3095. This plasmid, which is characterized below, contains the epiA gene encoding for a 52-prepeptide, which is processed to a tetracyclic 21-peptide amide antibiotic. A vector carrying a passenger DNA is designated a hybrid vector.

The desired DNA is spliced into the starting vector by conventional methods.

A starting plasmid for example can first be linearised by a suitable restriction enzymes, e.g. the plasmid pEpi32 by HindIII, BamHI and EcoRI, then d/G-tailed in the presence of dGTP and the terminal deoxynucleotidyl transferase. The double stranded cDNA insert is dC-tailed in the presence of dCTP and terminal deoxynucleotidyl transferase. Combining both cDNA and vector results in the hybrid vector. Bacteriophages, such as lambda, are preferred for constructing genomic libraries. The lambda cloning systems are described by Maniatis (supra). The suitable vector DNA is digested to completion with the appropriate restriction enzyme, and the left and right arms are separated from the central fragments by velocity gradient centrifugation or gel electrophoresis. Another method is to digest parts of the stuffer fragments with restriction enzymes which lack recognition sites in the left and right arms. The isolated genomic DNA can be partially digested to fragments of 13–20 kb in length. Afterwards the arms are ligated with the fragments of foreign DNA having termini compatible with those of the arms.

The appropriate DNA insert is recloned from the original vector used for the original cloning, into a suitable expression vector. To this end appropriate restriction enzymes are used, possibly in combination with oxonucleones, to produce the desired DNA fragments.

The DNA insert may be subcloned into a multiple site of a suitable well known plasmid vector e.g. derivatives of pC194, pTI81 and pUB110 at the restriction sites HindIII/BamHI/EcoRI.

The method of the invention can thus be used to prepare derivatives of known peptides and hormones, in which a cysteine residue in the unmodified peptide is replaced by sulfide-bridged amino acids and serine and threonine are replaced by corresponding dehydroamino acid residues.

These fragments are integrated into an appropriate expression vector by using the cohesive ends directly or by the addition of appropriate chemically synthesized oligonucleotide bridges. For the modification of the ends for example HindIII and BgLII can be used. The method is not limited to any special restriction enzymes. Any desired link can be made between the expression vector and the DNA insert using suitable restriction enzymes in combination with chemically synthesized oligonucleotides.

Appropriate DNA inserts can also be obtained which code for polypeptide having site directed mutagenesis.

A variety of methods may be used to induce mutations of underlying DNA so as to prepare the desired mutants.

One method may comprise first inserting a fragment of a native or basic gene, containing sequences coding for the region to be mutated, into the replicative form of a phage, e.g. phage MI3mp8 to form MI3mp8PA. A synthetic oligonucleotide, complementary to the inserted sequences but containing one or more nucleotidetriplets which code for the amino acid to be substituted, is then annealed to the single stranded form of MI3mp8A to form a double stranded region. This region serves as a primer for DNA polymerase I synthesis of the remaining complementary strand. After replication and identification, the mutant sequence may be further modified or used to construct a suitable vector for expressing the mutated polypeptide.

In the work carried out on epidermin a wobbled DNA probe 5'-GTG(A)CAT(G/A)ATG(A)AAT(C)TT-3' deduced from a suitable pentapeptide segment of the proposed presequence of epidermin LysPheIleCylThr was prepared. This DNA probe was hybridized against plasmid DNA from *S. epidermin* DSM 3095.

Restriction analysis of the isolated plasmid reveals seven DNA fragments with EcoRI (16, 11, 10, 6.5, 5.5., 3.5 and 2.5 kbp), nine DNA fragments with HindIII (17, 14, 10, 5.3, 2.8, 1.8, 0.8, 0.6 and 0.5 kbp) and five DNA fragments with BamHI (20, 19, 10, 3 and 1 kbp).

A 5.4 kbp HindIII fragment was subcloned and subjected to rehybridization whereby the structure gene epiA was located within a 2.2 kbp EcoRI/BglII fragment.

As a mixture of 24 different 14-mers was used as a hybridization probe. The probe was applied in a 30-fold excess as a sequencing primer in accordance with the techniques described in Novick et al. *Ann. N.Y Acad. Sci.* 182, 279–294 (1971), Southern, *J. Molec. Biol.* 98, 503–517 (1975) and Heinrich et al, *Molecul. gen. Genet.* 209, 563–569 (1987). The peptide sequence of epidermin allowed identification of the open reading frame. A single methionine codon is in appropriate distance to a Shine-Dalgaro sequence. The structural gene of pre-epidermin terminates at the TAA stop codon, hence pre-epidermin consists of 52 amino acids (FIG. 1) and it is processed to the epidermin between $Arg^{-1}$ and $Ile^{+}$. Thus, as can clearly be seen, pre-epidermin is not a degradation product of a larger protein but is coded by a distinct structural gene.

Thus, it is apparent that, unexpectedly, the precursor protein of the antibiotics are coded by distinct structural genes.

Figure 2A:
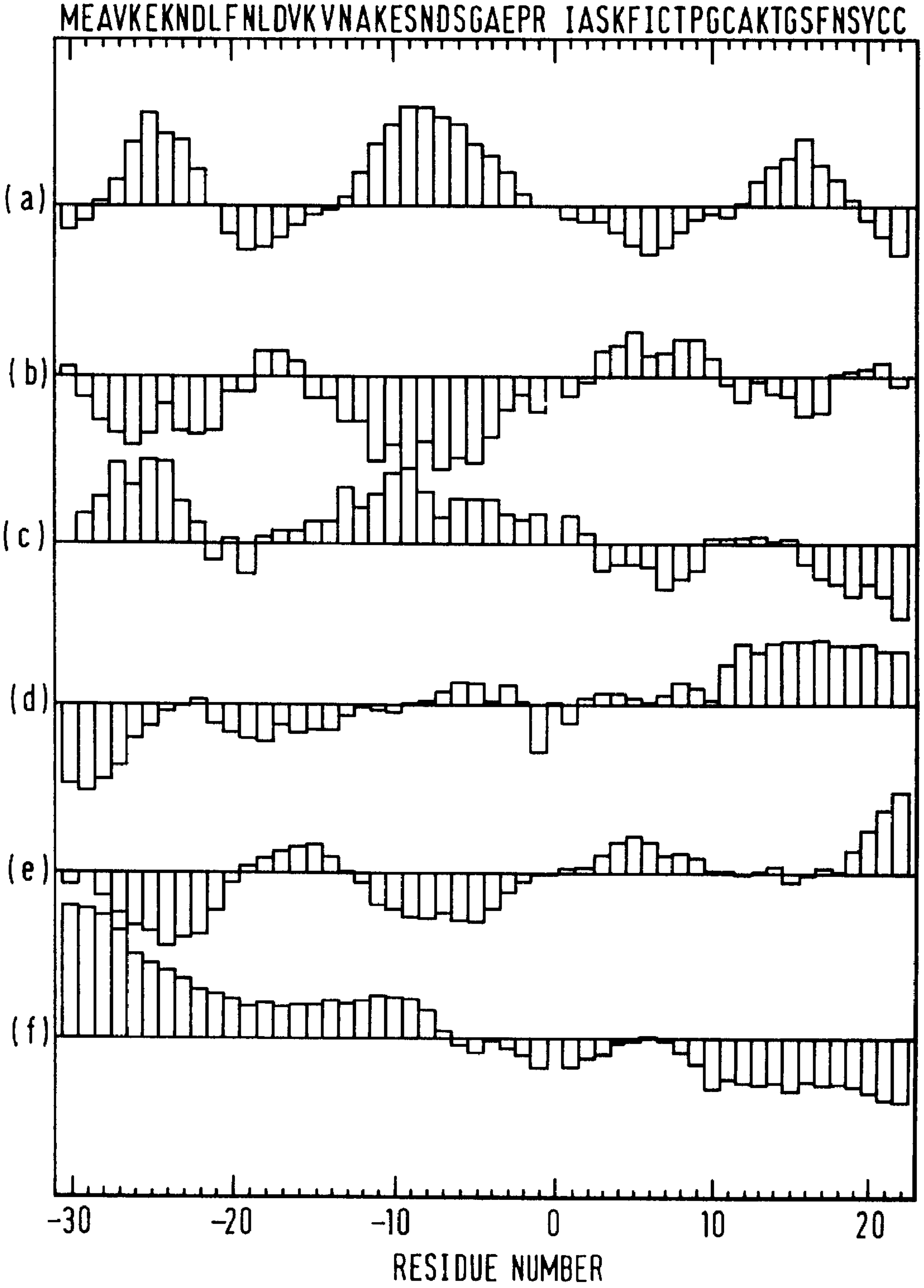
FIG. 2A depicts a prediction plot for pre-epidermin using a Hyron program, in which the respective bar charts show: (a) flexibility; (b) hydropathy; (c) hydrophilicity; (d) propensities for turn; (e) β-sheet; and (f) α-helix conformation.
Figure 2B:
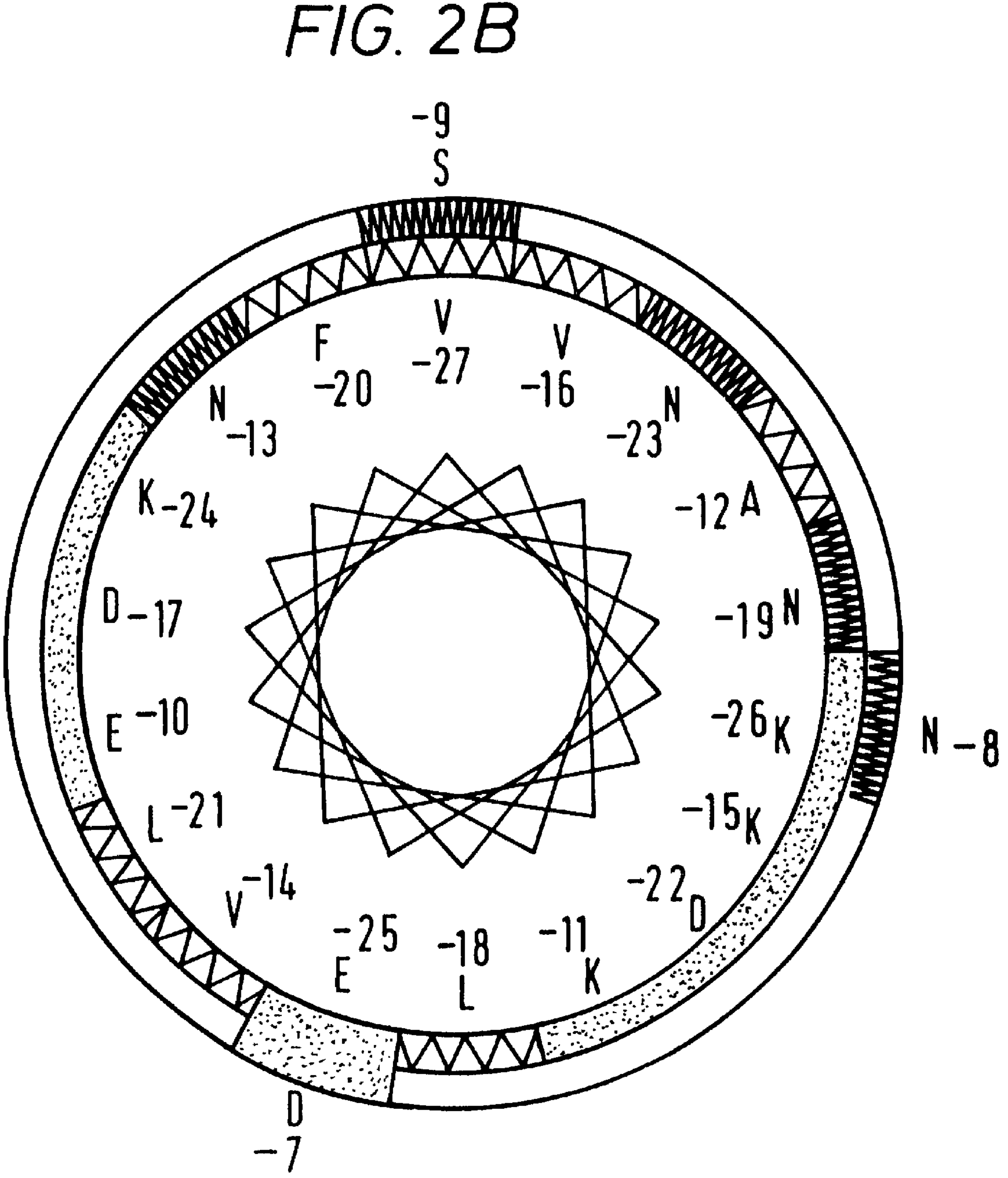
FIG. 2B depicts a helix wheel plot for pre-epidermin showing that the N-terminus may partially adapt an amphophilic α-helical conformation in an appropriate environment.

A combination of prediction profiles for secondary structure (α, β, turns), flexibility, hydropathy, hydrophilicity (FIG. 2A) and helix wheel plot were made using a Hycon program (FIG. 2B). A high α-helix probability is predicted for pre-epidermin −30 to −8 whereas the C-terminal part 1–22 which corresponds to pro-epidermin exhibits very high turn probability. Moreover, the prediction plot shows clearly, that the N-terminus −30 to −1 highly bydrophilic, whereas the C-terminal part is more lipophilic. The N-terminal part −30 to −8 seems to fold partially into an amphophilic α-helix.

The N-terminal segment of pre-epidermin −30 to −1 does not contain any cysteine residues, whereas the C-terminal segment 1–22 contains the four cysteine residues, involved in sulphide bridge formation. Sequence −30 to −1 included many cleavage sites for endoproteases whereas even in the pre-epidermin state, sequence 1–22 is highly resistent to proteolytic degradation.

The mature antibiotic can only be attacked by trypsin at Lys in position 13. The processing site $Arg^{-1}$-$Ile^{+1}$ is hydrophilic and accessible, due to the turn forming $Pro^{-2}$ residue.

Figure 3:
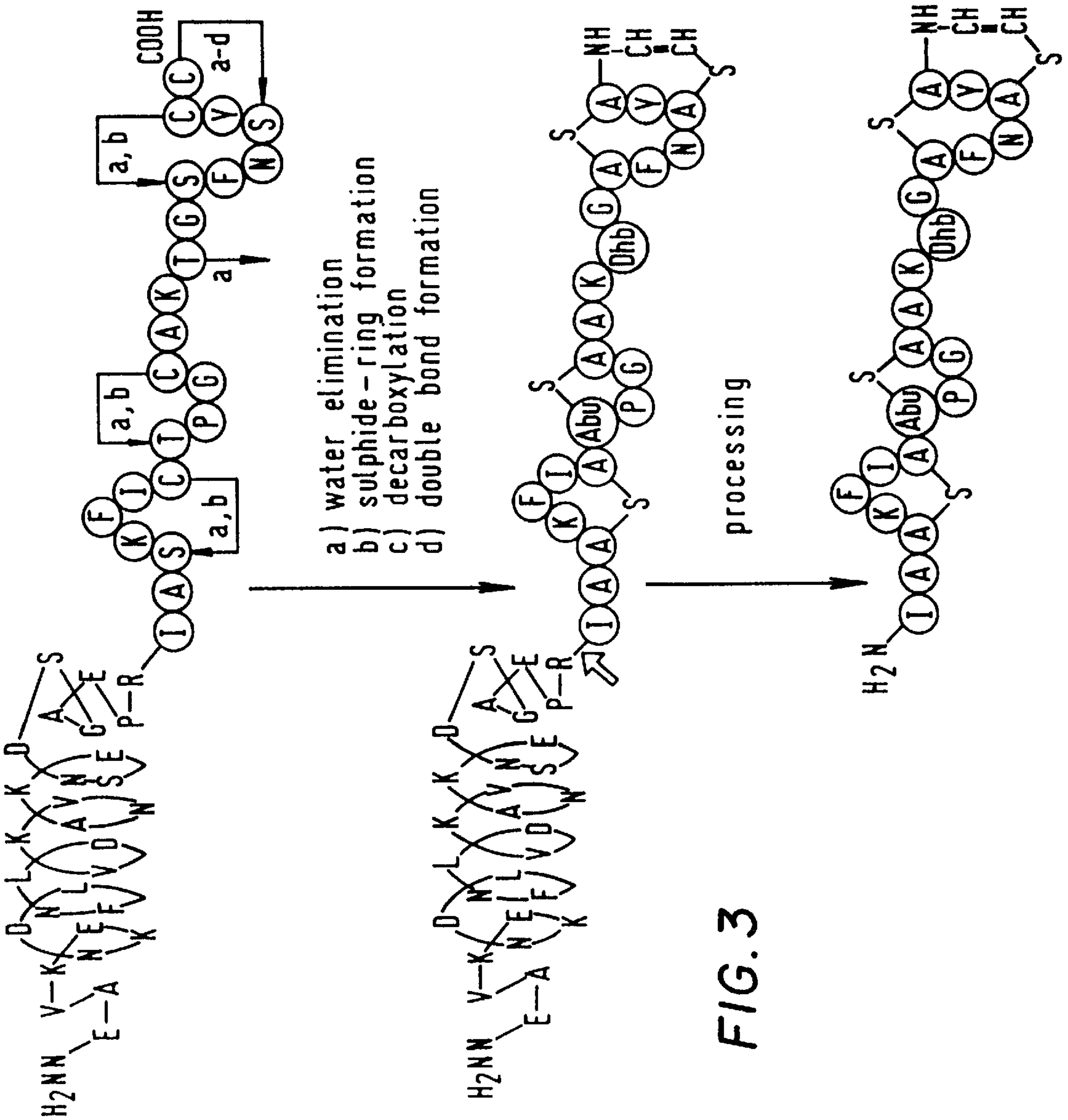
FIG. 3 depicts a postulated naturation procedure for epidermin. The translated polypeptide (pre-epidermin) (SEQ ID NO:12) consists of 52-amino acid residues. Structure predictions indicate a partially α-helical N-terminus from which residues −30 to −10 may form an amphilphilic α-helix conformation. Water elimination occurs at the indicated Ser and Thr residues (a). With the exception of $Thr^{+14}$, water elimination is followed by sulphide ring formation (b) and at the C-terminus, decarboxylation (c) and double bond formation (d) (SEQ ID NO:13) to produce pro-epidermin. The pro-epidermin (SEQ ID NO:14) structure is then processed by proteolytic cleavage to produce epidermin.
Figure 4:
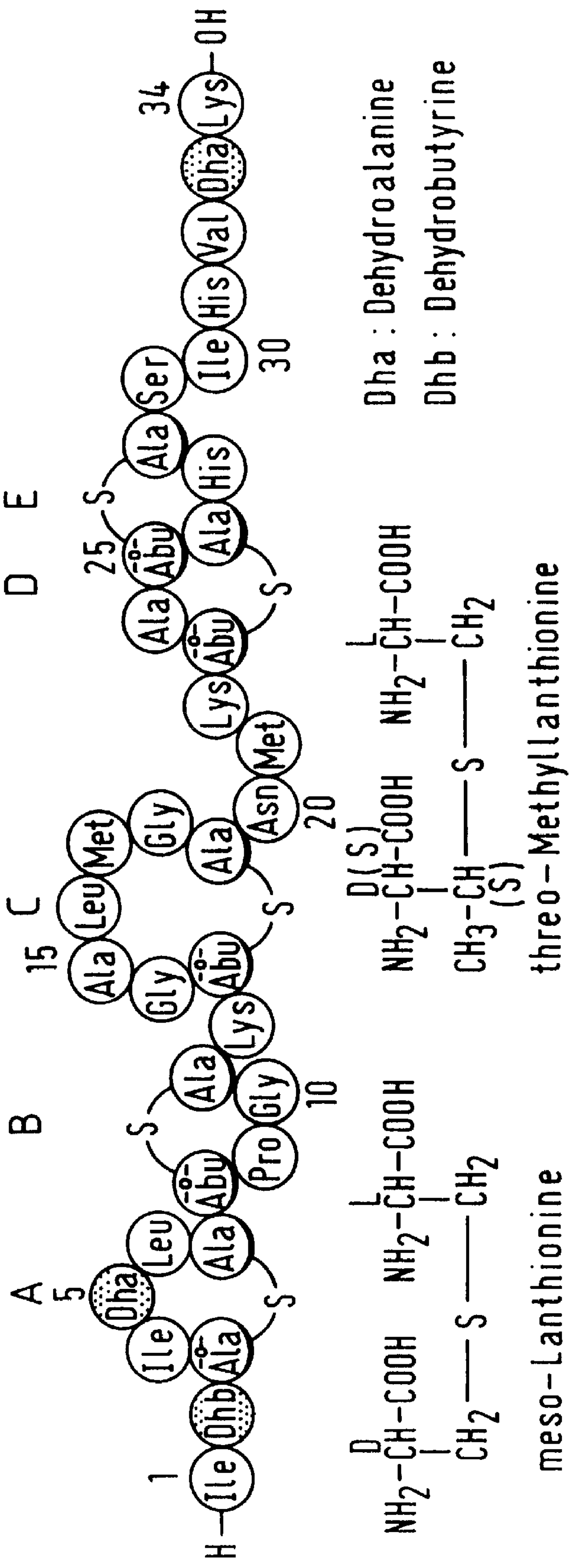
FIG. 4 depicts the structure of epidermin. The ring structures are designated as A, B, C, D and E. The structures of the amino acids mesolanthione and threo-methyllanthione, are set forth.

The various enzymatic reactions which occur in the production of the antibiotics such as epidermin include modifications of the pro-polypeptide part 1–22; cleavage of the N-terminal prepeptide fragment −30 to −1 and secretion of the matured antibiotic (see FIGS. 3 and 4).

The enzymatic modifications occur before cleavage of the prepeptide fragment. Enzymatic modification includes the elimination of water from Ser and Thr residues in position 5, 16, 19 and 8, 14 respectively to form dehydroalanine and dehydrobutyrine residues. Addition of thiol groups of Cys residues in position 2, 11, 21 and 22 to the C═C double bonds, also occurs, yielding the meso-lanthionine or (2S 3S, 6R)-3-methyl-lanthionine bridges. In addition, decarboxylation of residue 22 and double bond formation yields the C-terminal S-(2-aminovinyl)-D-cysteine. The reaction of C-terminally situated cysteine thiol groups with N-terminally located dehydroamino acids occurs with complete stereospecificity in epidermin, nisin and subtilin. Accordingly, during modification these elimination-addition reaction imply a reversal of configuration of the Cα carbon atoms at pre-epidermin residues L-Ser and L-Thr to give D-configured Cα atoms. On the other hand, the L-configuration of the cysteine halves is still maintained.

The four sulphide rings are also formed, subsequently at the same catalytic site, which is supported by the interaction with the N-terminal amphophilic α-helix. Only $Thr^{+14}$ dehydrates without finding a cysteine. This position ($Lys^{+13}$-$Dhb^{+14}$) constitutes the enzymatic cleavage site at which trypsin inactivates the antibiotic epidermin. During sulphide ring formation C-terminal rigidity and hydrophobicity increases and may favor interaction of pro-epidermin with the lipid bilayer and may induce translocation.

Finally, the hydrophilic α-helical N-terminus −30 to −1 is cleaved by a specific protease at the characteristic cleavage site described above.

Using the techniques described above plasmids coding for lantibiotics can be modified either by mutation of the gene coding for the respective polypeptide or by replacement of such a gene by a gene coding for a different polypeptide and used to transform the original host or a different host, provided such host also, in its native state, is capable of expressing a lantibiotic.

Generally speaking, where the original functional gene codes for a pre-sequence, as discussed above for example in the case of epidermin, the DNA sequence coding for such a pre-sequence may be retained in the modified plasmid; in this case the DNA-sequence for the new, or mutated pro-polypeptide will be positioned directly upstream of the pre-sequence DNA similarly to the original pro-polypeptide sequence.

Cultivation of a bacterial host according to the present invention may be carried out under conventionally used cultivation conditions as described for instance in our co-pending British Patent Application No. 8811760.1 which was filed on 18th May 1988 and in European Patent Application Publication No. 0 181 578. Purification and isolation of the desired protein may also be carried out using the techniques or suitable modifications thereof described in the foregoing patent applications for epidermin and gallidermin, including the use of adsorbents, ion-exchange resins and if desired HPLC.

The process of the invention can be applied to the formation of novel compounds for experimental purposes, or to the formation of known compounds or derivatives of known compounds in new hosts. For instance a plasmid containing the gene coding for epidermin can be used to transform the species *Streptococcus lactis* to produce epidermin from that host, or the gene coding for Gallidermin (see our co-pending British Patent Application referred to above) can be used to replace the gene coding for the pro-polypeptide for epidermin in e.g. plasmid pEpi32 and used to transform *Staphylococcus epidermis* DSM 3095 to produce gallidermin from this host. Similarly other biologically active peptide derivatives containing deydroamino acid residues and/or lanthionine bridges and/or methyllanthionine bridges can be produced, such as derivatives of hormones such as human insulin, oxytocin, vasopressin, peptide antibiotics, hormone inhibitors such as elastase inhibitor and fibrinolytically active agents such as human tissue plasminogen activator. Such derivatives, as well as retaining biological activity of the parent compound can have increased stability and improved half-lives.

Ideally the DNA coding for the desired pro-polypeptide should include codons for cystein and serine and/or for cysteine and threonine for the formation of thioether bridges.

For relatively short chain polypeptides these respective codons should normally be no more than eight and preferably no more than six codons apart, inclusive, although it is envisaged that, depending upon the steric conformation of the final polypeptide molecule much greater spacing is possible.

In respect of the formation of dehydroamino acids these will usually be derived from serine and threonine and, accordingly the DNA coding for the desired pro-polypeptide will include codons for such amino acids.

Amongst the unusual amino acids which may be present in a polypeptide produced according to the present invention are, dehydroalanine, 2,3-dehydro-2-aminobutyric acid, meso-lanthionine, (2S, 3S, 6R)-3methyl-lanthionine, S-(2-(Z)-aminovinyl)-D-cystein, lysinoalanine and β-hydroxyaspartic acid; the structure of these residues are shown in FIG. 5.

We have unexpectedly found that the multi enzyme complex responsible for the posttranslational modification of pre-epidermin is located on the 54 kb plasmid pTü32 of *Staphylococcus epidermis* Tü 3298/DSM 3095.

The six genes (ORFs) responsible for the production of epidermin are designated herein epi A, B, C, D, Q and P and are clustered within 8 kb and the proteins for which they code are designated Epi A, B, C, D, Q and P respectively; epi A encodes the 52 amino acid-long pre-epidermin. As described below, epi B, C and D are involved in the four enzymatic modification reactions (i) water elimination by a serine/threonine dehydratase, (ii) sulfur addition by a lanthionine synthase, (iii) C-terminal decarboxylation by a cysteine decarboxylase and (iv) double bond formation. Epi P protein is believed to be responsible for cleaving the mature epidermin from the N-terminal leader peptide, based on its striking homologies with the essential domain of serine proteases (Koide et al., *J. Bacteriol.* 167:110–116 (1986); Meloun et. al., *FEBS Lett.* 183:195–200 (1985); and Stahl et al., *J. Bacteriol.* 158:411–418 (1984)) whilst Epi Q is believed to be a regulatory protein regulating epidermin biosynthesis, based on its distinct homology to the pho B gene of *E. coli* (Makino et al., *J. Mol. Biol.* 190:37–44 (1986)), the fact that both proteins are of a similar size with 205 (epi Q) and 229 (pho B) amino acid residues, the observed homology of 24.2% extending over the 153 C-terminal amino acid residues and the hydrophilicity plots of both proteins.

As a result of the unexpected finding of the entire genetic information for the epidermin biosynthesis and the elucidation of the genes for the proteins epi B, C, D, Q and P, it is now possible to obtain the isolated DNA coding for the proteins, and to construct plasmids containing one or more of these genes so that upon cultivation of a host containing such plasmids one of these proteins alone or predetermined combinations of the proteins may be expressed and subsequently isolated.

The present invention therefore includes DNA sequences encoding respectively for the protein Epi B or Epi C, or Epi D, or Epi P or Epi Q. These sequences may be isolated DNA either single or double stranded, obtained by cleavage of and isolation from pTü32 in known manner or obtained by chemical synthesis or any other conventional procedure. The DNA may also be integrated in a plasmid, suitably an expression plasmid and under the control of a promoter regulator; such constructs when transformed into a suitable host which is then cultivated will express the protein Epi B, Epi C, Epi D, Epi P or Epi Q or combination of these proteins according to which DNAs were ligated into the plasmid. Alternatively plasmid pTü32 may be treated with suitable restriction nucleases to excise one or other of the DNA sequences, followed by religation after any necessary modification of the free ends of the digested plasmid, so as to create a modified plasmid containing DNA sequences coding for predetermined ones of epi B, C, D, P and Q.

A further variant comprises the substitution of the gene coding for epidermin in pTü32 with a DNA sequence coding for a predetermined amino acid sequence whereby cultivation of a suitable host with the modified plasmid will result in expression of a protein different from epidermin.

It is thus possible to substitute a DNA sequence encoding for gallidermin or mutant epidermin or other lantibiotic or other protein, for the epidermin coding sequence in pT ü32 whereby the resulting plasmid can be transformed into a suitable host which may be a host normally incapable of producing a lantibiotic or any of the proteins Epi B, C, D, P or Q and to cultivate the host under conditions whereby the substituted DNA sequence and the genes epi B, C, D, P and Q are expressed, so as to obtain a protein which is gallidermin, mutant epidermin or other protein containing at least one structural feature of a lantibiotic.

Alternatively the genes coding for the proteins Epi B, C, D, P or Q may be inserted into a suitable vector, together with a DNA sequence encoding a predetermined amino acid sequence, the genes coding for the Epi proteins and the predetermined amino acid sequence being operably connected with suitable promoter regulator functions, the resulting plasmid being transformed into a suitable host which may be a host normally incapable of producing a lantibiotic or any of the proteins Epi B, C, D, P or Q, and the host cultivated so that the inserted genes cause the expression of a protein derived from said predetermined amino acid sequence but containing a lantibiotic structural feature, which protein may be gallidermin, epidermin, mutant epidermin, or another protein.

The present invention thus also includes within its scope DNA sequences capable of hybridizing, preferably under stringent conditions, with the DNA sequences described herein and coding for proteins having substantially the activity of the proteins Epi B, C, D, P or Q. Stringent hybridization conditions select for DNA sequences of greater than 85% or, more preferably, greater than about 90% homology. Screening of the cDNA library may be carried out under highly stringent conditions according to the method described in European Patent Application No. 88 119 602.9 and Kashima et al. (*Nature* 313:402–404 (1985)). The DNA sequences capable of hybridizing under stringent conditions with the DNA sequences disclosed in the present application may be, for example, allelic variants of the disclosed DNA sequences, may be naturally present in the particular microorganism but related to the disclosed DNA sequences, or may derived from other sources. General techniques of nucleic acid hybridization are disclosed by Maniatis, T. et al, In: *Molecular Cloning a Laboratory Manual*, Cold Spring Harbor, N.Y. (1982), and by Haymes, B. D. et al., In: *Nucleic Acid Hybridization, a Practical Approach,* IRL Press, Washington, D.C. (1985), which references are herein incorporated by reference. The proteins Epi B, C, D, P and Q are valuable and interesting new reagents potentially useful in the preparation of novel proteins or other substances containing structural features such as dehydroalanine, debydrobutynine, meso-lanthionine, 3-methyl-lanthione, and S-(2-aminovinyl)-D-cysteine.

As such, they may be utilized as isolated proteins, or as chemical catalytic reagents in chemical synthesis procedures to investigate the extracellular processing of proteins by such enzymes.

The invention also relates to the proteins Epi B, C, D, P and Q in substantially pure form. By the term "substantially pure" is intended that the protein is free of the impurities that are naturally associated therewith. Substantial purity may be evidenced by a single band by electrophoresis.

The polypeptides of the invention may be isolated and purified from the above-described recombinant molecules in accordance with conventional methods, such as extraction, precipitation, chromatography, affinity chromatography, electrophoresis, or the like. Preferably, the polypeptides are produced as part of a fusion protein which further comprises an auxiliary protein. Such auxiliary which facilitates the isolation and purification of the polypeptide of interest. Such auxiliary proteins include, for example, typical secretion signals, the maltose binding protein from *E. coli*, or protein A. Methods for preparing fusion proteins comprising protein A, the purification thereof by immunoaffinity chromatography, and the cleavage thereof to release the protein of interest is taught for example, in PCT Application Publication No. WO84/03103 (1984).

A necessary condition to permit cleavage of the fusion protein is that it contains a unique cleavage site which may be recognized and cleaved by suitable means. Such a cleavage site may be a unique amino acid sequence recognizable by chemical or enzymatic means and located between the desired protein and the auxiliary protein. Such a specific amino acid sequence must not occur within the desired protein or auxiliary protein. Examples of enzymatic reagents include proteases such as collagenase which may recognize the amino acid sequence $NH_2$-Pro-X-Gly-Pro-COOH, wherein X is an arbitrary amino acid residue, e.g. leucine; chymosin (rennin) which cleaves the Met-Phe bond; kallikrien B which cleaves on the carboxyl side of Arg in X-Phe-Arg-Y; enterokinase which recognizes the sequence X-$(Asp)_n$-Lys-Y, wherein n=2–4, and cleaves it on the carboxyl side of Lys; thrombin which cleaves at specific arginyl bonds. Examples of chemical agents which may be used to cleave the fusion proteins include cyanogen bromide which cleaves after Met; hydroxylamine which cleaves the Asn-Z bond wherein Z may be Gly, Leu or Ala; formic acid which in high concentration (~70%) specifically cleaves Asp-Pro.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLES

Example 1

1. Overproduction of gallidermin

A DNA fragment containing the open reading frame of gallidermin can be cloned in *Staphylococcus epidermidis* DSM 3095, the epidermin producing strain by using a medium copy plasmid such as pC194, pE194, pUB110, pT181 or pMK148 gallidermin. An increase of the gene doses usually correlates with an increase of product production; the correlation is not necessarily linear. High copy number plasmid derivatives of pC194 or pT181 can be used as cloning vehicles too.

2. Exchange of leader sequence

The leader-sequence of epidermin corresponding to amino acids −1 to −30, is involved in the secretion of epidermin. The sequence can be used to secrete other peptides in *S. epidermidis* such as gallidermin.

The leader-sequence DNA can be made portable by inserting respective linkers at the beginning and at the end of its sequence. Thus the leader sequence DNA can be isolated in large amounts from the plasmid and can be inserted at respective positions of other peptides and proteins. The leader-sequence DNA can also be produced by chemical synthesis.

Example 2

Production of Gallidermin using *S. epidermis* as host

Figure 6:
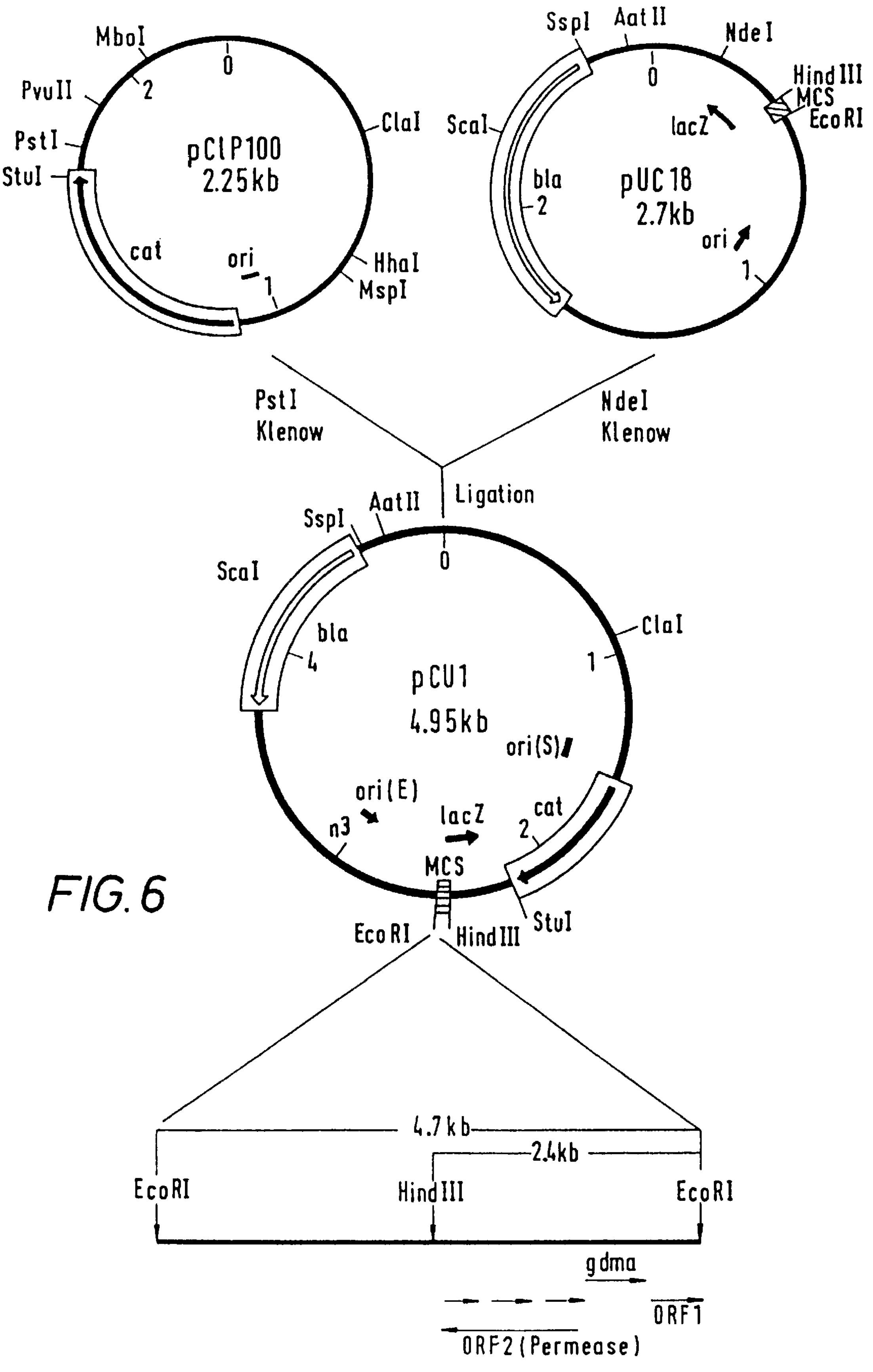
FIG. 6 depicts a schematic representation of the process for preparation of the pCUI plasmid from pCLP100 plasmid and pUC18 plasmid.

1. Preparation of plasmid (see FIG. 6)

a) Plasmid pCUI was prepared by ligating Pst1 digested pCLP100 and Ndel digested pUC18 using Klenow as described in the thesis "Molekular genetische Untersuchungen zur plasmidkodierten Arsenit und Arsenatrestistent bei Staphylococcen", by Dr. Ralf Rosenstein (available from the Technische Universitat, Munich, West Germany). The resulting plasmid was then digested with EcoR1.

b) Chromosomal DNA was isolated from *S. gallinarum* (DMS 4616) and was digested with EcoR1. A 4.7 kb fragment containing the gallidermin structural gene in a 2.4 kb long sequence between HindIII and EcoR1 restriction sites was isolated using as a primer the sequence.

5'CAC ATC CAG GAG TAC 3' c) The 4.7 kb Fragment was then ligated into the EcoR1 site of the digested pCUI plasmid from step a) to give a plasmid designated pCUgdm1. The plasmid pCUgdm1 was deposited under the Budapest Treaty on Dec. 8, 1997, and was assigned Accession Number DSM 11880.

2. Preparation of a *S. epidermis* host

In this example a mutant strain of *S. epidermis* DSM 3095 incapable of producing epidermin was isolated.

The mutagenesis was carried out on a strain which was characterized by chromosomally coded Rifampicin resistance (20 ug/ml).

*S. epidermis* DSM 3095 grown on Agar plates was used to inoculate 30 ml basic broth medium which was cultivated overnight. 0.5 ml of the overnight cultivation was then used to inoculate 50 ml of production medium which was shake cultivated at 37° C. for three hours.

Cells were removed from the cultivation medium and suspended in 4.5 ml pre-warmed TM-Buffer (30 mM Tris-Maleate pH 6.5 (the resulting solution is designated Solution A)).

The solution A was checked for spontaneous mutations and for cell count ($1.25\times10^{10}$ cells/ml).

4 ml of solution A was thoroughly shaken with 1 ml ethyl methyl sulphonate (final concentration 47 $\mu$g/ml) and then maintained under shaking at 37° C. for one hour.

Cells were then extracted from the cultivation broth, washed twice in TM-Buffer and resuspended in 5 ml TM-Buffer (the resulting solution was designated Solution B and contained mutated cells).

Solution B was found to contain $2\times10^8$ cells/ml which corresponds to survival rate of 1.6%.

50 ml of solution B was added to 5 ml production medium and grown overnight at 37° C. (phenotypic expression). The resulting solution was designated Solution C. A cell count showed $7.3\times10^8$ cells/ml.

The solution was plated on BM-Agar plates and individual colonies were picked out. These were used to inoculate test plates (consisting of BM-Agar to which *Micrococcus luteus* has been laid on the surface). Those colonies which had no inhibitory effect on *M. luteus* were selected as non-producers of Epidermin.

BM Agar contains per liter:

10 gm Peptone No. 140

5 gm Yeast extract 1 mg Glucose 5 mg NaCl 1 mg $K_2HPO_4$ pH 7.5

A mutation rate of about 3% was noted.

The 45 non-producers which were found were sub-cloned 20 times to yield 16 stable non-producers.

All stable non-producers were found to contain the wild type plasmid pEpi32. From the restriction pattern this is identified as identical to the plasmid in the wild type strain.

Transformation of non-producing *S. epidermis*

750 ml of BM-medium was inoculated with 5 ml of medium obtained by overnight cultivation of a stable non-producing strain, and the inoculated medium was shake cultivated in a 2 liter flask at 37° C. with a shake speed of 120 rpm.

The initial optical density of the inoculated BM-medium was 0.03–0.04. When the optical density had reached 0.45–0.55 the cells were removed by centrifugation in a GS.-3-Rotor at 8500 rpm for 15 minutes at 4° C. The isolated cells were then washed successively in 750, 350, 40 and 10 ml of 10% glycerin, suspended in 2–3 ml 10% glycerin, and frozen in 110 ml portions in ERGs at −70° C. The cell count amounted to 1–5×$10^{10}$/ml.

The frozen cells were thawed at room temperature for 5 minutes, then 50 μl of cell suspension was incubated in an ERG with 2 μl plasmid pCUgdm1 in TE-Buffer for 30 minutes at room temperature.

The mixture was then introduced into an electroporation cuvette having a 0.2 cm electrode gap and immediately electroporated. Thereafter the cells were rapidly resuspended in 950 μl SMMP50-medium, transferred into a 2.5 ml ERG and shaken for 90 minutes at 37° C. The ERGs were inclined at 45° C. in order to provide for a good aeration of the medium.

SMMP50-medium contains pro 100 ml, 55 ml 2SMM, 40 ml 4 PAB and 5 mol 5% BSA. The 2SMM contains 1 mol saccharose, 0.04 mol maleic acid, 0.04 mol $MgCl_2$ and NaOH to pH 6.5. 4 PAB is a solution of 7 g/100 ml of Gibco antibiotic medium 3.

The cell suspension is diluted and spread on a BM-Agar containing gallidermin which is incubated for 20 hours at 37° C.

Testing of growing strains which produce gallidermin was carried out by selection of colonies from a *M. luteus* test plate and by cultivating the respective selected colonies and determining the presence of gallidermin by HPLC.

Three pCUgdm1 transformed mutants capable of producing gallidermin were located.

Determination of the presence of gallidermin produced by pCUgdm1 transformed *S. epidermin* a) Bio assay

FP-Agar was inoculated with *M. luteus* ATCC 9341 and incubated at 37° C. for 18 hours. Half of the produced culture was removed with a loop and suspended in 100 ml FP-medium and was cultivated for 8 hours at 36° C. The cultivation was stopped when the optical density reached 1.0. FP-Agar was inoculated with 0.5% of this suspension, each 10 ml was poured into a Petri dish and stored for 3 weeks at 4° C.

The Plate diffusion test was carried out as described in Zähner and Maas, "Biology of Antibiotics", Springer Verlag, Berlin 1972. 10 ul of culture filtrate from cultivation of the transformed *S. epidermin* was captured on a filter paper and dried. The paper was placed on the test plate which was then incubated for 24 hours at 37° C.

b) HPLC

The selected transformed strain was cultivated for 26 hours in the production medium. The culture broth was centrifuged for 10 minutes at 13.000 rpm.

The isolated culture liquid was then subject to HPLC on a SP 8.700 liquid chromatography apparatus (Spectra Physics, Darmstadt, FRG) using as the mobile phase A) $H_2O$ with 0.5% 70% perchloric acid and B) Acetonitrile. Column packings were Nucleosil −100 C-18 of grain size 7 um and column sizes 125 mm×4.6 mm I.D. and 20 mm×4.6 mm ID for the pre-column.

Gradients were as follows:

| time (min.) | A [%] | B [%] |
|---|---|---|
| 0 | 77.5 | 22.5 |
| 8 | 63.0 | 37.0 |
| 8.5 | 0 | 100 |
| 9.5 | 0 | 100 |
| 10 | 77.5 | 22.5 |
| 14 | 77.5 | 22.5 |

Figure 7A:
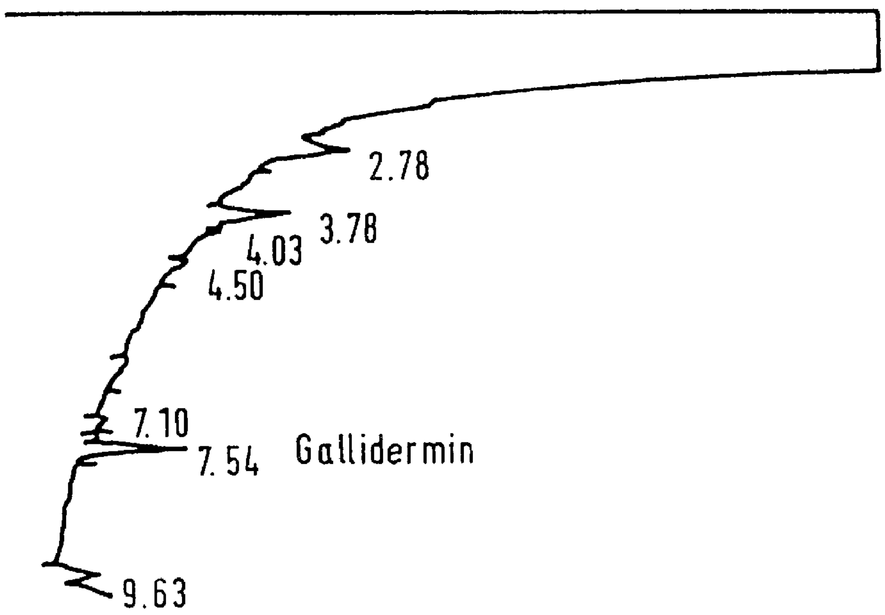
FIGS. 7A and 7B depict the elution pattern of the isolated culture medium prepared in Example 2.
Figure 7B:
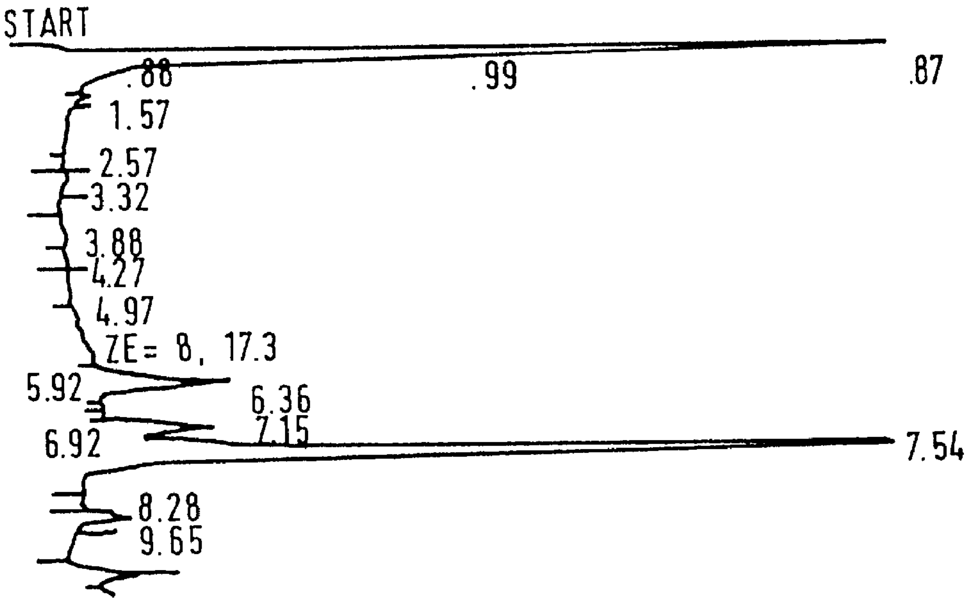

The resulting chromatogram is shown in FIG. 7A. A standard curve is shown in FIG. 7B showing that gallidermin elutes at 7.54 minutes.

The following were used as culture medium.

| | | | |
|---|---|---|---|
| 1. FP-Agar | Meat extract | 4 | g |
| | Peptone | 10 | g |
| | NaCl | 3 | g |
| | $Na_2HPO_4$ | 5 | g |
| | Glucose | 10 | g |
| | Complex agar | 15 | g |
| | Water | 1 | liter |
| | pH | 7.2 | |
| 2. FP-Medium | Meat extract | 4 | g |
| | Peptone | 10 | g |
| | NaCl | 3 | g |
| | $Na_2HPO_4$ | 5 | g |
| | Glucose | 10 | g |
| | Water | 1 | liter |
| | pH | 7.2 | |
| 3. Production medium | Meat extract | 33 | g |
| | Malt extract | 30 | g |
| | NaCl | 40 | g |
| | Calcium Hydroxide | 3.8 | g |
| | Water | 1 | liter |
| | pH | 6.5 | |

Example 3

Plasmid Isolation

Plasmid DNA from *S. epidermis* Tü3298 was isolated according to a modified procedure of Norick et al., *Ann. NY-Acad. Sci.* 182:279–294 (1971). *S. epidermis* was grown on BM-media (1% peptone 140, Gibco, Neu-Isenburg, F.R.G., 0.5% yeast extract, Difco, Detroit, U.S.A., 0.1% glucose, 0.5% NaCl and 0.1% $K_2HPO_4$×$2H_2O$) until stationary phase. Cells were centrifuged and washed twice with 0.5M EDTA. The pellet was resuspended in 80 ml NaCl buffer (50 mM Tris/HCl, pH 7, 50 mM EDTA, 2.5M NaCl), 1.5 ml lysostaphin solution (0.5 mg/ml, Sigma, Heidelberg, F.R.G.) was added and the suspension was incubated at 37° C. for 20 min. Cells were lysed by the addition of 80 ml lysis buffer (50 mM Tris/HCl, pH 8, 300 mM EDTA, 500 mM Brij., 40 mM sodium deoxycholate and kept on ice for 1 h. The lysate was centrifuged (30 min, 13,000 rpm, 4° C. ) and the supernatant was mixed with one quarter of its volume with 50% solution of PEG-6000. Plasmid DNA was precipitated at 4° C. overnight. The DNA suspension was centrifuged (20 min, 13,000 rpm, 4° C.), resuspended in 8 ml TE buffer and 50 μl of proteinase K solution (20 mg/ml) was added. After incubation at 37° C. for 15 min the DNA was precipitated with ethanol and further purified by CsCl centrifugation (1 g CsCl/ml, 40,000 rpm, 40 h, 20° C.).

RNA isolation and electrophoreses

*S. epidermis* was grown on SMS minimum medium (Terzaghi et al, *Appl. Microbiol.* 29:807–813 (1975)) and RNA isolated therefrom, using a modified procedure similar to that described for *Bacillus subtilis* RNA (Ulmanen et al., *J. Bacteriol.* 162:176–182 (1985)). Cells were lysed with lysostaphin (0.1 mg/ml) in protoplasting buffer and incubation was performed at 37° C. Total RNA was glyoxylated (McMaster et al., *Proc. Natl. Acad. Sci. USA* 74:4835–4839 (1977)) and separated on a 1.2% agarose gel using 10 mM $Na_2PO_4$, pH 7, as electrophoresis buffer. RNA was stained with ethidium bromide and blotted to a nitrocellulose membrane (Scheider and Schuell, Dassel, F.R.G.) by capillary transfer with 20×SSC buffer (0.15M NaCl, 0.015M tri sodium citrate, pH 9). 23SrRNA and 16SrRNA were used as size standards.

In vitro transcription

Single stranded RNA probes were obtained by cloning the respective fragment in a pSPT18/19 vector system (Boehringer Mannheim, Mannheim, F.R.G.). The plasmids were linearized with EcoRI or HindIII to get a linear DNA template. For transcription the protocol in Melton et al., *Nucl. Acid Res.* 12:7035–7056 (1984), was modified according to the instructions of the commercial supplier. T7-RNA polymerase or SP6-RNA polymerase was used in the presence of $\alpha^{32}$P-CTP (800 Ci/mMol). Unincorporated ribonucleotides were separated from labeled RNA by Sephadex G50 chromatography.

Northern hybridization

RNA was transferred after electrophoresis according to Thomas, P. S., *Proc. Natl. Acad. Sci. USA* 77: 5201–5205 (1980). After 2 h incubation at 80° C. the filter was shortly incubated in 20 Tris/HCl, pH 8, at 100° C. to reverse glyoxylation. Afterwards filters were prehybridized at 42° C. in 50% formamide, 5×SSC (0.15M NaCl, 0.015M tri sodium citrate, pH 9), 50 $NaPO_4$, pH 6.5, 0.1% ficoll 400 (Pharmazia, Freiburg, F.R.G.), 0.1% polyvinylpyrollidone, 0.1% bovine serum albumin and 0.25 mg/ml denatured salmon sperm DNA for 2 h. After probe addition hybridization was performed in the same buffer at 42° C. for 12 h. Filters were washed once in 1×SSC, 0.1% SDS at 42° C. for 15 min and exposed to Kodak-X Omat films at −70° C. for 4 h. Thereafter filters were washed twice with 0.5 SSC, 0.1% SDS at 70° C. for 15 min and autoradiograms were exposed at −70° C. for 16 h. Next day washing was continued with 0.1×SSC, 0.1% SDS at 70° C. for 30–60 min and afterwards again exposed to Kodak-X Omat films at −70° C. for 3 days.

Southern hybridization

For southern hybridization (Southern, E. M., *J. Mol. Biol.* 98:503–517 (1975)) 5' labeled oligonucleotides were used as probes at 23° C. Oligonucleotides were labeled with gamma$^{32}$P-ATP using 4T polynucleotide kinase (Boehringer Mannheim, Mannheim, F.R.G.). Oligonucleotides and primers were synthesized on a 391 DNA synthesizer (Applied Biosystems, Weiterstadt, F.R.G.) and used without further purification.

DNA sequencing

DNA was sequenced radioactively and non-radioactively by the chain termination method (Sanger et al., *Proc. Natl. Acad. Sci. USA* 74:5463–5467 (1977)) using T7-DNA polymerase (Pharmazia, Freiburg, F.R.G.). Radioactive plasmid sequencing was performed as described in Hattori et al., *Anal. Biochem.* 152:232–238 (1984) with appropriate primers. The 3.6 kb BamHI/PstI fragment was sequenced non-radioactively on an Applied 373A DNA sequenator (Applied Biosystems, Weiterstadt, F.R.G.). The respective fragment was cloned in phagemid pBSK∓. The construction was digested with BamHI and SacI and the linearized DNA was unibidirectionally digested from the 5' end with exonuclease III (Boehringer Mannheim, Mannheim, F.R.G.) to obtain a set of nested deletions which were treated with mung bean nuclease (Boehringer Mannheim, Mannheim, F.R.G.) to receive blunt ends. After electrophoresis (1% agarose gel) fragments of appropriate size were isolated from the gel, religated and transformed into *E. coli* strain XL-1 Blue. Single stranded DNA was isolated by using helper phage CSM13 and sequenced with Taq Polymerase (Promega, Freiburg, F.R.G.) according to the protocol of the commercial supplier.

Plasmid Construction

The staphylococcal tetracycline resistance plasmid pT181 has been sequenced (Kahn el al., *Plasmid* 10:251–259 (1983)) and found to contain a single NdeI site within the pre-gene which is not necessary for plasmid replication (Gennaro et al, *J. Bacteriol.* 169:2601–2610 (1987)). The multiple cloning site (mcs) of the *E. coli* vector pUC19 (Yanisch-Perron et al., *Gene* 33:103–119 (1985)) was inserted into the NdeI site to form pT181mcs (see FIG. 14).

A staphylococcus-*E. coli* shuttle vector, pCUI (FIG. 10) was constructed from pCLP100, a derivative of the staphylococcal chloramphenicol resistance plasmid pC194 (Horinouchi et al., *J. Bacteriol.* 150:815–825 (1982)) and the *E. coli* vector pUC19. PCUI is stably maintained in both hosts with an insert size up to approximately 6 kb. pT181mcs and pCUI are compatible in staphylococci and were used to subclone DNA fragments from pTü32.

Figure 8A:
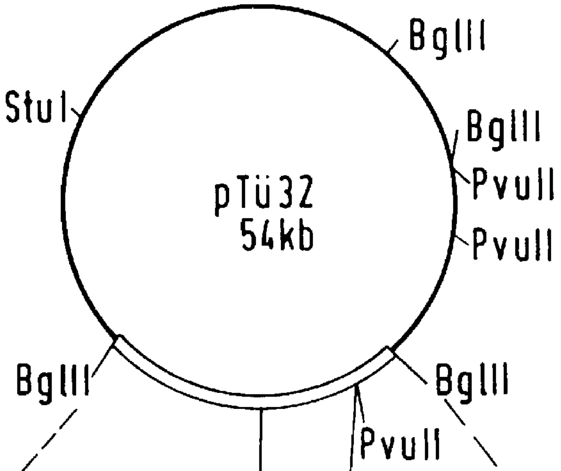
FIG. 8 is a genetic analysis of episome pTü32 of *S. epidermis* plasmid pTü32, including
Figure 8B:
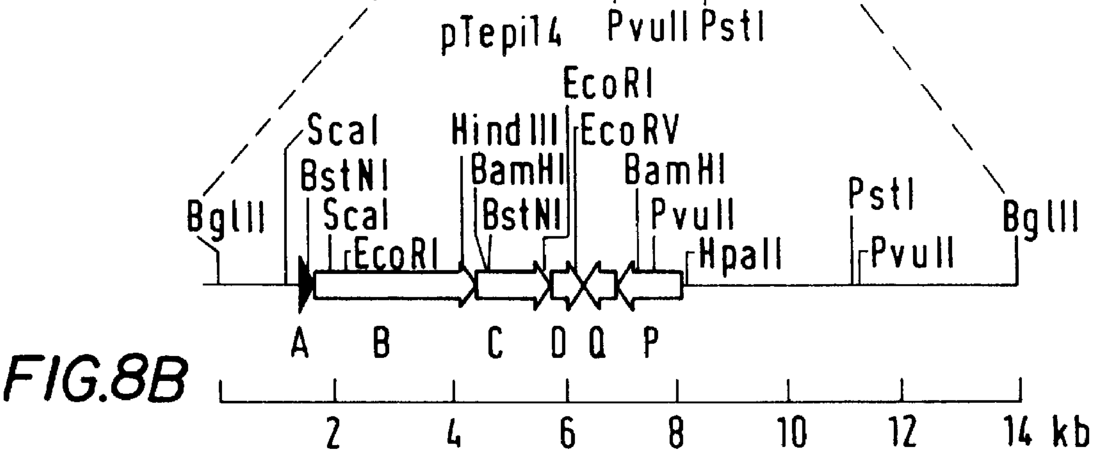
Figure 8C:
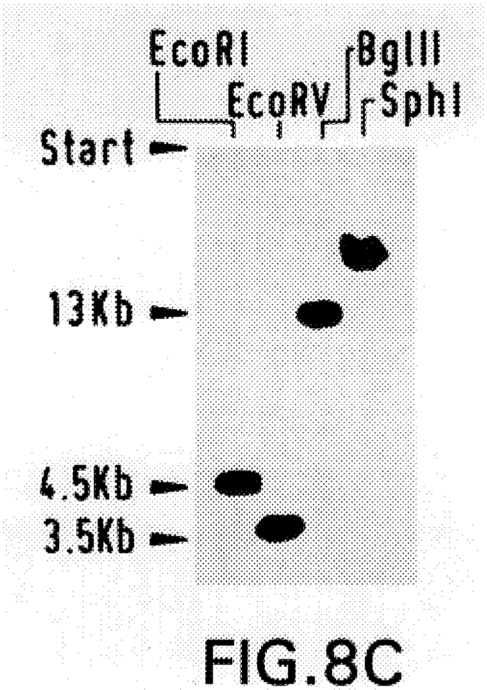

A HindIII fragment of pTü32 was cloned in pUC19 and used as a probe in Southern hybridization to identify further restriction sites near the HindIII fragment (FIG. 8C).

The 13.5 kbp BglII fragment of the 54 kbp episomal element pTü32 from *S. epidermis* was subcloned in pT181mcs to yield pTepi14 (FIG. 8A). For DNA sequencing subclones were made in the *E. coli* vector pUC19 (Yanisch-Perron el al., *Gene* 33:103–119 (1985)) and pBluescript II$^R$ (Stratagene, Heidelberg, F.R.G). Single stranded RNA probes were obtained from DNA cloned in vector pSPT18/19 (Boehringer Mannheim, Mannheim, F.R.G.).

Gene Analysis

Sequencing the DNA region adjacent to the epidermin structural gene, epi A (nucleotides 1381–1536 of SEQ ID NO:16), revealed five additional complete open reading frames epiB (nucleotides 1593–4662 of SEQ ID NO:16), epiC (nucleotides 4441–5805 of SEQ ID NO:16), epiD (nucleotides 5824–6366 of SEQ ID NO:16), epiP (nucleotides complementary to the DNA sequence 8379–6996 of SEQ ID NO:16), epiQ (nucleotides complementary to the DNA sequence 6983–6369 of SEQ ID NO:16) inside the 13.5 kbp BglII fragment of pTë32.

As can be seen in FIG. 9, directly adjacent to the sequence encoding for EpiA separated by only 50 nucleotides from the epiA ochre codon there is a large open reading frame preceded by a S/D sequence which spans 2,970 bp. A TTG codon for leucine which can also act as a translation start codon in staphylococci is in appropriate distance (86 p) to a S/D sequence. This open reading frame is designated epiB and as described herein can successfully be used for the complementation of epidermin biosynthesis mutants and an essential role in epidermin biosynthesis.

The protein coded for by epiB (SEQ ID NO:20) starting from the TTG (Leu) has a molecular weight of about 115 kDa, a net charge of −3 at pH7, and is moderately hydrophobic (41% hydrophobic residues) as may also be predicted from a hydrophilicity plot according to Kyte et al., *J. Mol. Biol.* 157:105–132 (1982).

At the 3' end of epiB no palindromine structure characteristic of transcription termination can be seen. There is, however, a 122 bp overlap with an other reading frame epiC, shifted by −1 base pair also to be seen in FIGS. 9A–E.

We have established this to be no artefact by independently cloning and sequencing the respective 47 kbp HindIII-fragment twice from two independent plasmid isolations. This was also confirmed by mutant complementation with an epiC containing fragment as described herein.

Inside the overlapping region of epiB and epiC reading frames the first TTG codon (Leu) which is only 36 bp 3' to an AGGA element serves as a translational start codon, indicating that both reading frames overlap by about 40 codons. The actual amino-terminus of the EpiC protein was determined by N-terminal sequencing. Reading frame epiC encodes a protein with 455 amino acid residues commencing with starting codon TTG (Leu). The reading frame epiD directly follows 3' to epiC with a start ATG 86p 3' to a AGGAGG S/D sequence. 3' to epiD is a classical rho dependent transcription terminator structure; epiD encodes a protein of 181 amino acid residues with ATG (Met) on start codon.

None of the proteins Epi B (SEQ ID NO:20), Epi C (SEQ ID NO:21), Epi D (SEQ ID NO:22), Epi P (SEQ ID NO:24), and Epi Q (SEQ ID NO:23) show any similarity with protein sequences filed in the protein data bases Swiss Prot and Gene Bank, and thus represent unknown types of enzymes and regulatory proteins.

Transcription of the biosynthetic genes

Single stranded RNA probes were obtained by cloning the desired fragment in a pSPT 18/19 vector system (Boehringer Mannheim, Mannheim, F.R.G.) as described above.

Two transcripts differing considerably in size were obtained as illustrated in FIG. 10. A hybridization probe specific of epiA identified a small transcript of about 300 bp. Transcripts of similar size were also found for the lantibiotics nisin (Buchmann el al., *J. Biol. Chem.* 263:16260–16266 (1988)) and subtilin (Banerjee et al., *J. Biol. Chem.* 263:9508–9514 (1988)). Additionally a large transcript of approximately 5 kb can be identified with a hybridization probe specific for epiB. As there were no *E. coli*-like promoter sequences in front of epiB, whereas appropriate sequences were located 5' to epiA it can be seen that the epiA promoter acts as a promoter for a polycistronic mRNA.

Downstream open reading frames

The open reading frames epiP and epiQ are located on the opposite DNA to epiB, C and D with epiQ sharing a termination structure with epiD a perfect hairpin with a 6 bp loop.

Exactly within this loop structure the TAA stop codons for both reading frames epiD and epiQ share two of three nucleotides.

The epiP reading frame starts with an ATG codon which is in appropriate distance (6 bp) to a S/D sequence. Taking the ATG codon as the translational start of epiP a protein of 461 amino acid residues with molecular weight of 51.8 kD. epiP shares characteristic homologies with the conserved amino acid motives of serine proteases (see FIG. 11) indicating that epiP is implicated in cleaving the natured lantibiotic from the modified prepeptide.

The epiQ reading frame also starts with an ATG codon and encodes 205 amino acid residues (FIGS. 9A–E). A S/D sequence is present 6 bp distance to the ATG codon and a molecular weight of 243 kD can be deduced from the DNA sequence. The epiQ protein shares characteristic homologies with PhoB (see FIG. 12) which is a positive regulatory factor for the phosphate regulatory of *E. coli* so that epiQ is implicated as a regulatory factor in lantibiotic synthesis.

Preceding epiP is an *E. coli*-like −10 region (5'-TATAAA) 12 bp in front of the S/D sequence which may serve as a promoter in staphylococci. The distance between the epiP stop codon and the ATG start codon of epiQ is only 10 nucleotides and the epiQ S/D sequence overlaps with the epiP termination codon as shown in FIG. 9.

5' to epiA, B, C, D a further reading frame with opposite orientation can be seen which potentially encodes a maximum of 148 amino acids. A characteristic S/D sequence is present but none of the previously described start codons for staphylococci (ATG, TTG, GTG). With a −1 frame shift a further reading frame follows which exceeds the isolated BglII fragment illustrated in FIGS. 9A–9E.

These two reading frames are homologous to a single open reading frame, gdmY, identified adjacent to the structural gene of gallidermin (Schnell, N., *Biosynthese der Peptid-Antibiotika Epidermin und Gallidermin*; Doctoral Thesis, University of Tubingen, F.R.G. (1989)). The homologous reading frames on the *S. epidermis* plasmid are designated epiY' and epiY".

Example 4

*S. carnosus* TM300 was transformed with the plasmid pTepi14, prepared as described above, using standard techniques. The transformed strain was then grown on BM-media (see above).

The resulting transformants were found to be capable of inhibiting the epidermin sensitive tester strain *Micrococcus luteus* ATCC9341. In this assay 1 ml of an overnight culture of *M. luteus* (adjusted to an $OD_{578}$ of 1.0) was added to 500 ml molten BM-Agar. Petri dishes usually contained 10 ml of this agar. Dilutions of *S. epidermis* cultures were spread on the agar surface. Epidermin positive colonies were detected as a zero of growth inhibition of *M. luteus* around the colonies.

Cells were grown on 3% meat extract, 3.8% malt extract, 0.6% $CaCl_2 \times 2H_2O$ and 4.6% NaCl, pH6.5. According to the transformation used, tetracycline or chloramphenicol was added. After 24 h incubation (37° C. 160 rpm) in 500 ml Erlenmeyer flasks with one extension containing 100 ml medium, the culture both was centrifuged at 10,000 rpm in a Servall centrifuge for 10 min.

Supernatants of liquid transformant cultures were purified by adsorption chromatography (XAD1180, impurities eluted with water/methanol (1:1) and epidermin eluted with methanol/0.1N HCl (9:1); after evaporation the eluate was adjusted with 3N NaOH to pH 3.5 and filled up with water to 10 ml) and detected by HPLC chromatography. The inhibitory activity co-migrated with mature epidermin at 6.75/6.76 min (see FIGS. 13A and 13B). Untransformed *S. carnosus* culture media treated similarly had no peak in this elution region (6.72 to 6.79 min, FIG. 13C). These results clearly confirmed the heterologous epidermin biosynthesis in *S. carnosus* and demonstrated that pTepi14 contains all information necessary for epidermin biosynthesis.

As pTepi14 contains the 13.5 kbp BglII fragment this indicates that the epiY' and epiY" reading frames are not necessary for the production of epidermin in this system as epiY' lacks a translational start codon and epiY" is incomplete on this fragment.

Example 5

A number of epimutants of *S. epidermis* Tü3298 were prepared by ethylmethane sulfonate (EMS) mutagenesis. This procedure was carried out according to Miller, J. H., *Experiments in molecular genetics*, Cold Spring Harbor Laboratory; Cold Spring Harbor, N.Y. (1972). The mutants were screened for epidermin production, or lack of epidermin production using the *M. luteus* assay described above. Epi$^-$mutants were transferred several times to test their stability. Of the 40 epi$^-$ mutants isolated, only 10 were stable; the unstable mutants produced epidermin again after several transfers. All stable epi$^-$mutants still contained plasmid pTü32 which suffered no deletions or rearrangements as tested by restriction endonuclease analysis. The 10 epi$^-$ mutants were used for complementation studies.

Various restriction fragments of plasmid pTü32 were cloned in *S. carnosus* to test for heterologous epidermin production. The fragments were inserted into plasmid vectors T181mcs and pCU1 as described above and the various ORFs which were subcloned as shown in FIG. 16B.

Cloning was first carried out in *S. carnosus* (by protoplast transformation (Gotz et al, *FEMS Microbiol. Lett.* 40:285–288 (1987)) or *E. coli* (using $CaCl_2$; Cohen et al., *Proc. Nat. Acad. Sci. USA* 69:2110–2114 (1972)) and then the recombinant plasmids were isolated and transferred into the various *S. epidermis* epi mutants by electroporation (Augustin et al., *FEMS Microbiol. Lett.* 66:203–208 (1990)). Enzymes used for molecular cloning were obtained from Boehringer Mannheim (Mannheim, F.R.G.), BRL (Eggenstein, F.R.G.) or Pharmacia (Sweden). This indirect transformation method was necessary since transformation of *S. epidermis* strains was only successful with circular covalently closed (ccc) plasmids; when ligation products were used, transformants could only be isolated occasionally.

The results of the complementation studies are summarized in Table 1.

Figure 16A:
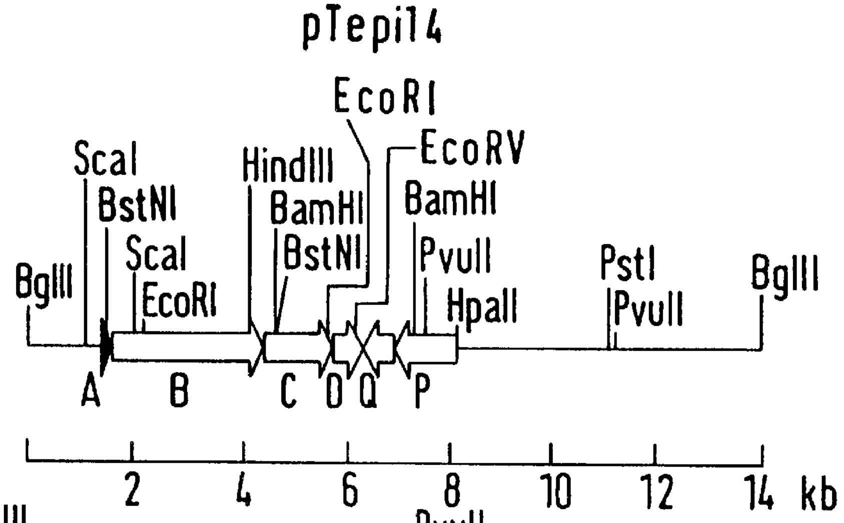
Figure 16B:
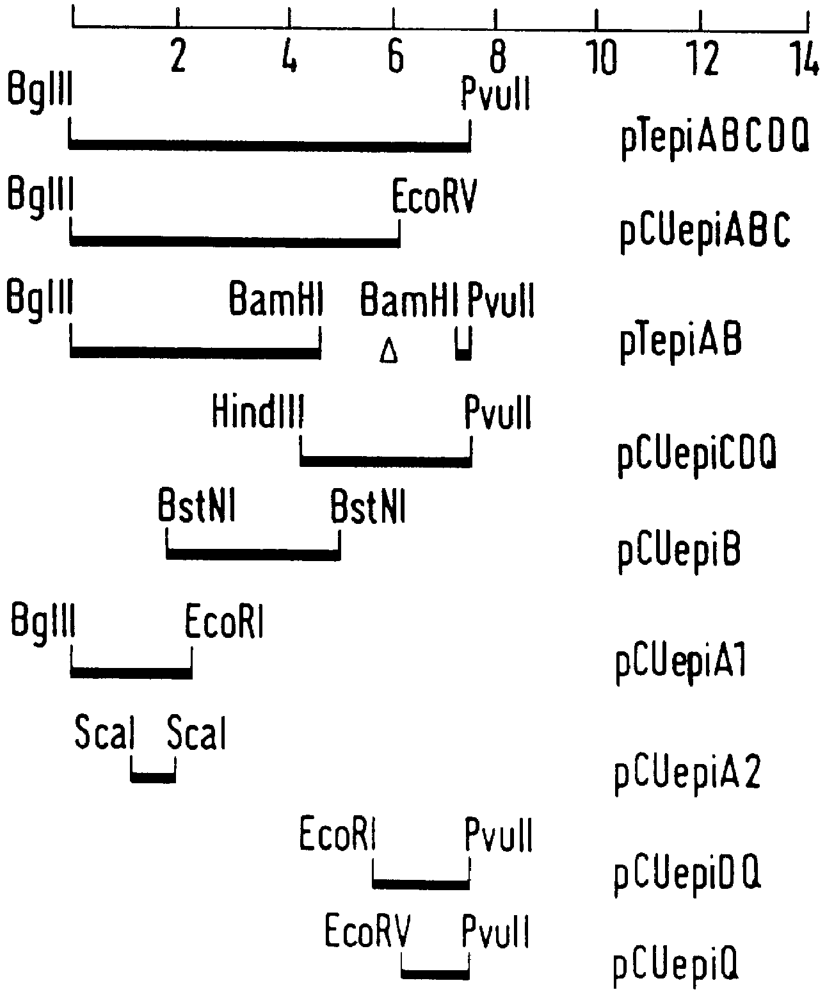

A series of plasmids were constructed which carry various epi genes (A, B, C, D, P and Q) (FIG. 16B). Two plasmids pTepi14 and pTepiABCDQ were able to complement all epi$^-$mutants. The other constructed plasmids pCUepiABC, pTepiAB, pCUepiCDQ, pCUepiB, pCUepiA$_1$, pCUepiA$_2$, pCUepiDQ and pCUepiQ contained the indicated genes.

The various plasmids were able to complement only certain classes of mutants which are classified herein as follows:

EMS 5 and 6—epiA mutants,
EMS 18, 33 and 45—epiB mutants,
EMS 12, 13, 19 and 39—epiC mutants,
EMS 11—epiD mutant.

The results as shown below indicate at least that the four ORFs epiA, B, C and D are required for epidermin biosynthesis.

The plasmid pCUepiA$_1$ carries the structural gene epiA as the only complete ORF and an additional 1400 bp upstream and 602 bp downstream, the latter encoding 190 amino acids of the epiB N-terminus. Transformation using pCUepiA$_1$ resulted in the complementation of the epidermin mutants EMS 5 and 6 identifying them as epiA mutants. The smaller epiA-containing ScaI fragment cloned in both orientations in pCUepiA$_2$ failed to complement the epi$^-$mutants as the epiA promoter was cut by this enzyme.

pCUepiB carries a BstN1 fragment containing the complete epiB and an upstream region of 100 bp which includes 75 bp of the 3' terminus of epiA; the epiA promoter is missing. Transformation with pCUepiB failed to complement any *S. epidermis* mutant to epidermin production, indicating that epiB lacks its own promoter and is very likely co-transcribed from the epiA promoter.

This is in agreement with the results obtained with pTepiAB (FIG. 16B; Table 1) which contains epiA promoter and the complete epiA and B genes and the use of which complements both the epiA and epiB mutants.

Plasmid pCUepiCDQ was able to complement both epiC and epiD mutants and plasmid pCUepiDQ was only able to complement the epiD mutant (Table 1). The complementation was independent of the orientation of the cloned DNA fragment These results show that both epic and epiD possess their own promoters.

TABLE 1

Epidermin production by non-producing *S. epidermidis* mutants after transformatin with various pTepi14 DNA fragments

| | Complementation with | | | | | | | | | | |
|---|---|---|---|---|---|---|---|---|---|---|---|
| Mutant | pTepi 14 | pTepi ABCDQ | pCUepi ABC | pTepi AB | pCUepi A1 | pCUepi A2 | pCUepi CDQ | pCUepi DQ | pCUepi Q | pCUepi B | Mutation locus |
| EMS 5 | + | + | + | + | + | − | − | − | − | − | epiA |
| EMS 6 | + | + | + | + | + | − | − | − | − | − | epiA |
| EMS 11 | + | + | − | − | − | − | + | + | − | − | epiD |
| EMS 12 | + | + | + | − | − | − | + | − | − | − | eipC |
| EMS 13 | + | + | + | − | − | − | + | − | − | − | epiC |
| EMS 18 | + | + | + | + | − | − | − | − | − | − | epiB |
| EMS 19 | + | + | + | − | − | − | + | − | − | − | epiC |
| EMS 33 | + | + | + | + | − | − | − | − | − | − | epiB |
| EMS 39 | + | + | + | − | − | − | + | − | − | − | epiC |
| EMS 45 | + | + | + | + | − | − | − | − | − | − | epiB |

pCU: Fragments cloned in pCU1; pT: Fragments cloned in pT181mcs
+ complementation (epidermin production; − no complementation)

Example 6

The epiA mutated pTü32 derivatives were isolated from EMS 5 and 6 and the respective epiA ORFs were sequenced. Both plasmids had point mutations within epiA; in the EMS 5 plasmid the codon AGT ($Ser^3$) was changed to AAT ($Asn^3$) and in the EMS 6 plasmid the codon GGA ($Gly^{10}$) was changed to GAA ($Gln^{10}$); both these mutations were located at crucial sites within the unmodified epidermin.

Example 7

An epiB (on a BstN1-fragment) was put under the control of the promoter on plasmid pPS4 (FIG. 17). The resulting plasmid pPS4epiB was able to complement the epiB mutants EMS 18, 33 and 45. A plasmid containing epiB in the opposite orientation did not complement the mutations. This also establishes that pCUepiB was unable to complement any of the EMS mutants, because the epiA promoter is missing.

Example 8

As described above, the presence of pTepi4 (FIG. 16A) resulted in epidermin biosynthesis in *S. carnosus*; however, the presence of pTepiABCDq did not. The minimum size of DNA required which leads to heterologous epidermin expression in *S. carnosus* was determined by complementing *S. carnosus* (pTepiABCDQ) with distally located DNA fragments (FIG. 18). Transformation of *S. carnosus* (pTepiABCDQ) with plasmids pCA44–90, pCA44–91 and pCA44–92 led to epidermin production, pCA44–92 containing the complete epiQ and epiP ORFs consisted of the smallest DNA fragment able to complement epidermin production. These results indicate that the epidermin biosynthetic genes are clustered within an 8 kb DNA fragment containing the six ORFs; epiA, B, C, D, Q and P and that no other genes are involved in epidermin biosynthesis.

In these examples staphyloccal plasmid DNA was prepared by the cleaved lysate method (Makino et al., *J. Mol. Biol.* 190:37–44 (1986)). Cells were lysed by the addition of lysostaphin (8 μg/ml) and the DNA was isolated by CsCl-centrifugation. *E. coli* supercoiled plasmid DNA was prepared by the modified alkaline lysis method (Birnboim et al., *Nucl. Acid Res.* 7:1513–1518 (1979)).

The DNA sequence of the PCR-amplified epiA-containing fragment and the two mutated epiA regions of the *S. epidermis* mutants, EMS 5 and 6, was determined by double-stranded DNA sequencing using the dideoxy procedure (McMaster et al., *Proc. Natl. Acad. Sci. USA* 74:4835–4839 (1977)), the "sequence" list of Pharmacia and ($\alpha$-$^{35}$S)-dATP from Amersham. Primers used for DNA sequencing and PCR amplification were synthesized using the DNA-synthesizer of Applied Biosystems. The sequences of the two primers for PCR amplification of epiA are as follows:

Primer a) binds in front of the RBS of epiA and primer b) after the epiA stop codon. These bases indicated by bold letters represent (shown in brackets) used to create BamHI sites in front and at the end of epiA; the epiA promoter is absent in the amplified DNA fragment.

For determination of the DNA sequence of the mutated epiA in the mutants EMS 5 and 6, plasmid pTü32 was isolated and the DNA region was amplified by PCR using another set of DNA primers binding upstream of the postulated epiA promoter region (5'-GGTTTGGTTATTTTCC-3') and downstream of the stop codon (5'-CCTCAAAATTAAGACAGAGCCTC-3'); the DNA sequence of epiA is also shown in Schnell el al., *Nature* (*Lond.*) 333:276–278 (1988).

Example 9

The epi D gene was isolated from the plasmid pTepi 14, multiplied by PCR amplification and cloned into the StuI-restriction site of vector pIH902 (New England, Biolabs) by "blunt end" ligation, with the result that the epi D gene is fused without any intervening base pairs immediately at the Factor Xa-cleavage site of vector pIH902, which was then transformed into *E. coli.*

Cultivation of the *E. coli* resulted in expression of the enzyme Epi D fused to the Maltose binding protein of *E. coli*. The resulting fusion protein was purified by affinity chromatography on Amylose column material.

It was found that the enzyme epiD could be cleaved from the fusion protein in low yield by means of Factor Xa. A modification of the amino acid sequence at the cleavage region will enable the cleavage rate to be improved.

The fusion protein was sequenced at the DNA level from the fusion position to the 3' end of epiD. The epiD sequence corresponded to the wild type sequence of *S. epidermis.*

From the foregoing description, one skilled in the art can easily ascertain the essential characteristics of this invention, and without departing from the spirit and scope thereof can make various changes and modifications of the invention to adapt it to various usages and conditions.

a) 5' - GGGTTTTAGG (TA )ATCCTTTTTAATAAATTTTTAGGAG - 3' b) 5' - CCTCAAAATTAAGACG (A )GAT (G )CCTCTATTGAAGCCC - 3'

What is claimed is:

1. A method for preparing an isolated gallidermin comprising (a) culturing a host cell transformed by a plasmid comprising a nucleotide sequence which codes for a gallidermin precursor, wherein (I) said gallidermin precursor is foreign to the host;

(ii) the host cell comprises an epidermin multi-enzyme complex; and (b) isolating gallidermin.

2. A method according to claim 1, wherein said host is selected from *Streptococcus lactis, Bacillus subtilis, Streptomyces cinnamoneous*, Streptomyces sp., *Streptoverticullum griseoverticillum, Staphylococcus epidermidis, Staphylococcus epidermin* strain 5 or *Staphylococcus gallinarium.*

3. An isolated Epi protein selected from Epi B, Epi C, Epi D, Epi P or Epi Q, said isolated Epi protein having an Epi protein enzymatic activity in the synthesis of epidermin.

4. An isolated Epi protein according to claim 3, wherein said Epi protein is Epi B protein having Epi B enzymatic activity in the synthesis of epidermin.

5. An isolated Epi protein according to claim 3, wherein said Epi protein is Epi C protein having Epi C enzymatic activity in the synthesis of epidermin.

6. An isolated Epi protein according to claim 3, wherein said Epi protein is Epi D protein having Epi D enzymatic activity in the synthesis of epidermin.

7. An isolated Epi protein according to claim 3, wherein said Epi protein is Epi P protein having Epi P enzymatic activity in the synthesis of epidermin.

8. An isolated Epi protein according to claim 3, wherein said Epi protein is Epi Q protein having Epi Q enzymatic activity in the synthesis of epidermin.

9. An isolated Epi B protein according to claim 4, having the amino acid sequence set forth in SEQ ID NO:20.

10. An isolated Epi C protein according to claim 5, having the amino acid sequence set forth in SEQ ID NO:21.

11. An isolated Epi D protein according to claim 6, having the amino acid sequence set forth in SEQ ID NO:22.

12. An isolated Epi P protein according to claim 7, having the amino acid sequence set forth in SEQ ID NO:24.

13. An isolated Epi Q protein according to claim 8, having the amino acid sequence set forth in SEQ ID NO:23.

14. A composition, comprising (a) at least one isolated Epi protein according to claim 3; and (b) a carrier or diluent.

15. A fusion protein comprising (a) at least one isolated Epi protein according to claim 3; and (b) an auxiliary protein.

16. A fusion protein, comprising at least one isolated Epi protein according to claim 3, said Epi protein fused to an auxiliary protein such that the junction between the Epi protein and the auxiliary protein can be cleaved by an enzyme.

17. A fusion protein according to claim 16, wherein said auxiliary protein facilitates secretion of the fusion protein from a selected host.

18. A fusion protein according to claim 16, wherein the auxiliary protein facilitates purification by affinity chromatography.

19. A fusion protein according to claim 16, wherein the auxiliary protein is the Maltose binding protein from *E. coli.*

20. A method of claim 1 wherein said nucleotide sequence is contained in plasmid pCUgdm1.

21. An isolated gallidermin encoded by a nucleotide sequence contained in plasmid pCUgdm1.

* * * * *

SEQUENCE LISTING ( 1 ) GENERAL INFORMATION:

( i i i ) NUMBER OF SEQUENCES: 42

( 2 ) INFORMATION FOR SEQ ID NO:1:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:1:

CACATCCAGG AGTAC 15

( 2 ) INFORMATION FOR SEQ ID NO:2:

( i ) SEQUENCE CHARACTERISTICS:
( A ) LENGTH: 14 base pairs
( B ) TYPE: nucleic acid
( C ) STRANDEDNESS: single
( D ) TOPOLOGY: linear ( x i ) SEQUENCE DESCRIPTION: SEQ ID NO:2:

GTRCADATRA AYTT 14

( 2 ) INFORMATION FOR SEQ ID NO:3:

( i ) SEQUENCE CHARACTERISTICS:
( A ) LENGTH: 5 amino acids
( B ) TYPE: amino acid
( D ) TOPOLOGY: linear ( x i ) SEQUENCE DESCRIPTION: SEQ ID NO:3:

Lys Phe Ile Cys Thr
1 5

( 2 ) INFORMATION FOR SEQ ID NO:4:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:4:

Pro Xaa Gly Pro
1

( 2 ) INFORMATION FOR SEQ ID NO:5:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:5:

CACATCCAGG AGTAC 15

( 2 ) INFORMATION FOR SEQ ID NO:6:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear -continued ( x i ) SEQUENCE DESCRIPTION: SEQ ID NO:6:

GGGTTTTAGD ATCCTTTTTA ATAAATTTTT AGGAG 35

( 2 ) INFORMATION FOR SEQ ID NO:7:

( i ) SEQUENCE CHARACTERISTICS:
( A ) LENGTH: 34 base pairs
( B ) TYPE: nucleic acid
( C ) STRANDEDNESS: single
( D ) TOPOLOGY: linear ( x i ) SEQUENCE DESCRIPTION: SEQ ID NO:7:

CCTCAAAATT AAGACRGAKC CTCTATTGAA GCCC 34

( 2 ) INFORMATION FOR SEQ ID NO:8:

( i ) SEQUENCE CHARACTERISTICS:
( A ) LENGTH: 16 base pairs
( B ) TYPE: nucleic acid
( C ) STRANDEDNESS: single
( D ) TOPOLOGY: linear ( x i ) SEQUENCE DESCRIPTION: SEQ ID NO:8:

GGTTTGGTTA TTTTCC 16

( 2 ) INFORMATION FOR SEQ ID NO:9:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( x i ) SEQUENCE DESCRIPTION: SEQ ID NO:9:

CCTCAAAATT AAGACAGAGC CTC 23

( 2 ) INFORMATION FOR SEQ ID NO:10:

( i ) SEQUENCE CHARACTERISTICS:
( A ) LENGTH: 423 base pairs
( B ) TYPE: nucleic acid
( C ) STRANDEDNESS: single
( D ) TOPOLOGY: linear ( i x ) FEATURE:
( A ) NAME/KEY: CDS
( B ) LOCATION: 162..320

( x i ) SEQUENCE DESCRIPTION: SEQ ID NO:10:

```
TTTAAACTTT ATATCATTAA TATAATGTTT AGGAAAAGTA GAAGAAAATT ACACTTTTGT      60

AATTTTCTGA ATATACATAG TATTTATTTT GGGGGAGTAC TAAAATAATA ATTGAAAAGG     120

GTTTTATAAT CCTTTTTAAT AAATTTTTAG GAGTGTTTAA A ATG GAA GCA GTA         173
                                              Met Glu Ala Val
                                               1

AAA GAA AAA AAT GAT CTT TTT AAT CTT GAT GTT AAA GTT AAT GCA AAA      221
Lys Glu Lys Asn Asp Leu Phe Asn Leu Asp Val Lys Val Asn Ala Lys
  5                  10                  15                  20

GAA TCT AAC GAT TCA GGA GCT GAA CCA AGA ATT GCT AGT AAA TTT ATA      269
Glu Ser Asn Asp Ser Gly Ala Glu Pro Arg Ile Ala Ser Lys Phe Ile
                 25                  30                  35

TGT ACT CCT GGA TGT GCA AAA ACA GGT AGT TTT AAC AGT TAT TGT TGT      317
Cys Thr Pro Gly Cys Ala Lys Thr Gly Ser Phe Asn Ser Tyr Cys Cys
             40                  45                  50

TAATTCAGAA GAATTAGATT GGCAGGGCTT CAATAGAGGC TCTGTCTTAA TTTTGAGGTG     377
```

AAATAGAATT GGATAATATA TTTGTTCCAT CGAATATATA TATGGT 423

(2) INFORMATION FOR SEQ ID NO:11:

(i) SEQUENCE CHARACTERISTICS:
(A) LENGTH: 52 amino acids
(B) TYPE: amino acid
(D) TOPOLOGY: linear (ii) MOLECULE TYPE: protein (xi) SEQUENCE DESCRIPTION: SEQ ID NO:11:

```
Met Glu Ala Val Lys Glu Lys Asn Asp Leu Phe Asn Leu Asp Val Lys
1               5                   10                  15

Val Asn Ala Lys Glu Ser Asn Asp Ser Gly Ala Glu Pro Arg Ile Ala
            20                  25                  30

Ser Lys Phe Ile Cys Thr Pro Gly Cys Ala Lys Thr Gly Ser Phe Asn
        35                  40                  45

Ser Tyr Cys Cys
    50
```

(2) INFORMATION FOR SEQ ID NO:12:

(i) SEQUENCE CHARACTERISTICS:
(A) LENGTH: 52 amino acids
(B) TYPE: amino acid
(D) TOPOLOGY: linear (ii) MOLECULE TYPE: protein (xi) SEQUENCE DESCRIPTION: SEQ ID NO:12:

```
Asn Glu Ala Val Lys Glu Lys Asn Asp Leu Phe Asn Leu Asp Val Lys
1               5                   10                  15

Val Asn Ala Lys Glu Ser Asn Asp Ser Gly Ala Glu Pro Arg Ile Ala
            20                  25                  30

Ser Lys Phe Ile Cys Thr Pro Gly Cys Ala Lys Thr Gly Ser Phe Asn
        35                  40                  45

Ser Tyr Cys Cys
    50
```

(2) INFORMATION FOR SEQ ID NO:13:

(i) SEQUENCE CHARACTERISTICS:
(A) LENGTH: 51 amino acids
(B) TYPE: amino acid
(D) TOPOLOGY: linear (ix) FEATURE:
(A) NAME/KEY: Peptide
(B) LOCATION: 38
(D) OTHER INFORMATION: /label=Peptide
/ note= "The amino acid labelled "Xaa"at position 38 is connected to alanine at position 41 via a sulfide bridge. This connection creates the amino acid (2S,3S,6R)-3-methyl-lanthionine. See figure 5."

(ix) FEATURE:
(A) NAME/KEY: Peptide
(B) LOCATION: 44
(D) OTHER INFORMATION: /label=Peptide
/ note= "The amino acid labelled "Xaa"at position 44 is dehydrobutyrine."

(ix) FEATURE:
(A) NAME/KEY: Peptide
(B) LOCATION: 33
(D) OTHER INFORMATION: /label=Peptide
/ note= "Two sulfide bridges, one connecting amino acids at positions 33 and 37 and another connecting positions 46 and 51 create the amino acid meso- lanthionine."

( i x ) FEATURE:
( A ) NAME/KEY: Peptide
( B ) LOCATION: 49
( D ) OTHER INFORMATION: /label=Peptide
/ note= "The amino acids at positions 49 and 51 are connected by a S(CH)2NH bridge."

( x i ) SEQUENCE DESCRIPTION: SEQ ID NO:13:

```
Asn Glu Ala Val Lys Glu Lys Asn Asp Leu Phe Asn Leu Asp Val Lys
1               5                   10                  15

Val Asn Ala Lys Glu Ser Asn Asp Ser Gly Ala Glu Pro Arg Ile Ala
            20                  25                  30

Ala Lys Phe Ile Ala Xaa Pro Gly Ala Ala Lys Xaa Gly Ala Phe Asn
        35                  40                  45

Ala Tyr Ala
    50
```

( 2 ) INFORMATION FOR SEQ ID NO:14:

( i ) SEQUENCE CHARACTERISTICS:
( A ) LENGTH: 21 amino acids
( B ) TYPE: amino acid
( D ) TOPOLOGY: linear ( i x ) FEATURE:
( A ) NAME/KEY: Peptide
( B ) LOCATION: 8
( D ) OTHER INFORMATION: /label=Peptide
/ note= "The amino acid labelled "Xaa"at position 8 is connected to alanine at position 11 via a sulfide bridge. This connection creates the amino acid (2S,3S,6R)-3-methyl-lanthionine. See figure 5."

( i x ) FEATURE:
( A ) NAME/KEY: Peptide
( B ) LOCATION: 14
( D ) OTHER INFORMATION: /label=Peptide
/ note= "The amino acid labelled "Xaa"at position 14 is dehydrobutyrine."

( i x ) FEATURE:
( A ) NAME/KEY: Peptide
( B ) LOCATION: 3
( D ) OTHER INFORMATION: /label=Peptide
/ note= "Two sulfide bridges, one connecting amino acids at positions 3 and 7 and another connecting positions 16 and 21 create the amino acid meso- lanthionine."

( i x ) FEATURE:
( A ) NAME/KEY: Peptide
( B ) LOCATION: 19
( D ) OTHER INFORMATION: /label=Peptide
/ note= "The amino acids at positions 19 and 21 are connected by a S(CH)2NH bridge."

( x i ) SEQUENCE DESCRIPTION: SEQ ID NO:14:

```
Ile Ala Ala Lys Phe Ile Ala Xaa Pro Gly Ala Ala Lys Xaa Gly Ala
1               5                   10                  15

Phe Asn Ala Tyr Ala
            20
```

( 2 ) INFORMATION FOR SEQ ID NO:15:

( i ) SEQUENCE CHARACTERISTICS:
( A ) LENGTH: 34 amino acids
( B ) TYPE: amino acid
( D ) TOPOLOGY: linear ( i x ) FEATURE:
( A ) NAME/KEY: Peptide
( B ) LOCATION: 2
( D ) OTHER INFORMATION: /label=Peptide
/ note= "The amino acid labelled "Xaa"at position 2 is dehydrobutyrine."

( i x ) FEATURE:
( A ) NAME/KEY: Peptide
( B ) LOCATION: 3
( D ) OTHER INFORMATION: /label=Peptide
/ note= "The amino acids at positions 3 and 7 are connected via a sulfide bridge."

( i x ) FEATURE:
( A ) NAME/KEY: Peptide
( B ) LOCATION: 5
( D ) OTHER INFORMATION: /label=Peptide
/ note= "The amino acid labelled "Xaa"at position 5 is dehydroalanine."

( i x ) FEATURE:
( A ) NAME/KEY: Peptide
( B ) LOCATION: 8
( D ) OTHER INFORMATION: /label=Peptide
/ note= "The amino acid labelled "Xaa"at position 8 is connected to alanine at position 11 via a sulfide bridge. This connection creates the amino acid (2S,3S,6R)-3-methyl-lanthionine. See figure 5."

( i x ) FEATURE:
( A ) NAME/KEY: Peptide
( B ) LOCATION: 13
( D ) OTHER INFORMATION: /label=Peptide
/ note= "The amino acid labelled "Xaa"at position 13 is connected to alanine at position 19 via a sulfide bridge. This connection creates the amino acid (2S,3S,6R)-3-methyl-lanthionine. See figure 5."

( i x ) FEATURE:
( A ) NAME/KEY: Peptide
( B ) LOCATION: 23
( D ) OTHER INFORMATION: /label=Peptide
/ note= "The amino acid labelled "Xaa"at position 23 is connected to alanine at position 26 via a sulfide bridge. This connection creates the amino acid (2S,3S,6R)-3-methyl-lanthionine. See figure 5."

( i x ) FEATURE:
( A ) NAME/KEY: Peptide
( B ) LOCATION: 25
( D ) OTHER INFORMATION: /label=Peptide
/ note= "The amino acid labelled "Xaa"at position 25 is connected to alanine at position 28 via a sulfide bridge. This connection creates the amino acid (2S,3S,6R)-3-methyl-lanthionine. See figure 5."

( i x ) FEATURE:
( A ) NAME/KEY: Peptide
( B ) LOCATION: 33
( D ) OTHER INFORMATION: /label=Peptide
/ note= "The amino acid labelled "Xaa"at position 33 is dehydroalanine."

( x i ) SEQUENCE DESCRIPTION: SEQ ID NO:15:

```
Ile Xaa Ala Ile Xaa Leu Ala Xaa Pro Gly Ala Lys Xaa Gly Ala Leu
1               5                   10                  15

Met Gly Ala Asn Met Lys Xaa Ala Xaa Ala His Ala Ser Ile His Val
            20                  25                  30

Xaa Lys
```

( 2 ) INFORMATION FOR SEQ ID NO:16:

( i ) SEQUENCE CHARACTERISTICS:
( A ) LENGTH: 8700 base pairs ( B ) TYPE: nucleic acid
( C ) STRANDEDNESS: single
( D ) TOPOLOGY: linear ( x i ) SEQUENCE DESCRIPTION: SEQ ID NO:16:

```
AGATCTTGTG TTATATAACT AAACAAATTT CTCCATTCGT ATTTAGAAAA TTGACTTTTA     60
TCAAGTTTAT CCAAATATAT ATTTCCAGTA TATTCTGTAT TTAACCCAGC TAATATATTT    120
AATAATGTAC TTTTTCCACA CCCACTTTCA CCTATAATAT TGTAGATATA ACCTTTATGA    180
AGATCCAAAC TTATAGAATT TATTATTTGT TTATTGTCTT TTGTGAAGTT CAAATCATTT    240
ATTTCCATTT TTTGAACAAA GTTATTGTAA GTTGTTTTAA TAGTTAATAC CTCTTCTGGT    300
TCTTTATTTA TTTTTAAAAT TCTATCTGAA GATCCAATTG CTCGTTGTAC TTCCGTCCAA    360
TAAGATGTAA TAGATACTAT TGGATTAATA ATTTGAAATA AATATAAAAC ATAAGCAAAC    420
ATATCTCCGC TTTTCATCAT ATTATTTTCC ATTAAGTAAT AACCCAAAAA TAAAATACCA    480
AAAATGTTAA TAAATAGAAT TAAGTTCATA ATTGGTTCGA AAAAAGATAA TACTTTGATC    540
TTATGTAACT CTATATCGAA TATATTTTTT AATAGGGTAT AGTTTTTTAT TTTTTCGATA    600
TTATATGTAC TTAAAGTTTT TATTAATTTT ATTGTAGATA ATCTATTACT ATAATAAGAA    660
GATAATTTAG CAGTAGCTTC TTGAGATTTA CTTGATACTC TTTTCATTAT ATTTCCTATA    720
GGTAGTATTA CAATTATCAA TATAGGTAAT GTACACACTA AATATAATGT CAAGGTTTTG    780
TTAATTATAT ATAAAAATAT TAGTGATACT ATAACTGAAA ATAAATTCTA CAGAAAAAAC    840
TCTAGTTATG TTCATAGTAT CGTTTACTAA CCTACTAGTT AAGTTACTTG CTGAGTTTTT    900
TAAGTGAAAA CTATAAGGTA ACTTTATCAC TTTATTCCAT GTAACACTTC TAATGTTTTG    960
TATTATTTTT TGACCTATAT ATCCAAGAAT ATAAGTAGAA ACACCAGAAA ATATTAAAGT   1020
CAGACCAAAA CATATAATAA TGATTACAAT TTTATCTGTT GATAAGCTAG ATTTGTTTAA   1080
GGCATTTCTA ATTATTAAAG GAATGTATAA TGAAAAACTA GTTCCAATCA AACTAAATAT   1140
TAGTCCAATA CTTAAAAGTA GAGTGTTAGG TTTGGTTATT TTCCATAAAT CATATAGACC   1200
TTTGATAATA TCATCACCTT TTAAACTTTA TATCATTAAT ATAATGTTTA GGAAAAGTAG   1260
AAGAAAATTA CACTTTTGTA ATTTTCTGAA TATACATAGT ATTTATTTTG GGGGAGTACT   1320
AAAATAATAA TTGAAAAGGG TTTTATAATC CTTTTTAATA AATTTTTAGG AGTGTTTAAA   1380
ATGGAAGCAG TAAAAGAAAA AAATGATCTT TTTAATCTTG ATGTTAAAGT TAATGCAAAA   1440
GAATCTAACG ATTCAGGAGC TGAACCAAGA ATTGCTAGTA AATTTATATG TACTCCTGGA   1500
TGTGCAAAAA CAGGTAGTTT TAACAGTTAT TGTTGTTAAT TCAGAAGAAT TAGATTGGCA   1560
GGGCTTCAAT AGAGGCTCTG TCTTAATTTT GAGGTGAAAT AGAATTGGAT AATATATTTG   1620
TTCCATCGAA TATATATATG GTAAGAACTC CTATATTTTC AATTGAATTA TATAATCAAT   1680
TCTTAAAATC TGACAATATA GATTATGACT TAATTTTACA AAACGATATT TTTAAAGAAT   1740
CTATAATGAC AACGACATAT AATCTTTATC AAAGTATTGG CAAAATAGAC TGGGAAAAGG   1800
ATAATAAAAA AACCAGAAAT GTAAAAGAAA GTTTATTAAA ATATCTCATA AGAATGAGTA   1860
CTAGAAGTAC ACCATATGGA ATGCTAAGCG GTGTAGCTTT AGGGGAATTT AGTGAAAATA   1920
ATAATATTAA AATTAAGGAC TCTTCGTTTC ATAAAAAAGA TGTAAAAATA GATGGGCAAT   1980
GGTTATATAA ATTAGTCCAT TATTTAGAAA GCGATTACAC ATATTATAAA GACAGTTTTG   2040
TCATATGGAA TCAACAAAAT TATATTTATA ACAATCGTTT ATATTTAGAT AATAATTCAT   2100
CAATCACTGA AAATAAAAGA AATGATGTAT TATCTGTCAA ATACAATTCT ATATTAGTGT   2160
TTATACATGA GAATTCTAAA AAAAATATTA CTTATGAAGA ACTTGTACAA TTGATATCTA   2220
```

-continued

```
GTAAGTACAG TATAGAAAAT AAAGAAGAAG TAAAAGTATT TGTTCAAGAA CTCATAAATA 2280
AAGAAATTAT ATTTTCTGAT TTGAGACCTA CATTAGAGAA TAAAAATCCT TTAGATTACA 2340
TTATTAATAG TTTAAATCCA AAAAATAGTT TAGTTGGAAC ACTTATTAAT ATTTCTAATG 2400
AAATTACAAA ATATTCTAAA ATGCCTTTAG GAAAAGGAGA ATATAAATAT TTAGATATTG 2460
TTAATTTAAT GTCACAATTA TTTGTTTCTA AAAACTATTT GCAAATAGAT ACCTATATAG 2520
ATTATTCAAG AAATGAATTA AAACAAAGTT TAGCTGATAA TATTAGTGAA GCAGCATATA 2580
TTCTCTGGTT ATTATCTCCT AATCATTTTG GTACAAAAAC TATTAGGAAT TATCACGAAT 2640
TTTTTATGGA TAAATATGGA TTTGAACAAC TAGTAAATTT AAAGCAATTG CTCTCAGATA 2700
TAAATGGATT TGGCTATCCC AAAAAAGACA GTTATAGTTT TTCTAATAAC ATTGCATTTT 2760
TAAAAGAAAA GTATTTGCTT GCAATTCAAA ATAACAGCCA TATTGAAATA ACAGAAAACG 2820
ACGTTAAAAA TTTAGAAAAG AATAATACAG TTTCTAAAAT CAATGCGCCT GTTTCAACTG 2880
AAATATATAG TGAGATATAT TTTGGAAATT CAATAAAAGG TTATGAGGAT TTTGCCGTGA 2940
TAAGTCCAAT ATTAGGATCT TTTAATGCCG GTGCAACTTT TGGAAGGTTT ACGGGAAATT 3000
TCAATATAAA GAAAAAAAAT CAATTACAAA AAGAAATAGT GCATCATTAC AATAATTACA 3060
TGAATGAAAA TGGTTTAGAA ATAAGCCAAT TAAATGAAGG TCCTCTTAAC TCAAGAAATG 3120
TAAATATTTT GAATAATAAT AGAATATATA ATACTTGTTT AAATTTAAAT TTACCTAAAA 3180
GTGATATAGA TATAAATGAC ATATTTATTG GAGCTACATT TAACAAACTT TATCTATATT 3240
CTGAAAAACA TGATTCAAGA ATTGTATTCG TATCTAATTC AATGTTTAAT TATGAGTTTG 3300
GATCTGAATT ATACAAATTT TTAAGAGAAA TTTCATTTGA AAAAACAAAA TTTATACAAC 3360
CTATAACTGA AGAAGGCATT GACTCATTAC CTTTTTGTCC AAGAATTATT TATAAAAATA 3420
TTATTTTAAA ACCAGCTACT TGGAAAATAA ATTCAGAAAT GTTTTCTGAA ACTGAAAATT 3480
GGTTAAATAG GTTCGCAACT ATTAGAGAAA AATGGCATAT TCCAAAAGAT GTAATTATTG 3540
CTTTTGGAGA TAATCGATTG CTATTAAATT TATTAAATGA CAAGCATCTC ATTATACTAA 3600
AAAAAGAACT AAAAAAACAT GGTAGGATTC GAATATTAGA AAGCTTTATC AATGAATCTA 3660
ATAATGAGAG AATGTTAGAA ATTGTTACGC CATTATATAA AAAAACTAGT TTAAAAGAAC 3720
AATCTTTCAT TATACCTAAA AATAGAAATA AGCACTTCAA TAATCTTAAA GATTGGTTTT 3780
CAATTCATTT AAGTATTCCT AAAACATACC AAGATAATTT TATTCAAGAT TATCTATTAC 3840
CATTTATAAC GGAATTAAAA GTTAATAATT TTATTAATAA ATTTTTTTAC ATAAAATTTA 3900
AAGAAGATGA AGATTTTATA AAATTAAGAT TATTAAGAGA AGATGAAGAT TATTCTCAAA 3960
TTTATTCTTT CATAAAAAAT TGGAAAGATT ATTGCTTATT AAATAGTGAA TTATATGACT 4020
ATTCTATAGT TGATTATGTT CCTGAAGTAT ATAGATATGG TGGTCCACAC GTAATTGAAG 4080
ATATTGAGAA TTTTTTTATG TATGATAGTC TATTATCAAT AAATATAATA CAATCAGAGT 4140
TCAAAATTCC AAAAGAATTT ATCGTTGCTA TATCAATAGA TTTTTTATTA GATTATTTAG 4200
AAATTAATAA AAGTGAGAAA GAAGAAATTT TAATTAATAA TGCGGAAGAT TTATATCGTA 4260
GTAATGACAT AAGAGAATAT AAAAATTTAT TAGCTAAACT TACCAATCCT AAAAATGACT 4320
ATGAAATTTT AAAAAAAGAA TTTCCGAATC TTCATGAATT TCTATTTAAT AAAATTAGTA 4380
TTTTAGAAAA TCTTAAAAAG ACACTACAAA AAAGCTTATA TACTTCACGT TCTAGGATAA 4440
TTGGCAGTTT TATAAACATG CGTTGTAATA GAATATTCGG TATTAATCCT GAAAAAGAAA 4500
AATTTGTTTT ATCTATTTTT AATGAAATTA CAAAAACTAA AAAATATTGG GATGGTTGTG 4560
ATTAATATTA ATAACATTAA AAAAATTTTA GAAAATAAAA TCACCTTTTT GTCTGACATT 4620
```

-continued

| | | | | | | |
|---|---|---|---|---|---|---|
| GAAAAAGCTA | CATATATTAT | AGAAAATCAA | AGTGAGTATT | GGGATCCTTA | TACTCTATCT | 4680 |
| CATGGTTATC | CAGGTATAAT | ACTTTTTTTA | AGCGCATCAG | AAAAAGTATT | TCATAAAGAT | 4740 |
| TTAGAAAAAG | TAATACATCA | ATATATTAGA | AAACTAGGCC | CTTATTTAGA | AAGTGGTATT | 4800 |
| GATGGATTTT | CACTTTTTAG | TGGTCTTTCC | GGAATTGGAT | TTGCGCTAGA | CATTGCGTCT | 4860 |
| GATAAACAGT | ACTCTTATCA | AAGTATCTTA | GAACAAATTG | ATAATTTACT | TGTTCAATAT | 4920 |
| GTTTTTGATT | TTTTAAATAA | CGATGCATTG | GAAGTAACCC | CTACTAACTA | TGATATAATA | 4980 |
| CAAGGATTTT | CTGGTATAGG | AAGGTACTTG | TTAAATAGAA | TATCGTATAA | TTATAATGCA | 5040 |
| AAAAAAGCAT | TAAAGCATAT | ACTTAATTAC | TTCAAAACAA | TTCATTACTC | TAAAGACAAT | 5100 |
| TGGTTAGTTT | CAAATGAACA | TCAATTTTTA | GATATAGATA | AGCAAAATTT | TCCGTCAGGA | 5160 |
| AATATAAATT | TAGGATTAGC | GCATGGTATT | TTAGGTCCTC | TATCATTAAC | AGCTTTGAGT | 5220 |
| AAAATGAATG | GGATTGAAAT | CGAAGGCCAT | GAAGAGTTTT | TACAAGACTT | CACTTCATTT | 5280 |
| TTGCTCAAAC | CTGAATTCAA | AAATAATAAT | GAATGGTTCG | ATCGCTATGA | TATATTAGAA | 5340 |
| AATTATATAC | CTAATTATTC | CGTCAGAAAC | GGTTGGTGTT | ACGGTGATAC | AGGGATTATG | 5400 |
| AATACATTAC | TTTTGTCTGG | TAAAGCCTTA | AATAATGAAG | GCTTAATTAA | AATGTCTAAA | 5460 |
| AATATTTTAA | TTAACATAAT | AGATAAGAAT | AATGATGATT | TAATCAGTCC | AACCTTCTGT | 5520 |
| CACGGACTAG | CATCGCACTT | AACCATTATT | CATCAAGCGA | ATAAATTCTT | TAATCTATCT | 5580 |
| CAAGTAAGCA | CATATATCGA | TACCATTGTC | AGAAAAATTA | TTAGTCATTA | TTCTGAAGAA | 5640 |
| AGTAGTTTTA | TGTTCCAAGA | CATAGAGTAC | TCATACGGAC | AAAAAATTTA | TAAAAACAAA | 5700 |
| GTGGGAATTC | TAGAGGGTGA | ATTAGGTGTT | CTTTTAGCTT | TACTAGATTA | TATTGATACA | 5760 |
| CAAAACCAAT | CAAGGAAAAA | TTGGAAAAAT | ATGTTTTTAA | TAACATAATA | GGAGGAATAA | 5820 |
| GATATGTATG | GAAAATTATT | GATATGCGCT | ACAGCATCGA | TAAATGTAAT | TAATATTAAT | 5880 |
| CACTACATAG | TTGAGTTAAA | GCAACATTTT | GATGAAGTTA | ATATATTATT | TAGTCCTAGT | 5940 |
| AGTAAAAATT | TTATAAATAC | TGATGTTCTC | AAGTTATTTT | GTGATAACTT | GTACGATGAA | 6000 |
| ATTAAAGATC | CTCTTTTAAA | TCATATCAAT | ATTGTAGAAA | ATCATGAATA | TATTTTAGTA | 6060 |
| TTACCTGCAT | CAGCAAATAC | TATTAATAAA | ATAGCTAATG | GTATATGTGA | TAATCTTTTA | 6120 |
| ACTACTGTAT | GTTTAACCGG | ATATCAAAAA | TTATTTATAT | TTCCAAATAT | GAACATAAGA | 6180 |
| ATGTGGGGAA | ATCCATTTTT | ACAAAAAAAT | ATTGATTTAC | TTAAAAATAA | TGATGTGAAA | 6240 |
| GTGTATTCCC | CTGATATGAA | TAAATCATTC | GAAATATCTA | GTGGCCGTTA | CAAAAACAAT | 6300 |
| ATCACAATGC | CTAATATTGA | AAATGTACTA | AATTTTGTAT | TAAATAACGA | AAAAAGACCT | 6360 |
| TTGGATTAAC | AAAGGTCTTT | TCTAATTAAA | ATTTTATATC | CGAGTTTACG | TTCATTAATA | 6420 |
| ATTTCTATCT | CTTTACAATT | TTTTAAACTA | TCCCTTAATC | GATGGATATA | TACATTTATT | 6480 |
| GTATTAGAAT | CAACAAAGTC | TTCTGTATCC | CACACTCCCT | TTTTTAATTC | CTCTTTTGAT | 6540 |
| ACATATCTTC | CAAGATTAAT | ATATAAGCAC | CGTAGAATTT | TTAATTCTAT | ATTAGAAAGA | 6600 |
| TTAACTAAGT | AATTATTAAA | CACAAATTGA | TGGTTTTCAA | AGTCTATAAA | ATCATCATTA | 6660 |
| ACATATTTAA | TATACTTTTT | TATTTCATTT | AAAATTCTAC | ATAATATTAA | ACTTTTGCTT | 6720 |
| TCATTATTTT | TTATAATATA | TAAATCTATG | CCTAAACTAT | AAAAATAACA | CTTCCTACTA | 6780 |
| TAGCTAGTAT | TACCTGTTAT | TATAACTATT | GGAATTTTTC | CTATAAATTC | TTTTAAAAAC | 6840 |
| GTATAATACT | CATCAAACTT | TTCATACACA | ATTATAAAAT | TTGGGTCTAT | ATTTGAAGAA | 6900 |
| TTAATTGTAA | TTCTTCTATC | TAATTCTAAA | ATACTTTCAA | TAAGAATAGA | ATCTACCTCA | 6960 |
| CCGACAATAT | TAATAGAAAT | CATTTTATTC | CCTTCATTCT | TTAAGTAATT | TGTATACGTC | 7020 |

-continued

| | | | | | | |
|---|---|---|---|---|---|---|
| TAGTTTTCCA | TTACCATAAT | GTTTTTTATC | CATATATTTT | TCTTTTTCTA | TCCCTTTTTT | 7080 |
| CTTAAATAAC | TCTATAGCTG | TTTCGGGTTG | GTCTTTTAAT | TGATACTTAT | CAATTTCTAG | 7140 |
| TGCTAAAGCT | CCAGAAACCT | TGGGTGCAGC | AAGTGATGTC | CCTGATTGAT | ATATGTATCT | 7200 |
| TCCATTAGAA | GAAGTACTTA | AAACACTTTG | TTTTTGCATA | TATCCTTTTT | CTAACCAAGC | 7260 |
| ATCTTTTCCA | TACTTATCTA | AAAGTTTATA | AGAACCTCCT | ATCGTCATTA | AATCTATAAA | 7320 |
| ATTATTTCCA | TAATTAGAAA | ACTCAGAAAT | ATAATCATTA | TCATCGATGG | ATCCTACAGT | 7380 |
| CATAACATTA | TTTAGATTTG | CTGGGCTATC | ATATACCTTT | TTTGATGTTT | TAGAATTTAG | 7440 |
| ATTTCTTTTT | TTATTTATTT | CTTTTACTTT | TTTTACATTG | ATACCGTCAT | TACCCACAGC | 7500 |
| TGCAACAACA | ATACTACCTT | TTTTTTGAGC | ATAGTTTATA | GCTTTCTGTA | GTGCATCGTA | 7560 |
| ATCAACTTTT | TCATCATCTC | TTAATTTTTT | TTTATTTTGA | TTATCTTTAA | TTAAATAATT | 7620 |
| TCCTAAACTA | ACGTTGATTA | CATCATTGTC | ATCATTTGCT | GCATCAATAA | TTCCTTTAGA | 7680 |
| TACCCAAAGC | ATTTCACTTT | TCTTTGAGCC | AAATACTCGG | TATACATTCA | TCTCTACTCC | 7740 |
| AGGGTTTACA | CCTTTTAAAT | TACCGTTTGC | TCCTATTTGT | CCTGCTACTA | ATGTACCATG | 7800 |
| ATTCAATTTA | TCTTCTTCAA | AATTTTTATT | TCCTGATTCA | TCGTTTTCGC | TACCTCTAAA | 7860 |
| ACCATTTTTA | GGCACTTCAT | TAACTATCTT | ATTTATACTC | TTTAAATCTG | TATGACTACT | 7920 |
| ATTCACACCA | GAATCTACTA | AAGCAACTTT | TGCTTTTTTT | CTATCTGGAC | TTAGCTTATA | 7980 |
| ACTTTTACCT | TCATTTGTTA | TTTTTCGCAT | ATCCCATTGT | CTGTCAAATA | AATCATGGCT | 8040 |
| GCCATTTTTT | TTATTATTTA | AATTTTTTCC | TGTCTTTACA | GATTTTTCAA | CTACACAAGT | 8100 |
| GGAACAGGTA | GGATTTACAA | ACTTGACGTT | TTTATTACTC | TTTATTAGTG | AATTTAATTT | 8160 |
| TGATTTGCTA | GTTTTAATTT | GTGCTGTATG | TAGTTCAGGA | ATTTTATAAG | TTAACTCGAT | 8220 |
| ATTTTTTTGT | TTAATGGATT | CTTTAAAAGT | TTTTGCATTA | TCATATTCAA | CACTATAATA | 8280 |
| ACTTAATTCT | TCATTTAGTG | AACTTCCAAA | AGCATACTCA | TTTTGCAAAA | AAACTAATGA | 8340 |
| CAATATTAAA | AAAACAATGA | AAAATTTAAA | TTTGTTCATA | TAGCACCTCT | AACATATTAT | 8400 |
| TTATATTAAA | CATTAATTTA | ACACTTATGT | TTTTACTTTT | TTATTTATAT | TATCTTTAAT | 8460 |
| AATGTTCTGT | TGCAAGATGA | AAAATACGAG | GTATCAAAGT | ACCGATACAG | CGAGTATTAC | 8520 |
| ACTCAATTAA | TTAAAAATAA | AATATGTTGT | GATTAAAATT | TATTTTATAA | AAGTATGGGC | 8580 |
| AATTTATTAT | TATTCAAGTT | AAAACAAAGA | GTCCGGGACA | TAAAGTTTCA | GCCTCTTCGT | 8640 |
| CCTAATTACC | AAAAAACTTA | CTCCAAAATC | CTTTTTTAGA | TTGGTTTTTT | CTAATTTTTT | 8700 |

( 2 ) INFORMATION FOR SEQ ID NO:17:

( i ) SEQUENCE CHARACTERISTICS:
( A ) LENGTH: 275 amino acids
( B ) TYPE: amino acid
( D ) TOPOLOGY: linear ( x i ) SEQUENCE DESCRIPTION: SEQ ID NO:17:

Asp Gln Thr Ile Tyr Ser Phe Leu Asn Arg Trp Glu Tyr Lys Ser Phe
1 5 10 15

Gln Ser Asp Leu Lys Lys Asp Leu Tyr Ile Asn Gly Thr Tyr Glu Thr
20 25 30

Asn Leu Gly Ala Leu Ile Asn Leu Leu Thr Ser Lys Gly Cys Gly Ser
35 40 45

Glu Gly Ile Ile Asn Tyr Ile Tyr Gly Lys His Leu Asp Leu Ser Ile
50 55 60

Ser Asn Ile Ile Gln Lys Asn Asp Lys Thr Phe Asn Leu Asp Asn Ile
65 70 75 80

-continued

Glu Met Lys Gln Val Phe Asn Asn Tyr Thr Thr Lys Ile Thr Leu Val
85 90 95

Glu Glu Pro Glu Lys Asn Ile Lys Leu Ile Arg Asp Ser Ser Gly Ile
100 105 110

Ala Arg Gln Val Glu Thr Trp Tyr Ser Thr Ile Ser Val Ile Pro Asn
115 120 125

Ile Ile Gln Glu Leu Tyr Leu Val Tyr Ala Phe Met Asp Gly Ser Lys
130 135 140

Met Met Asn Asn Glu Met Leu Tyr Tyr Gly Leu Phe Leu Ile Gly Phe
145 150 155 160

Ile Asn Ile Phe Leu Ile Leu Asn Met Ile Pro Glu Phe Phe Ser Leu
165 170 175

Val Lys Ile Lys His Leu Glu Ile Asp Phe Ile Asn Lys Leu Leu Thr
180 185 190

Tyr Asn Lys Ile Lys Glu Ile Asn Tyr Thr Ser Leu Thr Lys Ile Leu
195 200 205

Lys Ile Thr Ser Leu Arg Asn Ser Tyr Tyr Ser Ser Leu Lys Ala Thr
210 215 220

Ala Glu Gln Ser Lys Ser Ser Val Arg Lys Met Ile Asn Gly Ile Pro
225 230 235 240

Leu Ile Val Ile Ile Leu Ile Pro Leu Thr Cys Val Leu Tyr Leu Thr
245 250 255

Leu Thr Lys Asn Ile Ile Tyr Leu Phe Ile Leu Ser Val Ile Val Ser
260 265 270

Phe Leu Asn
275

( 2 ) INFORMATION FOR SEQ ID NO:18:

( i ) SEQUENCE CHARACTERISTICS:
( A ) LENGTH: 148 amino acids
( B ) TYPE: amino acid
( D ) TOPOLOGY: linear ( x i ) SEQUENCE DESCRIPTION: SEQ ID NO:18:

Ser Leu Lys Gly Asp Asp Ile Ile Lys Gly Leu Tyr Asp Leu Trp Lys
1 5 10 15

Ile Thr Lys Pro Asn Thr Leu Leu Leu Ser Ile Gly Leu Ile Phe Ser
20 25 30

Leu Ile Gly Thr Ser Phe Ser Leu Tyr Ile Pro Leu Ile Ile Arg Asn
35 40 45

Ala Leu Asn Lys Ser Ser Leu Ser Thr Asp Lys Ile Val Ile Ile Ile
50 55 60

Ile Cys Phe Gly Leu Thr Leu Ile Phe Ser Gly Val Ser Thr Tyr Ile
65 70 75 80

Leu Gly Tyr Ile Gly Gln Lys Ile Ile Gln Asn Ile Arg Ser Val Thr
85 90 95

Trp Asn Lys Val Ile Lys Leu Pro Tyr Ser Phe His Leu Lys Asn Ser
100 105 110

Ala Ser Asn Leu Thr Ser Arg Leu Val Asn Asp Thr Met Asn Ile Thr
115 120 125

Arg Val Phe Ser Val Glu Phe Ile Phe Ser Tyr Ser Ile Thr Asn Ile
130 135 140

Phe Ile Tyr Asn
145

( 2 ) INFORMATION FOR SEQ ID NO:19:

( i ) SEQUENCE CHARACTERISTICS:
( A ) LENGTH: 52 amino acids
( B ) TYPE: amino acid
( D ) TOPOLOGY: linear ( x i ) SEQUENCE DESCRIPTION: SEQ ID NO:19:

Met Glu Ala Val Lys Glu Lys Asn Asp Leu Phe Asn Leu Asp Val Lys
1 5 10 15

Val Asn Ala Lys Glu Ser Asn Asp Ser Gly Ala Glu Pro Arg Ile Ala
20 25 30

Ser Lys Phe Ile Cys Thr Pro Gly Cys Ala Lys Thr Gly Ser Phe Asn
35 40 45

Ser Tyr Cys Cys
50

( 2 ) INFORMATION FOR SEQ ID NO:20:

( i ) SEQUENCE CHARACTERISTICS:
( A ) LENGTH: 990 amino acids
( B ) TYPE: amino acid
( D ) TOPOLOGY: linear ( x i ) SEQUENCE DESCRIPTION: SEQ ID NO:20:

Gly Glu Ile Glu Leu Asp Asn Ile Phe Val Pro Ser Asn Ile Tyr Met
1 5 10 15

Val Arg Thr Pro Ile Phe Ser Ile Glu Leu Tyr Asn Gln Phe Leu Lys
20 25 30

Ser Asp Asn Ile Asp Tyr Asp Leu Ile Leu Gln Asn Asp Ile Phe Lys
35 40 45

Glu Ser Ile Met Thr Thr Thr Tyr Asn Leu Tyr Gln Ser Ile Gly Lys
50 55 60

Ile Asp Trp Glu Lys Asp Asn Lys Lys Thr Arg Asn Val Lys Glu Ser
65 70 75 80

Leu Leu Lys Tyr Leu Ile Arg Met Ser Thr Arg Ser Thr Pro Tyr Gly
85 90 95

Met Leu Ser Gly Val Ala Leu Gly Glu Phe Ser Glu Asn Asn Asn Ile
100 105 110

Lys Ile Lys Asp Ser Ser Phe His Lys Lys Asp Val Lys Ile Asp Gly
115 120 125

Gln Trp Leu Tyr Lys Leu Val His Tyr Leu Glu Ser Asp Tyr Thr Tyr
130 135 140

Tyr Lys Asp Ser Phe Val Ile Trp Asn Gln Gln Asn Tyr Ile Tyr Asn
145 150 155 160

Asn Arg Leu Tyr Leu Asp Asn Asn Ser Ser Ile Thr Glu Asn Lys Arg
165 170 175

Asn Asp Val Leu Ser Val Lys Tyr Asn Ser Ile Leu Val Phe Ile His
180 185 190

Glu Asn Ser Lys Lys Asn Ile Thr Tyr Glu Glu Leu Val Gln Leu Ile
195 200 205

Ser Ser Lys Tyr Ser Ile Glu Asn Lys Glu Glu Val Lys Val Phe Val
210 215 220

Gln Glu Leu Ile Asn Lys Glu Ile Ile Phe Ser Asp Leu Arg Pro Thr
225 230 235 240

Leu Glu Asn Lys Asn Pro Leu Asp Tyr Ile Ile Asn Ser Leu Asn Pro
245 250 255

-continued

Lys Asn Ser Leu Val Gly Thr Leu Ile Asn Ile Ser Asn Glu Ile Thr
260 265 270

Lys Tyr Ser Lys Met Pro Leu Gly Lys Gly Glu Tyr Lys Tyr Leu Asp
275 280 285

Ile Val Asn Leu Met Ser Gln Leu Phe Val Ser Lys Asn Tyr Leu Gln
290 295 300

Ile Asp Thr Tyr Ile Asp Tyr Ser Arg Asn Glu Leu Lys Gln Ser Leu
305 310 315 320

Ala Asp Asn Ile Ser Glu Ala Ala Tyr Ile Leu Trp Leu Leu Ser Pro
325 330 335

His Glu Phe Gly Thr Lys Thr Ile Arg Asn Tyr His Glu Phe Phe Met
340 345 350

Asp Lys Tyr Gly Phe Glu Gln Leu Val Asn Leu Lys Gln Leu Leu Ser
355 360 365

Asp Ile Asn Gly Phe Gly Tyr Pro Lys Lys Asp Ser Tyr Ser Phe Ser
370 375 380

Asn Asn Ile Ala Phe Leu Lys Glu Lys Tyr Leu Leu Ala Ile Gln Asn
385 390 395 400

Asn Ser His Ile Glu Ile Thr Glu Asn Asp Val Lys Asn Leu Glu Lys
405 410 415

Asn Asn Thr Val Ser Lys Ile Asn Ala Pro Val Ser Thr Glu Ile Tyr
420 425 430

Ser Glu Ile Tyr Phe Gly Asn Ser Ile Lys Gly Tyr Glu Asp Phe Ala
435 440 445

Val Ile Ser Pro Ile Leu Gly Ser Phe Asn Ala Gly Ala Thr Phe Gly
450 455 460

Arg Pro Thr Gly Asn Phe Asn Ile Lys Lys Lys Asn Gln Leu Gln Lys
465 470 475 480

Glu Ile Val His His Tyr Asn Asn Tyr Met Asn Glu Asn Asp Leu Glu
485 490 495

Ile Ser Gln Leu Asn Glu Ala Pro Leu Asn Ser Arg Asn Val Asn Ile
500 505 510

Leu Asn Asn Asn Arg Ile Tyr Asn Thr Cys Leu Asn Leu Asn Leu Pro
515 520 525

Lys Ser Asp Ile Asp Ile Asn Asp Ile Phe Ile Gly Ala Thr Phe Asn
530 535 540

Lys Leu Tyr Leu Tyr Ser Glu Lys His Asp Ser Arg Ile Val Phe Val
545 550 555 560

Ser Asn Ser Met Phe Asn Tyr Glu Phe Gly Ser Glu Leu Tyr Lys Phe
565 570 575

Leu Arg Glu Ile Ser Phe Glu Lys Thr Lys Phe Ile Gln Pro Ile Thr
580 585 590

Glu Glu Gly Ile Asp Ser Leu Pro Phe Cys Pro Arg Ile Ile Tyr Lys
595 600 605

Asn Ile Ile Leu Lys Pro Ala Thr Trp Lys Ile Asn Ser Glu Met Phe
610 615 620

Ser Glu Thr Glu Asn Trp Leu Asn Arg Phe Ala Thr Ile Arg Lys Trp
625 630 635 640

His Ile Pro Lys Asp Val Ile Ile Ala Phe Gly Asp Asn Arg Leu Leu
645 650 655

Leu Asn Leu Leu Asn Asp Lys His Leu Ile Ile Leu Lys Lys Glu Leu
660 665 670

Lys Lys His Gly Arg Ile Arg Ile Leu Glu Ser Phe Ile Asn Glu Ser
675 680 685

-continued

Asn Asn Glu Arg Met Leu Glu Ile Val Thr Pro Leu Tyr Lys Lys Thr
690 695 700

Ser Leu Lys Glu Gln Ser Phe Ile Ile Pro Lys Asn Arg Asn Lys His
705 710 715 720

Phe Asn Asn Leu Lys Asp Trp Phe Ser Ile His Leu Ser Ile Pro Lys
725 730 735

Thr Tyr Gln Asp Asn Phe Ile Gln Asp Tyr Leu Leu Pro Phe Ile Thr
740 745 750

Glu Leu Lys Val Asn Asn Phe Ile Asn Lys Phe Phe Tyr Ile Lys Phe
755 760 765

Lys Glu Asp Glu Asp Phe Ile Lys Leu Arg Leu Leu Arg Glu Asp Glu
770 775 780

Asp Tyr Ser Gln Ile Tyr Ser Phe Ile Lys Asn Trp Lys Asp Tyr Cys
785 790 795 800

Leu Leu Asn Ser Glu Leu Tyr Asp Tyr Ser Ile Val Asp Tyr Val Pro
805 810 815

Glu Val Tyr Arg Tyr Gly Gly Pro His Val Ile Glu Asp Ile Glu Asn
820 825 830

Phe Phe Met Tyr Asp Ser Leu Leu Asp Ser Ile Asn Ile Ile Gln Ser
835 840 845

Glu Phe Lys Ile Pro Lys Glu Phe Ile Val Ala Ile Ser Ile Asp Phe
850 855 860

Leu Leu Asp Tyr Leu Glu Ile Asn Lys Ser Glu Lys Glu Glu Ile Leu
865 870 875 880

Ile Asn Asn Ala Glu Asp Leu Tyr Arg Ser Asn Asp Ile Arg Glu Tyr
885 890 895

Lys Asn Leu Leu Ala Lys Leu Thr Asn Pro Lys Asn Asp Tyr Glu Ile
900 905 910

Leu Lys Lys Glu Phe Pro Asn Leu His Glu Phe Leu Phe Asn Lys Ile
915 920 925

Ser Ile Leu Glu Asn Leu Lys Lys Thr Leu Gln Lys Ser Leu Tyr Thr
930 935 940

Ser Arg Ser Arg Ile Ile Gly Ser Phe Ile His Met Arg Cys Asn Arg
945 950 955 960

Ile Phe Gly Ile Asn Pro Glu Lys Glu Lys Phe Val Leu Ser Ile Phe
965 970 975

Asn Glu Ile Thr Lys Thr Lys Lys Tyr Trp Asp Gly Cys Asp
980 985 990

( 2 ) INFORMATION FOR SEQ ID NO:21:

( i ) SEQUENCE CHARACTERISTICS:
( A ) LENGTH: 455 amino acids
( B ) TYPE: amino acid
( D ) TOPOLOGY: linear ( x i ) SEQUENCE DESCRIPTION: SEQ ID NO:21:

Leu Ala Val Leu Tyr Thr Cys Val Val Ile Glu Tyr Ser Val Leu Ile
1 5 10 15

Leu Lys Lys Lys Asn Leu Phe Tyr Leu Phe Leu Met Lys Leu Gln Lys
20 25 30

Leu Lys Asn Ile Gly Met Val Val Ile Asn Ile Asn Asn Ile Lys Lys
35 40 45

Ile Leu Glu Asn Lys Ile Thr Phe Leu Ser Asp Ile Glu Lys Ala Thr
50 55 60

-continued

```
Tyr Ile Ile Glu Asn Gln Ser Glu Tyr Trp Asp Pro Tyr Thr Leu Ser
65                  70                  75                  80

His Gly Tyr Pro Gly Ile Ile Leu Phe Leu Ser Ala Ser Glu Lys Val
                85                  90                  95

Phe His Lys Asp Leu Glu Lys Val Ile His Gln Tyr Ile Arg Lys Leu
            100                 105                 110

Gly Pro Tyr Leu Glu Ser Gly Ile Asp Gly Phe Ser Leu Phe Ser Gly
        115                 120                 125

Leu Ser Gly Ile Gly Phe Ala Leu Asp Ile Ala Ser Asp Lys Gln Tyr
    130                 135                 140

Ser Tyr Gln Ser Ile Leu Glu Gln Ile Asp Asn Leu Leu Val Gln Tyr
145                 150                 155                 160

Val Phe Asp Phe Leu Asn Asn Asp Ala Leu Glu Val Thr Pro Thr Asn
                165                 170                 175

Tyr Asp Ile Ile Gln Gly Phe Ser Gly Val Gly Arg Tyr Leu Leu Asn
            180                 185                 190

Arg Ile Ser Tyr Asn Tyr Asn Ala Lys Lys Ala Leu Lys His Ile Leu
        195                 200                 205

Asn Tyr Phe Lys Thr Ile His Tyr Ser Lys Asp Asn Trp Leu Val Ser
    210                 215                 220

Asn Glu His Gln Phe Leu Asp Ile Asp Lys Gln Asn Phe Pro Ser Gly
225                 230                 235                 240

Asn Ile Asn Leu Gly Leu Ala His Gly Ile Leu Gly Pro Leu Ser Leu
                245                 250                 255

Thr Ala Leu Ser Lys Met Asn Gly Ile Glu Ile Glu Gly His Glu Glu
            260                 265                 270

Phe Leu Gln Asp Phe Thr Ser Phe Leu Leu Lys Pro Glu Phe Lys Asn
        275                 280                 285

Asn Asn Glu Trp Phe Asp Arg Tyr Asp Ile Leu Glu Asn Tyr Ile Pro
    290                 295                 300

Asn Tyr Ser Val Arg Asn Gly Trp Cys Tyr Gly Asp Thr Gly Ile Met
305                 310                 315                 320

Asn Thr Leu Leu Leu Ser Gly Lys Ala Leu Asn Asn Glu Gly Leu Ile
                325                 330                 335

Lys Met Ser Lys Asn Ile Leu Ile Asn Ile Ile Asp Lys Asn Asn Asp
            340                 345                 350

Asp Leu Ile Ser Pro Thr Phe Cys His Gly Leu Ala Ser His Leu Thr
        355                 360                 365

Ile Ile His Gln Ala Asn Lys Phe Phe Asn Leu Ser Gln Val Ser Thr
    370                 375                 380

Tyr Ile Asp Thr Ile Val Arg Lys Ile Ile Ser His Tyr Ser Glu Glu
385                 390                 395                 400

Ser Ser Phe Met Phe Gln Asp Ile Glu Tyr Ser Tyr Gly Gln Lys Ile
                405                 410                 415

Tyr Lys Asn Lys Val Gly Ile Leu Glu Gly Glu Leu Gly Val Leu Leu
            420                 425                 430

Ala Leu Leu Asp Tyr Ile Asp Thr Gln Asn Gln Ser Arg Lys Asn Trp
        435                 440                 445

Lys Asn Met Phe Leu Ile Thr
    450                 455
```

( 2 ) INFORMATION FOR SEQ ID NO:22:

( i ) SEQUENCE CHARACTERISTICS:

( A ) LENGTH: 181 amino acids ( B ) TYPE: amino acid
( D ) TOPOLOGY: linear ( x i ) SEQUENCE DESCRIPTION: SEQ ID NO:22:

Met Tyr Gly Lys Leu Leu Ile Cys Ala Thr Ala Ser Ile Asn Val Ile
1 5 10 15

Asn Ile Asn His Tyr Ile Val Glu Leu Lys Gln His Phe Asp Glu Val
20 25 30

Asn Ile Leu Phe Ser Pro Ser Ser Lys Asn Phe Ile Asn Thr Asp Val
35 40 45

Leu Lys Leu Phe Cys Asp Asn Leu Tyr Asp Glu Ile Lys Asp Pro Leu
50 55 60

Leu Asn His Ile Asn Ile Val Glu Asn His Glu Tyr Ile Leu Val Leu
65 70 75 80

Pro Ala Ser Ala Asn Thr Ile Asn Lys Ile Ala Asn Gly Ile Cys Asp
85 90 95

Asn Leu Leu Thr Thr Val Cys Leu Thr Gly Tyr Gln Lys Leu Phe Ile
100 105 110

Phe Pro Asn Met Asn Ile Arg Met Trp Gly Asn Pro Phe Leu Gln Lys
115 120 125

Asn Ile Asp Leu Leu Lys Asn Asn Asp Val Lys Val Tyr Ser Pro Asp
130 135 140

Met Asn Lys Ser Phe Glu Ile Ser Ser Gly Arg Tyr Lys Asn Asn Ile
145 150 155 160

Thr Met Pro Asn Ile Glu Asn Val Leu Asn Phe Val Leu Asn Asn Glu
165 170 175

Lys Arg Pro Leu Asp
180

( 2 ) INFORMATION FOR SEQ ID NO:23:

( i ) SEQUENCE CHARACTERISTICS:
( A ) LENGTH: 205 amino acids
( B ) TYPE: amino acid
( D ) TOPOLOGY: linear ( x i ) SEQUENCE DESCRIPTION: SEQ ID NO:23:

Met Ile Ser Ile Asn Ile Val Gly Glu Val Asp Ser Ile Leu Ile Glu
1 5 10 15

Ser Ile Leu Glu Leu Asp Arg Arg Ile Thr Ile Asn Ser Ser Asn Ile
20 25 30

Asp Pro Asn Phe Ile Ile Val Tyr Glu Lys Phe Asp Glu Tyr Tyr Thr
35 40 45

Phe Leu Lys Glu Phe Ile Gly Lys Ile Pro Ile Val Ile Ile Thr Gly
50 55 60

Asn Thr Ser Tyr Ser Arg Lys Cys Tyr Phe Tyr Ser Leu Gly Ile Asp
65 70 75 80

Leu Tyr Ile Ile Lys Asn Asn Glu Ser Lys Ser Leu Ile Leu Cys Arg
85 90 95

Ile Leu Asn Glu Ile Lys Lys Tyr Ile Lys Tyr Val Asn Asp Asp Phe
100 105 110

Ile Asp Phe Glu Asn His Gln Phe Val Phe Asn Asn Tyr Leu Val Asn
115 120 125

Leu Ser Asn Ile Glu Leu Lys Ile Leu Arg Cys Leu Tyr Ile Asn Leu
130 135 140

Gly Arg Tyr Val Ser Lys Glu Glu Leu Lys Lys Gly Val Trp Asp Thr
145 150 155 160

Glu Asp Phe Val Asp Ser Asn Thr Ile Asn Val Tyr Ile His Arg Leu
165 170 175

Arg Asp Ser Leu Lys Asn Cys Lys Glu Ile Glu Ile Ile Asn Glu Arg
180 185 190

Lys Leu Gly Tyr Lys Ile Leu Ile Arg Lys Asp Leu Cys
195 200 205

( 2 ) INFORMATION FOR SEQ ID NO:24:

( i ) SEQUENCE CHARACTERISTICS:
( A ) LENGTH: 461 amino acids
( B ) TYPE: amino acid
( D ) TOPOLOGY: linear ( x i ) SEQUENCE DESCRIPTION: SEQ ID NO:24:

Met Asn Lys Phe Lys Phe Phe Ile Val Phe Leu Ile Leu Ser Leu Val
1 5 10 15

Phe Leu Gln Asn Glu Tyr Ala Phe Gly Ser Ser Leu Asn Glu Glu Leu
20 25 30

Ser Tyr Tyr Ser Val Glu Tyr Asp Asn Ala Lys Thr Phe Lys Glu Ser
35 40 45

Ile Lys Gln Lys Asn Ile Glu Leu Thr Tyr Lys Ile Pro Glu Leu His
50 55 60

Thr Ala Gln Ile Lys Thr Ser Lys Ser Lys Leu Asn Ser Leu Ile Lys
65 70 75 80

Ser Asn Lys Asn Val Lys Phe Val Asn Pro Thr Cys Ser Thr Cys Val
85 90 95

Val Glu Lys Ser Val Lys Thr Gly Lys Asn Leu Asn Asn Lys Lys Asn
100 105 110

Gly Ser His Asp Leu Phe Asp Arg Gln Trp Asp Met Arg Lys Ile Thr
115 120 125

Asn Glu Gly Lys Ser Tyr Lys Leu Ser Pro Asp Arg Lys Lys Ala Lys
130 135 140

Val Ala Leu Val Asp Ser Gly Val Asn Ser Ser His Thr Asp Leu Lys
145 150 155 160

Ser Ile Asn Lys Ile Val Asn Glu Val Pro Lys Asn Gly Phe Arg Gly
165 170 175

Ser Glu Asn Asp Glu Ser Gly Asn Lys Asn Phe Glu Glu Asp Lys Leu
180 185 190

Asn His Gly Thr Leu Val Ala Gly Gln Ile Gly Ala Asn Gly Asn Leu
195 200 205

Lys Gly Val Asn Pro Gly Val Glu Met Asn Val Tyr Arg Val Phe Gly
210 215 220

Ser Lys Lys Ser Glu Met Leu Trp Val Ser Lys Gly Ile Ile Asp Ala
225 230 235 240

Ala Asn Asp Asp Asn Asp Val Ile Asn Val Ser Leu Gly Asn Tyr Leu
245 250 255

Ile Lys Asp Asn Gln Asn Lys Lys Lys Leu Arg Asp Asp Glu Lys Val
260 265 270

Asp Tyr Asp Ala Leu Gln Lys Ala Ile Asn Tyr Ala Gln Lys Lys Gly
275 280 285

Ser Ile Val Val Ala Ala Val Gly Asn Asp Gly Ile Asn Val Lys Lys
290 295 300

Val Lys Glu Ile Asn Lys Lys Arg Asn Leu Asn Ser Lys Thr Ser Lys
305 310 315 320

```
Lys Val Tyr Asp Ser Pro Ala Asn Leu Asn Asn Val Met Thr Val Gly
                325                 330                 335

Ser Ile Asp Asp Asn Asp Tyr Ile Ser Glu Phe Ser Asn Tyr Gly Asn
            340                 345                 350

Asn Phe Ile Asp Leu Met Thr Ile Gly Gly Ser Tyr Lys Leu Leu Asp
        355                 360                 365

Lys Tyr Gly Lys Asp Ala Trp Leu Glu Lys Gly Tyr Met Gln Lys Gln
    370                 375                 380

Ser Val Leu Ser Thr Ser Ser Asn Gly Arg Tyr Ile Tyr Gln Ser Gly
385                 390                 395                 400

Thr Ser Leu Ala Ala Pro Lys Val Ser Gly Ala Leu Ala Leu Glu Ile
                405                 410                 415

Asp Lys Tyr Gln Leu Lys Asp Gln Pro Glu Thr Ala Ile Glu Leu Phe
            420                 425                 430

Lys Lys Lys Gly Ile Glu Lys Glu Lys Tyr Met Asp Lys Lys His Tyr
        435                 440                 445

Gly Asn Gly Lys Leu Asp Val Tyr Lys Leu Leu Lys Glu
    450                 455                 460
```

( 2 ) INFORMATION FOR SEQ ID NO:25:

( i ) SEQUENCE CHARACTERISTICS:
( A ) LENGTH: 41 amino acids
( B ) TYPE: amino acid
( D ) TOPOLOGY: linear ( x i ) SEQUENCE DESCRIPTION: SEQ ID NO:25:

```
Glu Gly Lys Ser Tyr Lys Leu Ser Pro Asp Arg Lys Lys Ala Lys Val
1               5                   10                  15

Ala Leu Val Asp Ser Gly Val Asn Ser Ser His Thr Asp Leu Lys Ser
            20                  25                  30

Ile Asn Lys Ile Val Asn Glu Val Pro
        35                  40
```

( 2 ) INFORMATION FOR SEQ ID NO:26:

( i ) SEQUENCE CHARACTERISTICS:
( A ) LENGTH: 41 amino acids
( B ) TYPE: amino acid
( D ) TOPOLOGY: linear ( x i ) SEQUENCE DESCRIPTION: SEQ ID NO:26:

```
Ala Pro Ala Leu His Ser Gln Gly Tyr Thr Gly Ser Asn Val Lys Val
1               5                   10                  15

Ala Val Ile Asp Ser Gly Ile Asp Ser Ser His Pro Asp Leu Asn Val
            20                  25                  30

Arg Gly Gly Ala Ser Phe Val Pro Ser
        35                  40
```

( 2 ) INFORMATION FOR SEQ ID NO:27:

( i ) SEQUENCE CHARACTERISTICS:
( A ) LENGTH: 41 amino acids
( B ) TYPE: amino acid
( D ) TOPOLOGY: linear ( x i ) SEQUENCE DESCRIPTION: SEQ ID NO:27:

```
Ala Pro Glu Met Trp Ala Lys Gly Val Lys Gly Lys Asn Ile Lys Val
1               5                   10                  15

Ala Val Leu Asp Thr Gly Cys Asp Thr Ser His Pro Asp Leu Lys Asn
            20                  25                  30
```

-continued

Gln Ile Ile Gly Gly Lys Asn Phe Ser
35 40

(2) INFORMATION FOR SEQ ID NO:28:

(i) SEQUENCE CHARACTERISTICS:
(A) LENGTH: 41 amino acids
(B) TYPE: amino acid
(D) TOPOLOGY: linear (xi) SEQUENCE DESCRIPTION: SEQ ID NO:28:

Gln Ala Pro Gln Ala Trp Asp Ile Ala Glu Gly Ser Gly Ala Lys Ile
1 5 10 15

Ala Ile Val Asp Thr Gly Val Gln Ser Asn His Pro Asp Leu Ala Gly
20 25 30

Lys Val Val Gly Gly Trp Asp Phe Val
35 40

(2) INFORMATION FOR SEQ ID NO:29:

(i) SEQUENCE CHARACTERISTICS:
(A) LENGTH: 51 amino acids
(B) TYPE: amino acid
(D) TOPOLOGY: linear (xi) SEQUENCE DESCRIPTION: SEQ ID NO:29:

Pro Lys Asn Gly Phe Arg Gly Ser Glu Asn Asp Glu Ser Gly Asn Lys
1 5 10 15

Asn Phe Glu Glu Asp Lys Leu Asn His Gly Thr Leu Val Ala Gly Gln
20 25 30

Ile Gly Ala Asn Gly Asn Leu Lys Gly Val Asn Pro Gly Val Glu Met
35 40 45

Asn Val Tyr
50

(2) INFORMATION FOR SEQ ID NO:30:

(i) SEQUENCE CHARACTERISTICS:
(A) LENGTH: 51 amino acids
(B) TYPE: amino acid
(D) TOPOLOGY: linear (xi) SEQUENCE DESCRIPTION: SEQ ID NO:30:

Pro Asp Leu Asn Val Arg Gly Gly Ala Ser Phe Val Pro Ser Glu Thr
1 5 10 15

Asn Pro Tyr Gln Asp Gly Ser Ser His Gly Thr His Val Ala Gly Thr
20 25 30

Ile Ala Ala Leu Asn Asn Ser Ile Gly Val Leu Gly Val Ser Pro Ser
35 40 45

Ala Ser Leu
50

(2) INFORMATION FOR SEQ ID NO:31:

(i) SEQUENCE CHARACTERISTICS:
(A) LENGTH: 51 amino acids
(B) TYPE: amino acid
(D) TOPOLOGY: linear (xi) SEQUENCE DESCRIPTION: SEQ ID NO:31:

Gln Ile Ile Gly Gly Lys Asn Phe Ser Asp Asp Asp Gly Gly Lys Glu
1 5 10 15

-continued

Asp Ala Ile Ser Asp Tyr Asn Gly His Gly Thr His Val Ala Gly Thr
20 25 30

Ile Ala Ala Asn Asp Ser Asn Gly Gly Ile Ala Gly Val Ala Pro Glu
35 40 45

Ala Ser Leu
50

( 2 ) INFORMATION FOR SEQ ID NO:32:

( i ) SEQUENCE CHARACTERISTICS:
( A ) LENGTH: 21 amino acids
( B ) TYPE: amino acid
( D ) TOPOLOGY: linear ( x i ) SEQUENCE DESCRIPTION: SEQ ID NO:32:

Asn Gly Asn Gly His Gly Thr His Cys Ala Gly Ile Ala Ala Ala Val
1 5 10 15

Thr Asn Asn Ser Thr
20

( 2 ) INFORMATION FOR SEQ ID NO:33:

( i ) SEQUENCE CHARACTERISTICS:
( A ) LENGTH: 41 amino acids
( B ) TYPE: amino acid
( D ) TOPOLOGY: linear ( x i ) SEQUENCE DESCRIPTION: SEQ ID NO:33:

Tyr Met Gln Lys Gln Ser Val Leu Ser Thr Ser Ser Asn Gly Arg Tyr
1 5 10 15

Ile Tyr Gln Ser Gly Thr Ser Leu Ala Ala Pro Lys Val Ser Gly Ala
20 25 30

Leu Ala Leu Glu Ile Asp Lys Tyr Gln
35 40

( 2 ) INFORMATION FOR SEQ ID NO:34:

( i ) SEQUENCE CHARACTERISTICS:
( A ) LENGTH: 41 amino acids
( B ) TYPE: amino acid
( D ) TOPOLOGY: linear ( x i ) SEQUENCE DESCRIPTION: SEQ ID NO:34:

Met Ala Pro Gly Val Ser Ile Gln Ser Thr Leu Pro Gly Gly Thr Tyr
1 5 10 15

Gly Ala Tyr Asn Gly Thr Ser Met Ala Thr Pro His Val Ala Gly Ala
20 25 30

Ala Ala Leu Ile Leu Ser Lys His Pro
35 40

( 2 ) INFORMATION FOR SEQ ID NO:35:

( i ) SEQUENCE CHARACTERISTICS:
( A ) LENGTH: 35 amino acids
( B ) TYPE: amino acid
( D ) TOPOLOGY: linear ( x i ) SEQUENCE DESCRIPTION: SEQ ID NO:35:

Val Ala Pro Gly Glu Asn Ile Leu Ser Thr Leu Pro Asn Lys Lys Tyr
1 5 10 15

Gly Lys Leu Thr Gly Thr Ser Met Ala Ala Pro His Val Ser Gly Ala
20 25 30

Leu Ala Leu

35

(2) INFORMATION FOR SEQ ID NO:36:

(i) SEQUENCE CHARACTERISTICS:
(A) LENGTH: 5 amino acids
(B) TYPE: amino acid
(D) TOPOLOGY: linear (xi) SEQUENCE DESCRIPTION: SEQ ID NO:36:

Ile Lys Ser Tyr Glu
1 5

(2) INFORMATION FOR SEQ ID NO:37:

(i) SEQUENCE CHARACTERISTICS:
(A) LENGTH: 41 amino acids
(B) TYPE: amino acid
(D) TOPOLOGY: linear (xi) SEQUENCE DESCRIPTION: SEQ ID NO:37:

Ala Ala Pro Gly Ser Trp Ile Tyr Ser Thr Tyr Pro Thr Ser Thr Tyr
1 5 10 15

Ala Ser Leu Ser Gly Thr Ser Met Ala Thr Pro His Val Ala Gly Val
20 25 30

Ala Gly Leu Leu Ala Ser Gln Gly Arg
35 40

(2) INFORMATION FOR SEQ ID NO:38:

(i) SEQUENCE CHARACTERISTICS:
(A) LENGTH: 114 amino acids
(B) TYPE: amino acid
(D) TOPOLOGY: linear (xi) SEQUENCE DESCRIPTION: SEQ ID NO:38:

Met Ile Ser Ile Asn Ile Val Gly Glu Val Asp Ser Ile Leu Ile Glu
1 5 10 15

Ser Ile Leu Glu Leu Asp Arg Arg Ile Thr Ile Asn Ser Ser Asn Ile
20 25 30

Asp Pro Asn Phe Ile Ile Val Tyr Glu Lys Phe Asp Glu Tyr Tyr Thr
35 40 45

Phe Leu Lys Glu Phe Ile Gly Lys Ile Pro Ile Val Ile Ile Thr Gly
50 55 60

Asn Thr Ser Tyr Ser Arg Lys Cys Tyr Phe Tyr Ser Leu Gly Ile Asp
65 70 75 80

Leu Tyr Ile Ile Lys Asn Asn Glu Ser Lys Ser Leu Ile Leu Cys Arg
85 90 95

Ile Leu Asn Glu Ile Lys Lys Tyr Ile Lys Tyr Val Asn Asp Asp Phe
100 105 110

Ile Asp (2) INFORMATION FOR SEQ ID NO:39:

(i) SEQUENCE CHARACTERISTICS:
(A) LENGTH: 93 amino acids
(B) TYPE: amino acid
(D) TOPOLOGY: linear (xi) SEQUENCE DESCRIPTION: SEQ ID NO:39:

Val Leu Glu Gln Asn Gly Phe Gln Pro Val Glu Ala Glu Asp Tyr Asp
1 5 10 15

-continued

Ser Ala Val Asn Gln Leu Asn Glu Pro Trp Pro Asp Leu Ile Leu Leu
20 25 30

Asp Trp Met Leu Pro Gly Gly Ser Gly Ile Gln Phe Ile Lys His Leu
35 40 45

Lys Arg Glu Ser Met Thr Arg Asp Ile Pro Val Val Met Leu Thr Ala
50 55 60

Arg Gly Glu Glu Glu Asp Arg Val Arg Gly Leu Glu Thr Gly Ala Asp
65 70 75 80

Asp Tyr Ile Thr Lys Pro Phe Ser Pro Lys Glu Leu Val
85 90

( 2 ) INFORMATION FOR SEQ ID NO:40:

( i ) SEQUENCE CHARACTERISTICS:
( A ) LENGTH: 116 amino acids
( B ) TYPE: amino acid
( D ) TOPOLOGY: linear ( x i ) SEQUENCE DESCRIPTION: SEQ ID NO:40:

Ala Arg Ile Lys Ala Val Met Arg Arg Ile Ser Pro Met Ala Val Glu
1 5 10 15

Glu Val Ile Glu Met Gln Gly Leu Ser Leu Asp Pro Thr Ser His Arg
20 25 30

Val Met Ala Gly Glu Glu Pro Leu Glu Met Gly Pro Thr Glu Phe Lys
35 40 45

Leu Leu His Phe Phe Met Thr His Pro Glu Arg Val Tyr Ser Arg Glu
50 55 60

Gln Leu Leu Asn His Val Trp Gly Thr Asn Val Tyr Val Glu Asp Arg
65 70 75 80

Thr Val Asp Val His Ile Arg Arg Leu Arg Lys Ala Leu Glu Pro Gly
85 90 95

Gly His Asp Arg Met Val Gln Thr Val Arg Gly Thr Gly Tyr Arg Phe
100 105 110

Ser Thr Arg Phe
115

( 2 ) INFORMATION FOR SEQ ID NO:41:

( i ) SEQUENCE CHARACTERISTICS:
( A ) LENGTH: 75 amino acids
( B ) TYPE: amino acid
( D ) TOPOLOGY: linear ( x i ) SEQUENCE DESCRIPTION: SEQ ID NO:41:

Asn His Gln Phe Val Phe Asn Asn Tyr Leu Val Asn Leu Ser Asn Ile
1 5 10 15

Glu Leu Lys Ile Leu Arg Cys Leu Tyr Ile Asn Leu Gly Arg Tyr Val
20 25 30

Ser Lys Glu Glu Leu Lys Lys Gly Val Trp Asp Thr Glu Asp Phe Val
35 40 45

Asp Ser Asn Thr Ile Asn Val Tyr Ile His Arg Leu Arg Asp Ser Leu
50 55 60

Lys Asn Cys Lys Glu Ile Glu Ile Ile Asn Glu
65 70 75

( 2 ) INFORMATION FOR SEQ ID NO:42:

( i ) SEQUENCE CHARACTERISTICS:
( A ) LENGTH: 14 amino acids
( B ) TYPE: amino acid -continued ( D ) TOPOLOGY: linear ( x i ) SEQUENCE DESCRIPTION: SEQ ID NO:42:

| | | | | | | | | | | | | | |
|---|---|---|---|---|---|---|---|---|---|---|---|---|---|
| Arg | Lys | Leu | Gly | Tyr | Lys | Ile | Leu | Ile | Arg | Lys | Asp | Leu | Cys |
| 1 | | | | 5 | | | | | 10 | | | | |